(12) United States Patent
Song et al.

(10) Patent No.: US 6,563,025 B1
(45) Date of Patent: May 13, 2003

(54) NUCLEOTIDE SEQUENCES ENCODING ANTHRANILATE SYNTHASE

(75) Inventors: Hee-Sook Song, Groton, CT (US); Jeffrey E. Brotherton, Urbana; Jack M. Widholm, Champaign, both of IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/264,854

(22) Filed: Mar. 8, 1999

Related U.S. Application Data

(63) Continuation-in-part of application No. 09/001,826, filed on Dec. 31, 1997, now Pat. No. 5,965,727, which is a continuation-in-part of application No. 08/937,739, filed on Jul. 25, 1997, now abandoned.
(60) Provisional application No. 60/025,140, filed on Jul. 26, 1996.

(51) Int. Cl.$^7$ .................. C12N 15/09; C12N 15/29; C12N 15/82; A01H 5/00; A01H 5/10
(52) U.S. Cl. .................. 800/300; 800/278; 800/298; 800/295; 800/317; 435/69.1; 435/468; 435/419; 435/430; 536/23.1; 536/23.2; 536/23.6; 536/24.1
(58) Field of Search .................. 800/278, 298, 800/295, 317.3; 435/69.1, 468, 419, 430; 536/23.1, 23.2, 23.6, 24.1

(56) References Cited

U.S. PATENT DOCUMENTS

| | | | |
|---|---|---|---|
| 4,642,411 A | 2/1987 | Hibberd et al. | 800/268 |
| 4,886,753 A | 12/1989 | Marcker et al. | 800/287 |
| 5,034,322 A | 7/1991 | Rogers et al. | 435/252.2 |
| 5,290,924 A | 3/1994 | Last et al. | 500/300 |
| 5,352,605 A | 10/1994 | Fraley et al. | 435/418 |
| 5,442,052 A | 8/1995 | Bird et al. | 800/298 |
| 5,466,785 A | 11/1995 | De Framond | 435/469 |
| 5,474,929 A | 12/1995 | Pelcher | 536/24.1 |
| 5,965,727 A | * 10/1999 | Song et al. | 436/24.1 |
| 6,118,047 A | * 9/2000 | Anderson et al. | 800/278 |

FOREIGN PATENT DOCUMENTS

| | | |
|---|---|---|
| WO | WO 97/26366 | 7/1997 |
| WO | WO 99/11800 | 3/1999 |

OTHER PUBLICATIONS

International Search Report of PCT/JP98/03883 (three pages), date of actual completion of the international search: Nov. 24, 1998.

Bohlmann, J., et al., "Purification and cDNA cloning of anthranilate synthase from *Ruta graveolens*: modes of expression and properties of native and recombinant enzymes", *Plant J.*, 7(3):491–501 (1995).

Bohlmann, J., et al., "Anthranilate Synthase from *Ruta graveolens*", *Plant Physiol.*, 111:507–514 (1996).

Brotherton, J.E., et al., "Anthranilate synthase forms in plants and cultured cells of *Nicotiana tabacum* L.", *Planta*, 168:214–221 (1986).

Carlson J. E., et al., "Separation of Two Forms of Anthranilate Synthetase from 5–Methyltryptophan–Susceptible and –Resistant Cultured *Solanum tuberosum* Cells", *Physiol. Plant*. 44: 251–255 (1978).

Froissard, D. et al., "Structural organization of str 246C and str 246N, plant defense–related genes from *Nicotiana tabacum*", *Plant Mol. Biol.* 26(1):515–521 (1994).

Kang, K. K., et al., "Selection and Characterization of a 5–Methyltryptophan Resistant Mutant in *Zea mays* L.", *Euphytica*, 69:95–101 (1993).

Kreps, J. A., et al., "Molecular Basis of α–Methyltryptophan Resistance in amt–1, a Mutant of *Arabidopsis thaliana* with Altered Tryptophan Metabolism", *Plant Physiol.*, 110:1159–1165 (1996).

Kreps et al., "Isolation and Characterization of a Mutant of *Arabidopsis thaliana* Resistant to α–Methyltryptophan", *Plant Physiol*, 99: 269–275 (1992).

Lee, H. Y., et al., "Selection and Characterization of a Rice Mutant Resistant to 5–Methyltryptophan", *Theor Appl Genet*, 82: 405–408 (1991).

Li, J., et al., "The *Arabidopsis thaliana* trp5 Mutant Has a Feedback–Resistant Anthranilate Synthase and Elevated Soluble Tryptophan", *Plant Physiol.*, 110:51–59 (1996).

Niyogi, K.K., et al., "Two Anthranilate Synthase Genes in Arabidopsis: Defense–Related Regulation of the Tryptophan Pathway", *Plant Cell*, 4:721–733 (1992).

Ranch, J.P., et al., "Expression of 5–Methyltryptophan Resistance in Plants Regenerated from Resistant Cell Lines of *Datura innoxia*", *Plant Physiol.* , 71: 136–140 (1983).

Shillito, R. D. et al., "High Efficiency Direct Gene Transfer to Plants", *Bio/Tech.*, 3: 1099–1103 (1985).

(List continued on next page.)

*Primary Examiner*—Phuong T. Bui
*Assistant Examiner*—Medina A. Ibrahim
(74) *Attorney, Agent, or Firm*—Wean Khing Wong

(57) ABSTRACT

A 5-methyltryptophan resistant Nicotiana anthranilate synthase genes are disclosed, in particular the ASA2 gene of *Nicotiana tabacum*. Constructs containing the genes are also disclosed. This genes are useful for transforming plant cells and producing transformed plants and progenies which, compared to untransformed plant cells and plants, are more resistant to tryptophan analogs and/or produce increased levels of tryptophan. The transformed seeds are also disclosed. The genes are also useful as selectable markers. The amino acid sequence of ASA2, purified ASA2, and recombinant ASA2 are also disclosed.

18 Claims, 30 Drawing Sheets

OTHER PUBLICATIONS

Singh, B. K., et al., "Shikimate Pathway: Why Does It Mean So Much to So Many", *Oxford Surveys of Plant Molecular of Cell Biology*, 7: 143–185 (1991).

Sasse F. et al., "Site of Action of Growth Inhibitory Tryptophan Analogues in *Catharanthus roseus* Cell Suspension Cultures", *Z. Naturforsch*, 38 c:910–915 (1983).

Sato, S. et al., "Molecular Cloning and the Nucleotide Sequence of the *Clostridium themocellum trpE* Gene", *J. Biochem.* 105: 362–366 (1989).

Scott et al., "Characterization of a 5–Methyltryptophan Resistant Strain of *Catharanthus Roseus* Cultured Cells", *Phytochemistry*, 18: 795–798 (1979).

Song, H.–S., et al., "Cloning and Characterization of *Nicotiana Tabacum* Anthranilate Synthase Genes", Plant Physiology Meeting, Jul. 27–Aug. 2, Abstract 534, *Plant Physiol.*, 111 S: 125 (1996).

Song, H.–S., et al., "Session 19, Gene Structure/Characterization", Plant Physiology Meeting, Aug. 2–6, Abstract 128, *Plant Physiol.*, 114 S: 43(1997).

Stewart, Jr., C. N. et al., "Genetic Transformation, Recovery, and Characterization of Fertile Soybean Transgenic for a Synthetic *Bacillus thuringiensis cyrlAc* Gene", *Plant Physiol.*, 112: 121–129 (1996).

Tam et al., "Selection and Characterization of α–Methyltryptophan–Resistant Lines of *Lemna gibba* Showing a Rapid Rate of Indole–3–Acetic Acid Turnover", *Plant Physiol*, 107: 77–85 (1995).

Vain, P., et al, "Development of the Particle Flow Gun", *Plant Cell, Tissue, & Organ*, 33:237–246 (1993).

Vermeulen et al., "Agrobacterium mediated transfer of a mutant Arabidopsis acetolactate synthase gene confers resistance to chlorsulfuran in chicory (*Cichorium intylbus* L. )", *Plant Cell Reports*, 11: 243–247 (1992).

Wakasa, K. et al., "V. 2 Rice Mutants Resistant to Amino Acids and Amino Acid Analogs", in *Biotechnology in Agriculture and Forestry*, vol. 14 Rice, Y.P.S. Bajaj ed. (Springer–Verlag, New York, 304–315, 1991).

Widholm, J.M., "Tryptophan Biosynthesis in *Nicotiana Tabacum* and Daucus Carota Cell Culture, Site of Action of Inhibitory Tryptophan Analogs", *Biochimica et Biophysica Acta*, 261: 44–51 (1972).

Widholm, J.M., "Anthranilate Synthetase from 5–Methyltryptophan–Susceptible and –Resistant Cultured *Daucus Carota* Cells", *Biochimica et Biophysica Acta*, 279: 48–57 (1972).

Widholm, J.M., "Cultured Nicotiana Tabacum Cells with an Altered Anthranilate Synthetase Which is Less Sensitive to Feedback Inhibition", *Biochimica et Biophysica Acta*, 261: 52–58 (1972).

Widholm, J.M., "Relation between Auxin Autotrophy and Tryptophan Accumulation in Cultured Plant Cells", *Planta*, 134: 103–108 (1977).

Wildholm, J., "Differential Expression of Amino Acid Biosynthetic Control Iso–Enzymes in Plants and Cultured Cells", in *Plant Cell Culture: Results and Perspective*, Sala, F., et al., pp. 157–159 (1980).

Widholm, J. M., "In Vitro Selection with Plant Cell and Tissue Cultures: An Overview", *Iowa State J. Res.*, 62(4):587–597 (1988).

Song, H.–S., et al., "Tissue Culture–Specific Expression of a Naturally Occuring Tobacco Feedback —Insensitive Anthranilate Synthase", *Plant Physiol*, 117: 533–543 (1998).

* cited by examiner

Figure 4A

```
            1                                                             50
TASA1       ---------- ---------- ---------- ---------- ----------
TASA2       M--------- QSLPISYRLF PATHRKVL-- -PFAVISSRS STSALALRVR
RASA1       MIT-LNVETP P---LTRSQL PSTFRVSSAA ----SVNFND RVATSRWRPN
RASA2       MSAA--ATSM QSLKFSNRLV PP--SRRLSP VPNNVT--CN NLPKSAAPVR
AASA1       MSSSMNVATM QALTFSRRLL PSVASRYLSS SSVTVTGYSG RSSAYAPSFR
AASA2       MSA-VSISAV KSDFFTVEAI AVTHHRTPHP PHFPSLRFPL SLKSP--PAT
CTRPE       M--------- ---------- ---------- ---------- ----------

51                                                           100
TASA1       ---------- ---------- ---------- ---------- ----------
TASA2       TLQCRC---- LH-------- ---------- -------SS SLVMDEDRFI
RASA1       SLSLTTSS-- ---Y--RLRTL KCAASASTSA STSASPSPSP SLVDQSANFH
RASA2       TVKCCASS-- ---WNSTING AAATTNGASA ASNGASTTTT TYVSDATRFI
AASA1       SIKCVSVS-- ---PEASI-- ---------- ---------- --VSDTKKLA
AASA2       SLNLVAGSKL LHFSRRLPSI KCSYTPSLDL SE-------- ---EQFTKFK
CTRPE       ---------- --FYPTLDEV KIM------- ---------- ----------

101                                              ****        150
TASA1       ---------- ---------- ---------- --DDREAPSF LFESVEPGSQ
TASA2       EASKSGNLIP LHKTIFSDHL TPVLAYRCLV KEDDREAPSF LFESVEPGFR
RASA1       EASKKGNLIP LYRCIFSDHL TPVLAYRCLV KEDDRDAPSF LFESVEPGSQ
RASA2       DSSKRANLVP LYRCIFADHL TPVLAYRCLV QEDDKETPSF LFESVEPG-R
AASA1       DASKSTNLIP IYRCIFSDQL TPVLAYRCLV KEDDREAPSF LFESVEPGSQ
AASA2       KASEKGNLVP LFRCVFSDHL TPILAYRCLV KEDDRDAPSF LFESVEPGSQ
CTRPE       --AKDYNIIP VTMEVYADME TPI----SLF KRFEESSCCF LLESVEGGEK
                                                  .    ** .**** *  .

151         *                                               200
TASA1       MSSVGRYSVV GAQPAMEIVA KENKVIVMDH NNETMSEEFV EDPMEIPRKI
TASA2       GSSVGRYSVV GAQPSMEIVA KEHNVTILDH HTGKLTQKTV QDPMTIPRSI
RASA1       ASSIGRYSVV GAQPAIEIVA KENMVTILDH EGGQRTEQFV EDPMDVPRRI
RASA2       ISTVGRYSVV GAHPVMEVIA KDNMVTVMDH EKGSLVEEVV DDDPMEIPRRI
AASA1       MSSVGRYSVV GAQPAMEIVA KENKVIVMDH NNETMTEEFV EDPMEIPRKI
AASA2       SSNIGRYSVV GAQPTIEIVA KGNVVTVMDH GASLRTEEEV DDPMMVPQKI
CTRPE       W---ARYSII GKNPFLVVES YKNKTIIRER NGSQREVE-- GNPVEIIKGI
             .***.. *  *  . .     . ..       . . .              .*. . . *
                                                                        +
            201                                                         250
TASA1       SEKWNPDPQL VQDLPDAFCG GWVGFFSYDT VRYVEKRKLP FSKAPEDDRN
TASA2       SEGWKP--RL IDELPDTFCG GWVGYFSYDT VRYVENRKLP FLRAPEDDRN
RASA1       MEGWK--PQL IDELPEAFCG GWVGYFSYDT VRYVEKKKLP FFSAPTDDRN
RASA2       SEDWK--PQI IDDLPEAFCG GWVGFFSYDT VRYVEKKKLP FSKAPQDDRN
AASA1       SEKWNPDPQL VQDLPDAFCG GWVGFFSYDT VRYVEKRKLP FSKAPEDDRN
AASA2       MEEWN--PQG IDELPEAFCG GWVGYFSYDT VRYVEKKKLP FSNAPEDDRS
CTRPE       MGKFKGAN-- LPNLPR-FNG GAVGYFGYDL IRHYEN--LP --NVPEDDMG
              .         .** * * ***.*.**   .* *.  **       * **

251                                                         300
TASA1       LPDMHLGLYD DVVVFDHVEK KAYVIHWIRL DGSLPYEKAY SNGMQHLENL
TASA2       LADIQLGLYE DVIVFDHVEK KAHVIHWVQL DQYSSLPEAY LDGKKRLEIL
RASA1       LPDVHLGLYD DVIVFDHVEK KAFVIHWVRL DQYSSVAEAY NDGMNRLENL
RASA2       LADMHLGLYN DVIVFDHVEK KVYVIHWVRL NQQSSEEKAY AEGLEHLERL
AASA1       LPDMHLGLYD DVVVFDHVEK KAYVIHWIRL DGSLPYEKAY SNGMQHLENL
AASA2       LPDVNLGLYD DVIVFDHVEK KAYVIHWVRI DKDRSVEENF REGMNRLESL
CTRPE       LPECHFMFTD EVLVYDHLKQ KIHII--VNL HVNGNIERAY ISAVDRIKTI
             *..  .  .   .*.**.  .* .*                 .      .  ..
```

Figure 4B

```
       301                                                          350
TASA1  VAKLHDIEPP KLAAGNVNLQ TRQFGPSLDN SNVTCEEYKE AVVKAKEHIL
TASA2  VSRVQGIESP RLSPGSVDFC THAFGPSLTK GNMTSEEYKN AVLQAKEHIA
RASA1  VSRVHDIVPP KLRSGSIKLH TRHFGPKLER SSMTSEAYKE AVLEAKEHIL
RASA2  VSRVQDENTP RLAPGSIDLH TGHFGPPLKK SNMTCEEYKM AVLAAKEHIQ
AASA1  VAKLHDIEPP KLAAGNVNLQ TRQFGPSLDN SNVTCEEYKE AVVKAKEHIL
AASA2  TSRIQDQKPP KMPTGFIKLR TQLFGPKLEK STMTSEAYKE AVVEAKEHIL
CTRPE  HREILDTRWK TADNSVLSYN KKKNELAVT- SNISKEDFCR NVLKAKQYIR
         . .         . .                 . ...* .  *. **. *
                                                            *
       351              +                 **    **        400
TASA1  AGDIFQIVLS QRFERRTFAD PFEVYRALRV VNPSPYMGYL QARGCILVAS
TASA2  AGDIFQIVLS QRFERRTFAD PFEVYRALRI VNPSPYMTYI QARGCILVAS
RASA1  AGDIFQIVLS QRFERRTFAD PFEIYRSLRI VNPSPYMTYL QARGCILVAS
RASA2  AGDIFQIVLS QRFERRTFAD PFEVYRALRV VNPSPYMTYM QARGCVLVAS
AASA1  AGDIFQIVLS QRFERRTFAD PFEVYRALRV VNPSPYMGYL QARGCILVAS
AASA2  AGDIFQIVLS QRFERRTFAD PFEIYRALRI VNPSPYMAYL QVRGCILVAS
CTRPE  DGDIFQVVLS QRLCVETNEN PFNIYRALRV INPSPYMYYL KFGGYRIIGS
       *****.*** **.    *  . **..**.**. .****** *. .  * ...*

401                                                          450
TASA1  SPEILTKVKQ NKIVNRPLAG TSKRGKNEVE DKRLEXELLE NEKQSAEHIM
TASA2  SPEILTRVKK RRIVNRPLAG TSRRGKTPDE DVMLEMQMLK DEKQRAEHIM
RASA1  SPEILTRVKK RKITNRPLAG TIRRGKTRKE DLVFEKELLN DEKQCAEHIM
RASA2  SPEILTRVKK NKIVNRPLAG TARRGRTTEE DEMLETQLLK DAKQCAEHVM
AASA1  SPEILTKVKQ NKIVNRPLAG TSKRGKNEVE DKRLEKELLE NEKQCAEHIM
AASA2  SPEILLRSKN RKITNRPLAG TVRRGKTPKE DLMLEKELLS DEKQCAEHIM
CTRPE  SPEMLVRVEN GIVETCPIAG TRKRGRTKEE DEALEKELLS DEKEIAEHVM
       ***.*  .       .  *.** * .**.   * *  .* ..*  . *. ***.*

451                                                          500
TASA1  LVELGRNDVG KVTKYGSVKV EKLMNIERYS HVMHISSTVT GELQDGLTCW
TASA2  LVDLGRNDVG KVSKPGSVNV EKLMSVERYS HVMHISSTVS GELLDHLTCW
RASA1  LVDLGRNDVG KVSEPGSVKV EKLMNIEHYS HVMHISSTVT GELLDHLTSW
RASA2  LVDLGRNDVG KVSKSGSVKV EKLMNVERYS HVMHISSTVT GELQDNLSCW
AASA1  LVDLGRNDVG KVTKYGSVKV EKLMNIERYS HVMHISSTVT GELQDGLTCW
AASA2  LVDLGRNDVG KVSKPGSVEV KKLKDIEWFS HVMHISSTVV GELLDHLTSW
CTRPE  LVDLGRNDIG RVSKFGTVAV KNLMHIERYS HVMHVVTNVQ GEIREDKTPF
       **.***** *.*.  *.* *   .*  .* .*  ****. . *  **. . . .

501                                                          550
TASA1  DVLRAALPVG TVSGAPKVKA MELIDELEPT RRGPYSGGFG GVSFTGDMDI
TASA2  DALRAALPVG TVSGAPKVKA MELIDQLEVA RRGPYSGGFG GISFSGDMDI
RASA1  DALRAALPVG TVSGAPKVKA MEIIDKLEVT RRGPYGGGFG GISFTGDLDI
RASA2  DALRAALPVG TVSGAPKVKA MELIDELEVN RRGPYSGGFG GISFTGDMDI
AASA1  DVLRAALPVG TVSGAPKVKA MELIDELEPT RRGPYSGGFG GVSFTGDMDI
AASA2  DALRAVLPVG TVSGAPKVKA MELIDELEVT RRGPYSGGFG GISFNGDMDI
CTRPE  DALMSILPAG TLSGAPKVRA MEIIDELETV KRGPYGGAIG YLSFNGNLDS
       * *   **  *.******.* **.** **    .****.*..*  .** *..*

551                                                          600
TASA1  ALSLRTIVFP TACQYNTMYS YKDANKRREW VAYLQAGAGV VADSDPQDEH
TASA2  ALALRTMVFL NGARYDTMYS YTDASKRQEW VAHLQSGAGI VADSNPDEEQ
RASA1  ALALRTMVFQ TATRYDTMYS YKDVDKRREW IAHLQAGAGI VADSDPADEQ
RASA2  ALALRTIVFQ TGTRYDTMYS YKNATKRRQW VAYLQAGAGI VADSDPDDEH
AASA1  ALSLRTIVFP TACQYNTMYS YKDANKRREW VAYLQAGAGV VADSDPQDEH
AASA2  ALALRTMVFP TNTRYDTLYS YKHPQRRREW IAHIQAGAGI VADSNPDDEH
```

Figure 4B (continued)

```
       451
TASA1  LVELGRNDVG KVTKYGSVKV EKLMNIERYS HVMHISSTVT GELQDGLTCW
TASA2  LVDLGRNDVG KVSKPGSVNV EKLMSVERYS HVMHISSTVS GELLDHLTCW
RASA1  LVDLGRNDVG KVSEPGSVKV EKLMNIEHYS HVMHISSTVT GELLDHLTSW
RASA2  LVDLGRNDVG KVSKSGSVKV EKLMNVERYS HVMHISSTVT GELQDNLSCW
AASA1  LVDLGRNDVG KVTKYGSVKV EKLMNIERYS HVMHISSTVT GELQDGLTCW
AASA2  LVDLGRNDVG KVSKPGSVEV KKLKDIEWFS HVMHISSTVV GELLDHLTSW
CTRPE  LVDLGRNDIG RVSKFGTVAV KNLMHIERYS HVMHVVTNVQ GEIREDKTPF
       **.******.  *.      *      ***. ****      .
                                                            500

501
TASA1  DVLRAALPVG TVSGAPKVKA MELIDELEPT RRGPYSGGFG GVSFTGDMDI
TASA2  DALRAALPVG TVSGAPKVKA MELIDQLEVA RRGPYSGGFG GISFSGDMDI
RASA1  DALRAALPVG TVSGAPKVKA MEIIDKLEVT RRGPYGGGFG GISFTGDLDI
RASA2  DALRAALPVG TVSGAPKVKA MELIDELEVN RRGPYSGGFG GISFTGDMDI
AASA1  DVLRAALPVG TVSGAPKVKA MELIDELEPT RRGPYSGGFG GISFTGDMDI
AASA2  DALRAVLPVG TVSGAPKVKA MELIDELEVT RRGPYSGGFG GVSFTGDMDI
CTRPE  DALMSILPAG TLSGAPKVRA MEIIDELETV KRGPYGGAIG YLSFNGNLDS
       * *   **.* *.*******  **.*.**    .***.*..   .*.*..*.
                                                            550

551
TASA1  ALSLRTIVFP TACQYNTMYS YKDANKRREW VAYLQAGAGV VADSDPQDEH
TASA2  ALALRTMVFL NGARYDTMYS YTDASKRQEW VAHLQSGAGI VADSNPDEEQ
RASA1  ALALRTMVFQ TATRYDTMYS YKDVDKRREW IAHLQAGAGI VADSDPADEQ
RASA2  ALALRTIVFQ TGTRYDTMYS YKNATKRRQW VAYLQAGAGI VADSDPDDEH
AASA1  ALSLRTIVFP TACQYNTMYS YKDANKRREW VAYLQAGAGV VADSDPQDEH
AASA2  ALALRTMVFP TNTRYDTLYS YKHPQRRREW IAHIQAGAGI VADSNPDDEH
                                                            600
```

Figure 4C

```
CTRPE   CITIRTIILK DGKAY----- ---------- ---------- ---VQAGAGI VADSVPEREY
        ..*..      *                                    *.****    *****  *

601                                                             650
TASA1   CECQNKAAGL ARAIDLAESA FVKKX----- ---------- ---------- ----------
TASA2   IECENKVAGL CRAIDLAESA FVKGRHKPSV KINGSVPNLF SRVQRQTSVM ----------
RASA1   RECENKAAAL ARAIDLAESS FIEK------ ---------- ---------- ----------
RASA2   RECQNKAAGL ARAIDLAESA FVNKSSS--- ---------- ---------- ----------
AASA1   CECQNKAAGL ARAIDLAESA FVKK------ ---------- ---------- ----------
AASA2   RECENKAAAL ARAIDLAESS FLEAPEFTTI TPHINNI--- ---------- ----------
CTRPE   EECYNKAMAL LKAIEEAGEI R--------- ---------- ---------- ----------
        ** ** .**  .*........

651
TASA1   ----------
TASA2   ----------
RASA1   SKDRVHEKRNX
RASA2   ----------
AASA1   ----------
AASA2   ----------
CTRPE   ----------
```

Figure 5
A. Vector ASA2
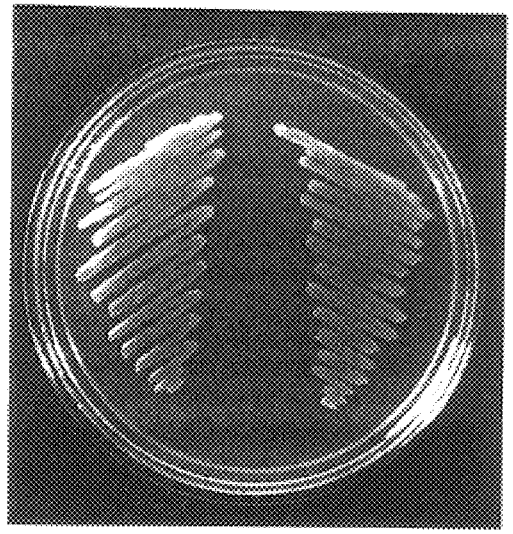
+Trp
B. Vector ASA2
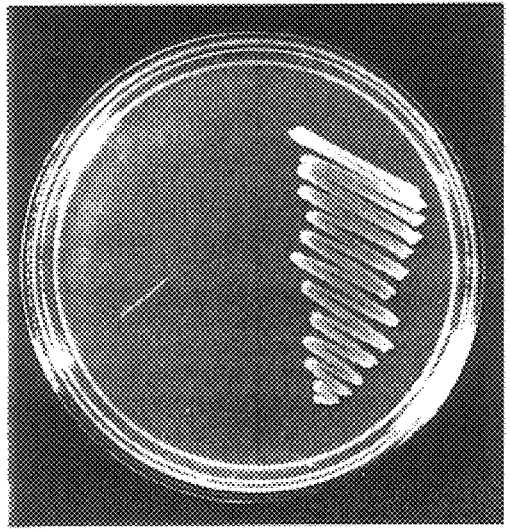
-Trp
C. Vector ASA2
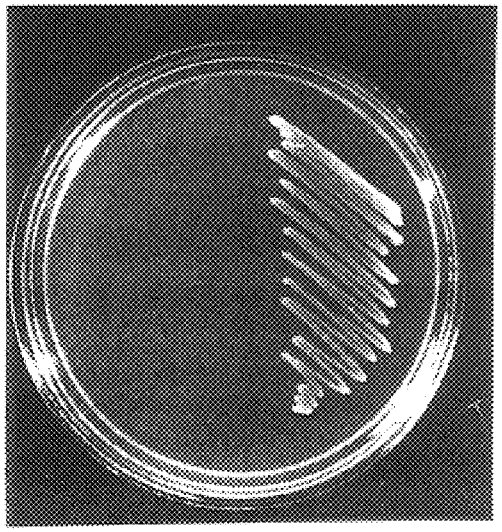
-Trp/5MT

Figure 9

```
-2287  CTAGTTATGG ATGAGGACAG GTTCATTGAA GCTTCAAATC TATTCGATAG
-2237  TGGGACCTAC GTCTCAAATC CCGAAAAAAC TCGCGAAATC CGAACACCCG
-2187  TTCCGCTACG AGTTCAACCA TACAAAAATT ATCCAATTCT GATGTCAACT
-2137  CGACCCTCAA ATCTTCAATT AAAGTCTTTG AAGACTTCTA TCATTTCAA
-2087  CTCAATCTTT ATCCCATTTG AACTAAACAC TATTTCCATA AAACCTTATT
-2037  GATACGTATA AATAATACTC TTACACCCAA GAATTATACT CTTAATCACC
-1987  CATCATTACC CAAACTCGGA ATTGAAGATT AAAACCTTAC CTCTTTGATG
-1937  AAGAACTTGA GGGATTTTTT TGTTGGATTT CAAGGCTTGG ACAAGAATTT
-1887  GATGAGCAAG ACACTTTATC TACTTCCTCT CTCTAGAACA CTCTCACTTC
-1837  TCTCTAAAAT CATCAGATAG TTGCCCCAAA ACCTATTTAT CAAAATAGAG
-1787  TCGGGTAATG AAAATAGGTA AATGGACCCT CCAAACTCAG GTATGCGATT
-1737  GCACAATGGA TATACGGGTC GCACAATGGA CCACCAAATC GATGCCGAAA
-1687  ACTGGGTTGC GCTGGACAGG TCTGCGACCC ATTTTACGGT CGCACAATGT
-1637  GCTACGAAGA GGAATTCACA TAGATTTAGG AAGGGCCTGT TGTATTTGTG
-1587  TACAAGCTAA AGTTTTTGA AAAACAAATA CCTTTGGTCA CTTTCATTGT
-1537  CAAATAGGTT TTTCCTTCGT ATACCTTACT TACATCACAT AGTGATTATG
-1487  CGATCGCACA ATTTACCGCA TAATCGTATT TTTCCAGCTT TTGGTAATTT
-1437  AATCATAACT TTTTTATGA ATATCCAAAT GACGAACTGT TTGAAGCGTT
-1387  AGAAACTAGA CTCAAGATC TTTCATTTTA TAGGCAATAC GGCACATAAT
-1337  ATTTTGTATC ATGAGAGTTA TTCTCATTTG AAGTTAGGTC TTGTGTGAAC
-1287  TCACTTGAAA CTTTAGTCTT ATGAAATTTC CAACTTCTAC ATCCGATTCC
-1237  GAAACCTATC GAATCAAGTC CGATTGACCT CAAATTTTGC ATACAAGCCA
-1187  TAAATGACAT AACAGAGCTA TAAAATTTTT CGAAACGGGA TTCCGGCTCC
-1137  GATATCAAAA AGTCAACCCT GTGGTCAAAC TTGGAAATCT TTAGCCTTTA
-1087  AATTACTAGT TTCCGTTAAA TGGTCATAAC TTGAGTTATG GACCTCCAAA
-1037  TTAAATTCCG GGCATACGCC CAAGTCCCAT ATCACGATAC GAACCTATAG
-987   GAACTTTCAA AATATTGATC CGGATCCGTT TGCTCAAAAT GTTGATCAAA
-937   GTCAACTCAG TTGAGTTTTA AGGCTCTAGT TCACATTTTA ATCCATTTTC
-887   ACCTAAAAAC TTTCCGGAAA ATTTTACGGA TTTCGCACGC AAGTCGATGA
-837   ATGACTTTTG GAGGTCTTAG AACACGTAAT TAATTATTAA ATTTAAAGAT
-787   GACATTTTGG ATAATCACCC AAGTAGTACA AATTTTTTAT GCGGTGATTA
-737   TATTTGCCAA TCCATCAAGC CAAACATGTC GTAATTAGTC ATAAATTAAG
-687   TTATACAGGA AGAATAATAC GAGAAATATA ATACCTAAAT TAATAAATAC
-637   TACTATAAAA TTATAATATT GATATTGTGG TTGTATTGCC CATTTCATTA
-587   GAAAGGATAT ATGATGTATA ATATAAAATT TTACAATGTT ATTCTTGTTT
-537   TTAAAGTTAA TAAAAATTTA AAATATGAAT TTAAGGTTAT TCTTGTTTAT
-487   AGATTCTTTA TATCATAAAG CTAATCCTCG TATAAATTAT TTCATATTCG
-437   ACTCATATAA ACTAATACTG AAATTACTAT ATAAGATTAT ATACCGGTAT
-387   ATATTGGAAA CGAGACATCA GCCAAATGTG TCCAAAAATA ATAAATATCA
-337   AATTTTATAT CAGGATTATT TTTTTGATT ATGTTAACAA AGTTAAAAGT
-287   ATCAGACTAT AAATACTGTA GATAAGATCA GCCATTATTA GAGATAATAC
-237   TCTCACTACC TATATTGAAA GTGAAGTAGA CATTTTCTGA GGTGGAATAT
-187   TTAAACGTT TTCAGACATT TAAACCTGG AATGCGGAGG CAAAGTAGTG
-137   TAGTACTTAC TAGTAGTATA AATAAGTGAT CCCATTTTCA AAGTCACCGT
-87    CAAAAATCCC CATTTCACCG TTTCCTCGTT TCTCCTCCTC ACTAATTTTG
-37    TCTCTTTCTC TTGGTTTGCT ATTGTGCTCT TGTAGGA    ATG CAGTCGT
                                                    -1
```

Figure 10
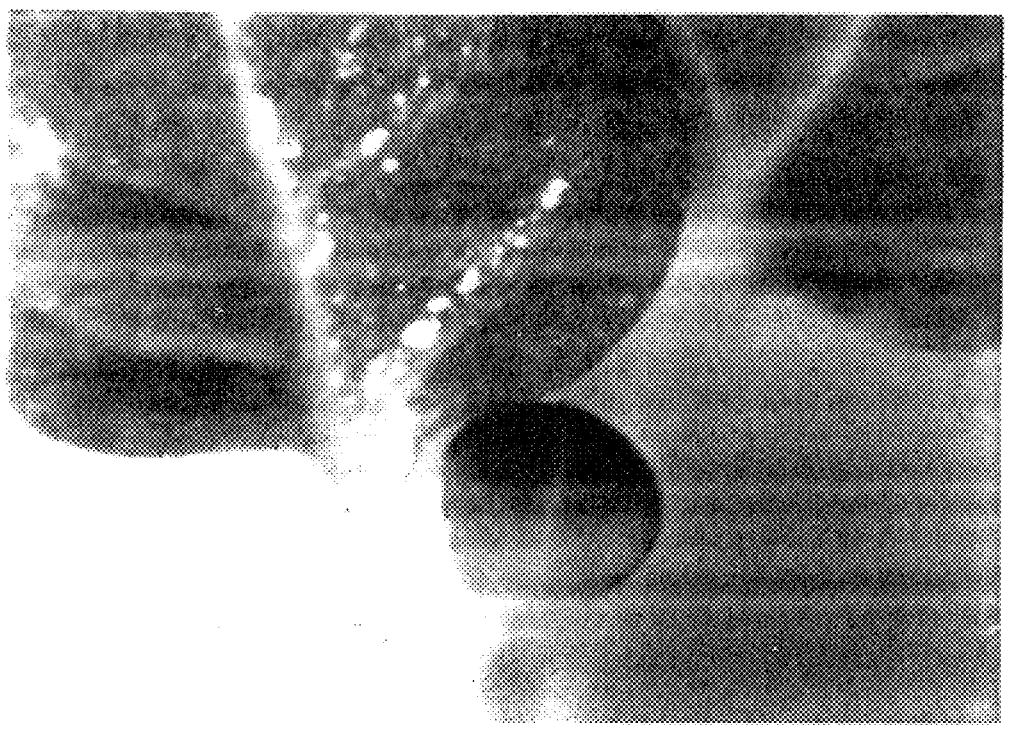
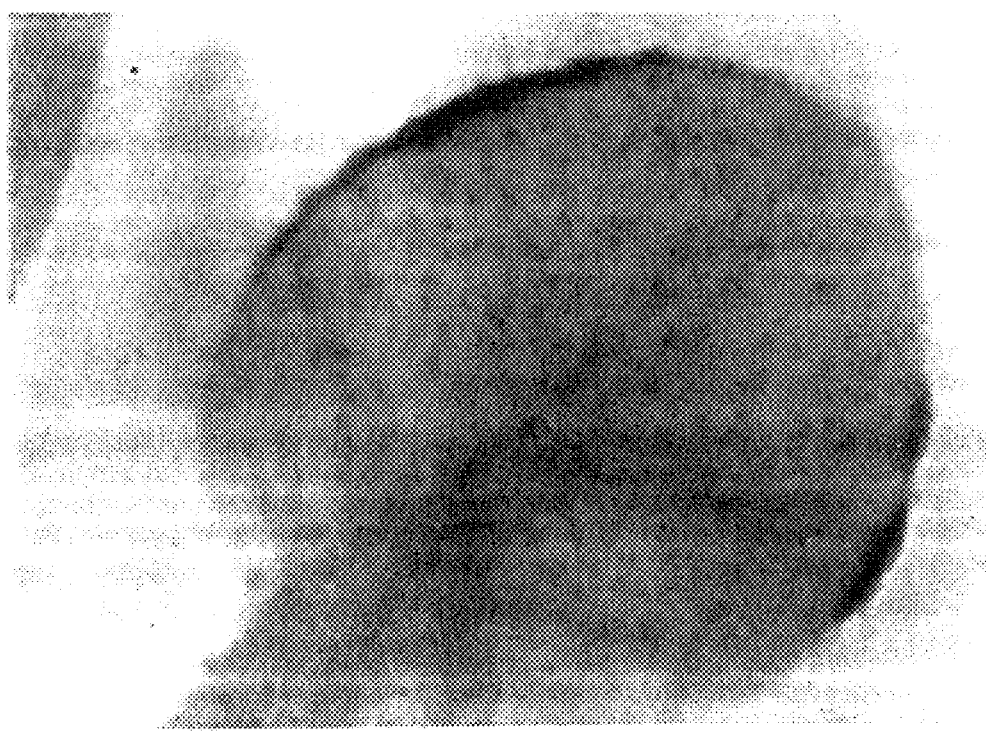

Figure 15A

```
              1                                                                      50
ASA2G         AGGACGAAAT GATGTAGGAA AGGTTTATTA CTGACCATTT CAGCATTTTT
ASA3G         AGGACGAAAT GATGTAGGAA AGGTTTATTA CTGACCATTC CAGAATTTTT
              ********** ********** ********** ********   ***  ******
              51                                                                    100
ASA2G         GCATCACCAA GAGCTTTGAA ATATATCTGG TTCAATGAGT GGGAGAGAAC
ASA3G         GCATCACCAA GAGCTTTAAT ATATATCTTG TTCAATGAGT GGCAGAGAGC
              ********** *******  * *******  * ********** **  ***** *
              101                                                                   150
ASA2G         CTTGTTTGGT AGAAAATTAG AAATGGAAAT ACTAAAAATA TTAACTGCTT
ASA3G         CTTGCTTGGT AAAAAATTAG AAATAGAAAT ACTAAAATTA TTAACTGCTT
              ****  **** *  ******* ****  ***** ******  **  **********
              151                                                                   200
ASA2G         CCTTTTTCCG CCCATCTTTT TCATGAAATG CTAATATAGA GGGTGTCATG
ASA3G         CCTTTTTCTG CCCATTTTTT TCATGAAATG CTAACATAGA GGGTGTCATG
              ********  * *****  **** ********** ****  ***** **********
              201                                                                   250
ASA2G         CAGCATGCAT TATCTACTTC TACTACCCTC TTTTACATTT TAGCCATATA
ASA3G         CAGCATGAAT CATCTGCTTC TGCTACACTC TTTAACATTT TAGCCATACA
              *******  ** ****  **** *  **** *** ***  ****** ******** *
              251                                                                   300
ASA2G         AAATGCAATG GCC.ACCCCC CTAACCTTTC CTGTTAGTTG TTACCTCTCT
ASA3G         AAATGCAATG TCCGTCCCCC TTATTCTTTC CTGTTAGTTG TTACCTCTCT
              ********** ***  *****  **  ***** ********** **********
              301                                                                   350
ASA2G         GCTATACAG TGTTAGTATC TTCTGTTCCA CGATATACTT CAGGTAGAGC
ASA3G         TCTATGACAG TGTGAGTATC TTCTGTTCCA CAATATACTT CAGGTAGAGC
               ****  **** ***  ***** ********** *  ******* **********
              351                                                                   400
ASA2G         CTTTTCCAAC AGTGATAGAA CCCCTAGACG TTGGTTGTTT TATGTAAATA
ASA3G         CCTTTCAAC TGTGATAGAA CCCCTCGGCG TTGGTTGTTT CATGTAAATA
              *  *** **** ********* *****  *  ** **********  *********
              401                                                                   450
ASA2G         CAGCAACTAA ACTTATGGGG TGCCTCTTTT CTTGTTTCCT GAATATGTTT
ASA3G         CAACAACTGA ACTT...GGC TGCCTCTTTT TTTGTTTCCT GAATATGTTT
              **  ***** * ****   ** ********** ********* **********
              451                                                                   500
ASA2G         CGACTTGCAC TTGAAAAATA TTTTGGGTTA CCCAACTATT TCCTTTTCTT
ASA3G         TGACTTGCAC TTGAAAAATA CATT.GGTTA CCCAAATATT TCCTTTTCTT
               ********* **********  * ***** ******  **** **********
              501                                                                   550
ASA2G         GCTATAGGTG TCAAAACCTG GTTCTGTGAA TGTCGAAAAG CTCATGAGCG
ASA3G         GCTATAGGTG TCAAAACCTG GCTCTGTGAA TGTTGAAAAG CTCATGAGCG
              ********** **********   ******** ***  *****  **********
              551                                                                   600
ASA2G         TTGAGCGGTA TTCCCATGTG ATGCACATAA GCTCCACGGC GAGTCCATAT
```

Figure 15B

```
ASA3G   TCGAGCGGTA TTCCCATGTG ATGCACATAA GCTCCACGGC GAGTCCATAT
        ********** ********** ********** ********** **********
        601                                                 650

ASA2G   TTTGATTTCA TCCGAGGTTG TACTGGAATC TTAAATTGCC TTTGATATTC
ASA3G   TTTGATTTCG TCCGAGGTCA TACTGGAATC TAAATTGCCT TTTGATGTTC
        ********** ********** ********** * ******* * ** ** ***
        651                                                 670

ASA2G   TTGTGGG... .......... ..........
ASA3G   TTTGTTGGCT CTAATTTCC
        **  *
```

5MT resistance of *A.sinicus* hairy roots transformed with 35S-ASA2 gene

5MT resistance of *A.sinicus* hairy roots transformed with 35S-ASA2 gene

5MT resistance of soybean hairy roots transformed with *35S-ASA2* gene

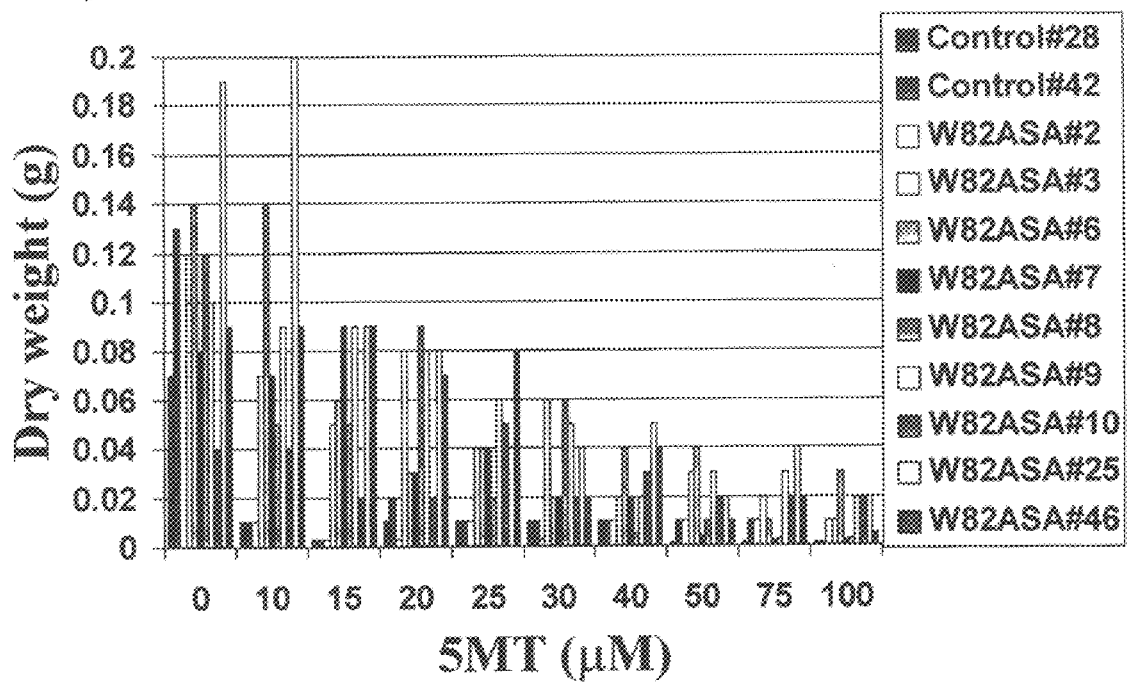
5MT resistance of soybean hairy roots transformed with *35S-ASA2* gene

NUCLEOTIDE SEQUENCES ENCODING ANTHRANILATE SYNTHASE

This application is a continuation-in-part of U.S. patent application, Ser. No. 09/001,826, of the same title, filed on Dec. 31, 1997 now U.S. Pat. No. 5,965,727, which in turn is a continuation-in-part of U.S. patent application, Ser. No. 08/937,739, now abandoned of the same title, filed on Jul. 25, 1997, which in turn is based on U.S. provisional application Ser. No. 60/025,140, of the same title, filed on Jul. 26, 1996.

TECHNICAL FIELD OF THE INVENTION

The present invention relates to the field of plant genetics. In particular, the invention provides novel selectable markers and promoters for plants.

BACKGROUND OF THE INVENTION

The selection of mutants using cultured plant cells is in principle similar to that done with microorganisms, but in practice is much more difficult. The reasons for the difficulties include the usual clumpy nature of plant cell cultures; single cells or protoplasts usually cannot be easily grown to form clones, cell growth is slow and the cells are usually not monoploid. Despite these problems a large number of successful selection experiments have been carried out to produce mutants of value for producing compounds, for biochemical and molecular biology studies, for markers in genetic experiments and for improving crop plants. Part of the reason for the success is that cell systems allow the screening of millions of cells for the desired trait.

Whether the selected phenotype is under genetic or epigenetic control can most easily be determined by regenerating plants and by following the phenotype in progeny. Genetically controlled phenotypes would be inherited by progeny and would generally be more stable at the cell level in comparison to epigenetically controlled traits. A large number of in vitro selected traits have been shown to be expressed in regenerated plants and to be passed on to progeny.

There are several types of in vitro selection that can be used to obtain cells containing the trait of interest (J. Widholm, *Iowa State J. of Research*, 62: 587–597, 1988). These include selection for growth, selection for valuable compound production, auxotroph selection and resistance selection. Selection for resistance should be the easiest kind of selection to accomplish and from the number of reports in the literature this would appear to be true.

The selection for amino acid analog resistance in plants has been pursued for a number of years. A primary focus of this research has been directed to the enzyme anthranilate synthase (AS). AS catalyzes the conversion of chorismate into anthranilate, the first reaction leading from the common aromatic amino acid (shikimate),pathway toward the biosynthesis of tryptophan (Trp). As a branchpoint enzyme in the synthesis of aromatic amino acids, AS plays a key role in the diversion of chorismate into Trp and indolic secondary compound biosynthesis.

Available information indicates that AS plays a key role in regulation of Trp biosynthesis. In plants, bacteria, and fungi, AS activity is regulated by Trp feedback inhibition (Matsui et al., *J. Bacteriol*, 169: 5330–5332, 1987). In microbes, AS usually consists of two nonidentical subunits, referred to as the alpha subunit (component I) and the beta subunit (component II). component I can convert chorismate to anthranilate in the presence of high levels of ammonia (ammonia-dependent AS activity), whereas-component II is responsible for the use of glutamine (hereinafter referred to as "Gln") as the amino donor (Hutter et al., *Annu Rev Microbiol*, 40: 55–77, 1986).

As a means to investigate regulation of the Trp pathway, toxic analogs of Trp have been used in metabolic studies of plant cell cultures and as a tool to select mutants. Many of these studies have been conducted with the growth inhibitor 5-methyltryptophan (5MT). In a number of species including Datura innoxia (hereinafter referred to as *D. innoxia*), Catharanthus roseus, and Solanum tuberosum, variant cell lines resistant to inhibitory concentrations of 5MT were found to have AS that was less sensitive to feedback inhibition by Trp (Carlson and Widholm, *Physiol Plant*, 44: 251–255, 1978; Scott et al., *Phytochemistry*, 18: 795–798, 1979; Ranch et al., *Plant Physiol*, 71: 136–140, 1983). Widholm (*Planta*, 134: 103–108, 1977) described 5MT-resistant carrot cell lines and a potato cell line that were auxin autotrophic.

In addition, 5-methylanthranilate was successfully used to isolate plant auxotrophic mutants defective in three different genes, trp1, trp2, and trp3 (Last and Fink, Science, 240: 305–310, 1988; Last et al., *Plant Cell*, 3: 345–358, 1991) and mutants of *Chlamydomonas reinhardtii* (Dutcher et al., *Genetics*, 131: 593–607, 1992). Mutants resistant to 5MT or alpha-methyltryptophan (αMT) were reported in *Arabidopsis thaliana* (hereinafter referred to as *A. thaliana*) (Koornneef and van Loenen Martinet, *Arabidopsis Inf Serv*, 20: 104–108, 1983; Kreps & Town, *Plant Physiol*, 99: 269–275, 1992), maize (Kang & Kameya, *Euphytica*, 69: 95–101, 1993), *Lemna gibba* (Tam et al., *Plant Physiol*, 107: 77–85, 1995) and *Oryza sativa* (Lee & Kameya, *Theor Appl Genet*, 82: 405–408, 1991). The specificity of selection with these analogs have not been systematically investigated.

A feedback-insensitive AS gene (ASA1 mutant) has been recently obtained by selection of mutagenized Arabidopsis seeds resistant to 6-methylanthranilate (Li & Last, *Plant Physiol.*, 110: 51–59, 1996). In addition, αMT resistance led to identification of a mutant in *A. thaliana* with the same amino acid change (Kreps et al., *Plant Physiol.*, 110: 1159–1165, 1996).

One method for the production of trahsgenic plants is to transform plant cells in tissue culture with a plasmid containing a promoter and selectable marker which also contains a gene ("desirable gene") which would express the desired trait in the regenerated plant. Thus when one selects cells transformed with the selectable marker, many of these cells will also carry the desirable gene that will also be expressed to produce the desired result such as insect resistance, disease resistance, herbicide resistance, changed. starch, drought tolerance, etc. An example is where the nptII (neo) gene is driven by a constitutive promoter, nosP (Vermeulen et al., Plant. *Cell Reports*, 11: 243–247, 1992). Next to this selectable marker gene is a mutant acetolactate synthase gene with its own promoter. This latter gene makes the regenerated plants resistant to certain herbicides.

An AS gene which encodes an enzyme that is highly resistant to an amino acid analog, such as 5MT, would be an ideal selectable marker for the production of transgenic plants as described above. Especially if the promoter which regulates the expression of this enzyme provided for high level expression of the enzyme in tissue culture, and little or no expression in regenerated plants. There has been considerable environmental concern because most selectable markers are constitutively expressed in all tissues of the plant and are not of plant origin. The former concern would be reduced by using such a tissue culture specific promoter while the latter concern would be eliminated by using the plant-derived AS gene as the selectable marker. In fact, the use of a tissue culture specific promoter would even allow one to use selectable markers that are not of plant origin. Traditional selectable markers that are not of plant origin include nptII, which encodes kanamycin resistance.

BRIEF SUMMARY OF THE INVENTION

A first aspect of the present invention is an isolated deoxyribonucleic acid (DNA) molecule comprising a DNA sequence (SEQ ID NO: 4), the ASA2 gene of *Nicotiana tabacum* (hereinafter referred to as *N. tabacum*), and fragments thereof, which encode a feedback-insensitive form of AS. The ASA2 gene product could function as a selectable marker for transforming plant cells.

A second aspect of the present invention is an isolated DNA molecule comprising a DNA promoter sequence, the ASA2 promoter sequence (SEQ ID NO: 14), which is capable of directing tissue culture specific transcription of a downstream structural gene in a plant cell. The functional promoter sequence may be selected from the group consisting of the tobacco ASA2 promoter and DNA sequences which are at least 70 percent homologous to a fragment of the tobacco ASA2 promoter which is from about 150 to about 606, more preferably from about 150 to about 370, and most preferably about 150 bases in length. For constitutive expression of the promoter, the fragment is preferably a fragment taken from between about −606 to about −1 of the nucleotide sequence of the ASA2 promoter. For a functional promoter, the fragment preferably includes the −151 to −214 nucleotide sequence of the ASA2 promoter.

The tissue culture specific expression promoter sequence may be selected from the group consisting of the tobacco ASA2 promoter and DNA sequences which are at least 70 percent homologous to a fragment of the tobacco ASA2 promoter capable of directing tissue culture specific expression. The fragment is preferably between about 30 to about 100, more preferably 5 between about 30 to about 49, and most preferably about 30, bases in length. This fragment is preferably a fragment taken from between about −2252 to about −607 nucleotide sequence of the ASA2 promoter.

A third aspect of the present invention is a DNA construct comprising an expression cassette, which construct comprises, in the 5' to 3' direction, an ASA2 promoter and a structural gene positioned downstream from the promoter and operatively associated therewith.

A fourth aspect of the present invention is an isolated DNA promoter sequence (included in SEQ ID NO: 14) derived by removing a portion of the ASA2 promoter, which is capable of directing high level constitutive transcription of a downstream structural gene in plant tissues. The promoter sequence may be selected from the group consisting of the tobacco ASA2 promoter and DNA sequences which are at least 70 percent homologous to a 606 or smaller fragment of the tobacco ASA2 promoter capable of directing constitutive expression.

A fifth aspect of the present invention is a DNA construct comprising an expression cassette, which construct comprises, in the 5' to 3' direction, the truncated ASA2 promoter (such as the promoter described in the second and fourth aspects of the present invention) and a structural gene positioned downstream from the promoter and operatively associated therewith. Also provided is the method for introducing such a construct into a cell, transforming the cell and expressing the structural gene in the transformed cell. Such a cell may be a plant cell which can be regenerated into a transformed plant which expresses the structural gene.

A sixth aspect of the present invention provides cultured cells and regenerated plants transformed by the constructs of the present invention. The transformed plant may be regenerated from the transformed plant cells.

A seventh aspect of the present invention provides for a method of selecting transformed plant cells which comprises the steps of: introducing into a plant cell an expression cassette comprising the ASA2 structural gene of the present invention which which encodes an AS which is substantially resistant to inhibition by free Trp or an amino acid analog of Trp to yield a transformed plant cell, and culturing the transformed plant cell in an amount of an amino acid analog of Trp, such as 5MT, that inhibits the growth of a corresponding plant cell which does not contain the ASA2 structural gene. This method can also be applied to cells of microorganisms, such as *Escherichia coli* (*E. coli*). In one embodiment of the invention, the expression cassette further contains a desirable gene. In another embodiment of the invention, the expression of the ASA2 structural gene is further inducible. In yet another embodiment of the invention, the desirable gene is under the control of a different promoter than that of the ASA2 structural gene; thus, the transformed cell or plant regenerated from the transformed cell can express the desirable gene independent of the expression of the ASA2 structural gene. The expression cassette, transformed cell and plant are also aspects of the invention.

An eighth aspect of the present invention provides for a method for imparting, to a plant cell, tolerance to an amino acid analog of Trp. The method comprises introducing an expression cassette containing the ASA2 structural gene of the present invention into cells of a wild-type plant to yield transformed plant cells, and expressing the ASA2 in an amount to render the transformed cells substantially tolerant to an amount of an amino acid analog of Trp that inhibits the growth of the untransformed cells of the wild-type plant. In one embodiment of the invention, the expression of the ASA2 structural gene is under the control of an inducible promoter. The transformed plant is also an aspect of the invention.

A ninth aspect of the present invention provides for altering the Trp content in a plant by transforming the plant cells with an expression cassette containing the ASA2 structural gene of the present invention, regenerating a differentiated plant from the transformed plant cells wherein the cells of the differentiated plant express ASA2 encoded by the expression cassette in an amount effective to increase the Trp content of the cells of the differentiated plant relative to the Trp content in the cells of the untransformed plant. In one embodiment of the invention, the expression of the ASA2 structural gene is controlled by an inducible promoter. The transformed plant is also an aspect of the invention.

A tenth aspect of the present invention provides for a method for producing AS which comprises the steps of: transforming a population of cells with expression cassettes comprising the ASA2 structural gene of the present invention, expressing the ASA2 in the cells, and recovering the expressed AS from the cells. The expressed AS may be further purified using methods known in the art with or without utilizing the antibodies of the present invention. The recombinant AS and substantially pure AS are also aspects of the present invention.

An eleventh aspect of the invention provides for the seeds ("transformed seeds") produced by any of the above transformed plants.

In the foregoing, ASA2 and its structural gene are merely used to illustrate the different aspects of the invention, one skilled in the art would realize that the foregoing is applicable to any AS and AS gene, and is preferably applicable to any AS and AS gene of the Nicotiana species (hereinafter referred to as "Nicotiana AS" and "Nicotiana AS gene", respectively).

The foregoing and other aspects of the present invention are explained in the discussion set forth-below.

BRIEF DESCRIPTION OF THE DRAWINGS

FIGS. 4A to 4C show an amino acid sequence alignment of AS genes that was performed by using the Pileup program (Genetics computer Group, Wisconsin Sequence Analysis Package). Dots within sequences indicate gaps. Asterisks represent a perfect match among these seven different AS sequences. Dots under the sequence indicate a perfect match among six plant AS sequences.

FIGS. 5A to 5C show photographs of complementation and inhibition tests.

FIG. 9 represents the DNA sequence of the ASA2 promoter fragment (SEQ ID NO: 13)

FIGS. 10A to 10B show GUS expression of tobacco transgenic plants.

FIGS. 15A and 15B show the nucleotide sequence comparison of the N. tabacum ASA2 and ASA3 genomic clones identified in Example 4.

FIGS. 22A and 22B presents quantitative data on the effect of 5MT on the growth of soybean hairy root lines and increased 5MT resistance of soybean hairy root lines by the introduced 35S-ASA2 gene construct. Hairy roots, initially about 200 mg, were grown for 8 weeks on MS medium containing serial concentrations of 5MT. At least 3 independent experiments were analyzed.

DETAILED DESCRIPTION OF THE INVENTION

Figure 1:
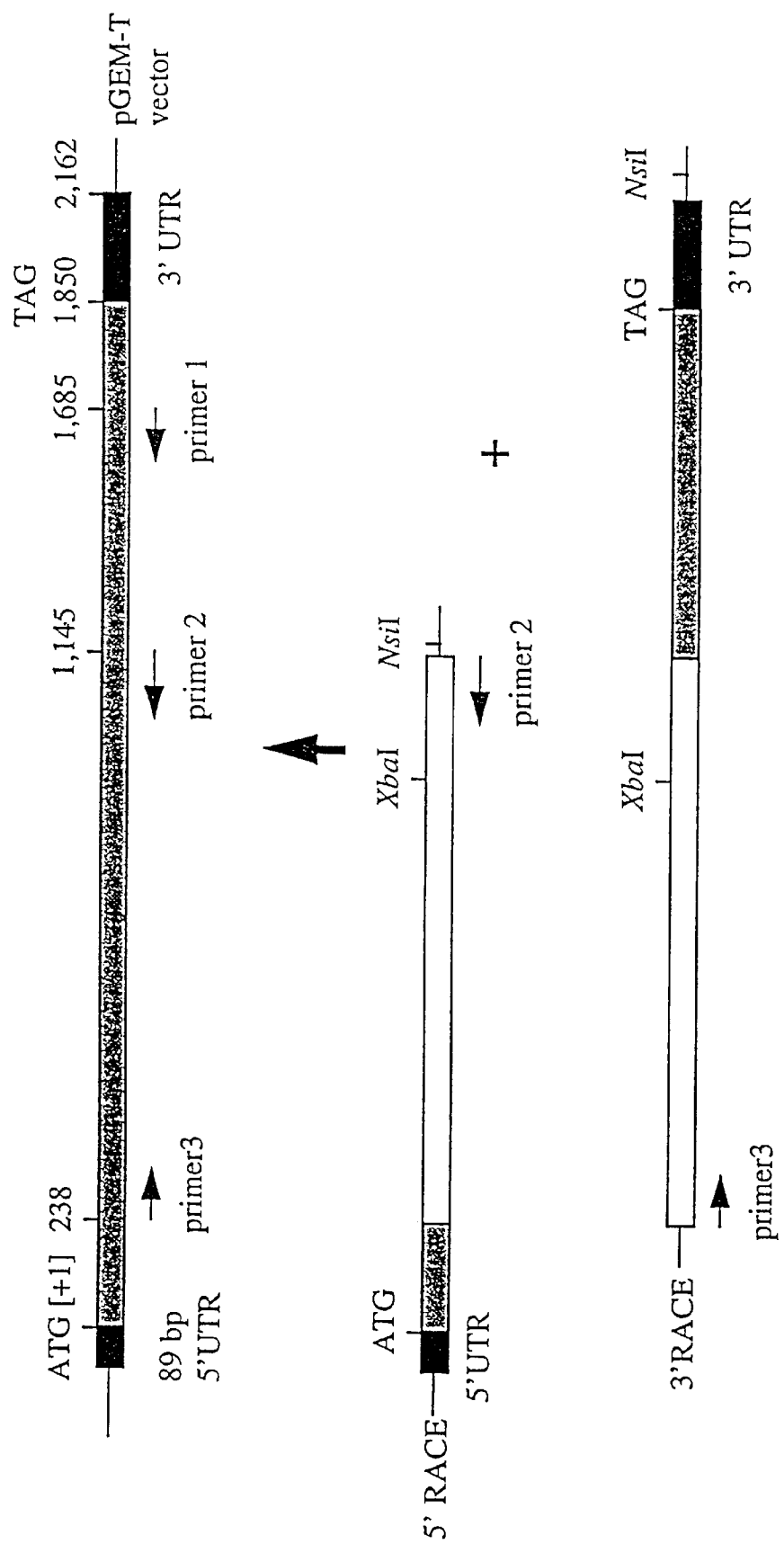
FIG. 1 shows a diagram of the tobacco ASA2 cDNA clone in the pGEM-T vector, the three primers used to isolate 5' and 3' ends of the ASA2 cDNA clones, and the unique restriction enzyme sites required to ligate these two cDNA clones to create the full-length, ASA2 cDNA clone. The arrows represent the orientation of each primer. The numbers on the bar represent the nucleotide sequence of the 5' end of each primer. The black bars represent either the 5' or 3' UTR (untranslated region). The white bars represent an overlapping region between the 5' and 3' clones. The region between 5' or 3' UTR and the overlapping region are denoted by gray bars in both fragments.

The chemical abbreviations used in this application are according to the Periodic Table. The amino acid and nucleotide abbreviations used in this application are according to the conventional scientific usage.

The present invention provides DNA sequences which encode the promoter, truncated promoters, and structural gene (ASA2) of the α-subunit of a feedback-insensitive form of the AS enzyme. Given the ASA2 nucleotide sequence disclosed herein, one skilled in the art may construct primers based on the sequence and employ the method disclosed herein, to obtain AS genes from other Nicotiana species which encode the feedback-insensitive form of the AS enzyme. For convenience, the following discussion uses ASA2 as an example of such a Nicotiana gene, however, one skilled in the art would realize that the invention is applicable to any gene encoding the feedback-insensitive form of the AS enzyme, and preferably a Nicotiana AS gene.

As used herein, a "feedback-insensitive form of the AS enzyme", or an AS which is "substantially resistant or tolerant to inhibition by free Trp or an amino acid analog of Trp" is an AS that is less inhibited by an amount of free Trp or an amino acid analog of Trp that normally inhibits the corresponding "wild-type" or native AS of the species.

According to one aspect of the present invention, the ASA2 structural gene could be contained on a DNA construct under the control of an upstream promoter and downstream terminator sequence, characterized in that the upstream promoter sequence is a DNA sequence that is homologous to the DNA control sequence found upstream of ASA2. The DNA construct may also contain another gene (i.e., a desirable gene) that is not operatively associated with the ASA2 promoter but would provide a desired trait when expressed in the plant. The DNA construct could then be used to select for plant cells in transformation experiments that are 5MT resistant and also contain a desirable gene that would improve on or in some way be desirable in a plant. Other structural genes as described below could be used instead of the ASA2 structural gene.

Another aspect of the present invention relates to promoters of AS genes which are able to drive the transcription of associated DNA sequences preferentially in tissue culture, and not in the tissues of regenerated plants and progeny.

Thus, a protein product of the DNA sequences operatively associated with the ASA2 promoter would be produced in greater amounts in tissue culture, with little or no expression in the tissues of a plant. The truncated forms of the ASA2 promoter (such as 370, 606, and 1356) can also be used to drive high levels of constitutive expression of useful genes in plant tissues. That is, the truncated ASA2 promoters provide constitutive promoters to drive high level transcription of downstream genes in plant tissues. Further, if the tissue culture specific transcriptional sequences are removed, these truncated promoters provide constitutive promoters to drive high level transcription of downstream genes in many plant species.

A selectable marker gene is usually driven by a promoter like the Cauliflower Mosaic virus (CaMV) 35S promoter. Therefore, the gene is expressed in all cells (tissue culture and regenerated plant). This is defined as constitutive expression. There has been considerable environmental concern because most selectable markers are constitutively expressed in all tissues of the plant and are not of plant origin. Because the promoter of the present invention would provide for transcription of associated DNA sequences preferentially in tissue culture, and not in the tissues of the plant, this problem would be removed.

Typically, the selectable marker and the desirable gene that expresses the trait of interest are put on the same plasmid, and in close proximity, so that they are both integrated together into the plant DNA. In addition, the selectable marker and the gene expressing the trait of interest may have their own promoters. If these genes are placed on a plasmid, the order and orientation of these genes is not expected to be important or relevant since plasmids are circular, and each gene is controlled by its own promoter and terminator.

It will be apparent from the discussion in this application and the examples that are described in greater detail below, that other fragments of the ASA2 promoter, longer or shorter than the 2.3 kb fragment originally isolated, or with minor additions, deletions, or substitutions made thereto, can be prepared which will also carry the tobacco ASA2 promoter, all of which are included within the present. invention. A further aspect of the present invention includes promoters isolated from other tobacco genes, or from plants other than tobacco as set forth below, which are homologous to the tobacco ASA2 promoter and are capable of directing tissue culture specific transcription of a downstream structural gene in a plant cell.

The ASA2 promoter sequences or the ASA2 structural genes may be obtained from other plant species by using ASA2 structural gene segments as probes to screen for homologous structural genes in other plants by DNA hybridization under low stringency conditions. Alternatively, the sequence of the regions of the ASA2 structural gene which are conserved among species could be used to design PCR primers to amplify a longer segment from a species other than tobacco, and that longer segment used as a hybridization probe (the latter approach permitting higher stringency screening). An example of high stringency screening is shown in Example 2, below, i.e., the screening involves washing the membranes twice at room temperature with 2×SSC and 0.5% SDS for 20 min. and at 65° C. with 0.1×SSC and 0.1% SDS until background signal disappeared. An example of low stringency screening involves washing the membranes twice at room temperature and at 42° C. for 20 min., respectively, with 2×SSC and 0.5% SDS.

Examples of plant species which may be used in accordance with the foregoing procedures to generate additional ASA2 promoter and AS sequences include *D. innoxia* and potato, and other Nicotiana species.

The research which led to the isolation of DNA sequences which encode for tissue culture specific expression of a 5MT resistant form of the AS enzyme began with the generation of 5MT resistant cell lines and the observation that 5MT resistance was lost in regenerated plants. The generation of the initial 5MT resistant cell lines is described in more detail in Example 1.

As described in Example 1, the mechanism of 5MT resistance in *N. tabacum* was different from that observed in other species such as carrot where only one enzyme form was detected in wild-type and 5MT-selected cultured cells (Brotherton et al., *Planta*, 168: 214–221, 1986). Wild-type carrot cells contained a Trp feedback-sensitive AS and 5MT selected carrot cells contained a Trp feedback-insensitive AS, suggesting that a structural gene mutation was causing insensitivity in the only or principal AS form. Unlike *N. tabacum*, plants regenerated from 5MT-selected *D. innoxia* cultured cells contained Trp feedback-insensitive AS and elevated levels of Trp suggesting a mechanism of 5MT-resistance more like that seen in carrot than in *N. tabacum*.

The decreased feedback control by Trp caused a build up of Trp in cells and plants while the decreased inhibition by 5MT or other Trp analogs (Widholm, *Biochem. Biophys. Acta* 261: 52–58, 1972) led to resistance to these normally toxic compounds. Thus, expression of the ASA2 structural gene in plant cells led to resistance to these analogs (Widholm, *Biochem. Biophys. Acta*, 261: 52–58, 1972), where 5MT-selected cells expressing the ASA2 structural gene grew in media containing 1100 $\mu$M 5MT while unselected cells did not grow in media containing 20 $\mu$M 5MT. This level of resistance to a Trp analog is greater than that reported for other Trp analog-selected cells or plants of other species like carrot (Widholm, *Biochem. Biophys. Acta*, 279: 48–57, 1972), *D. innoxia* (Ranch et al., *Plant Physiol.*, 71: 136–140, 1983), rice (Wakasa & Widholm in *Biotechnology in Agriculture and Forestry*, 14 Rice, Y. P. S. Bajaj (ed.), Springer-Verlag, New York, 304–315, 1991), *Lemna gibba* (Tam et al., *Plant Physiol.* 107: 77085, 1995) and *A. thaliana* (Kreps et al., *Plant Physiol.* 110: 1159–1165, 1996). AS from 5MT-selected potato cultured cells may be as Trp feedback-insensitive as AS from 5MT-selected tobacco cells, but the gene for this enzyme has not been isolated (Carlson & Widholm, *Physiol. Plant.* 44: 251–255, 1978,).

Li and Last (Plant Physiol. 110: 51–59, 1996) characterized an *A. thaliana* mutant selected using 6-methylanthranilate that contained an altered AS 95% inhibited by 100 $\mu$M Trp. Tobacco cells selected using 5MT and overexpressing the ASA2 structural gene contained AS that is 20% active at 900 $\mu$M (Brotherton et al., *Planta*, 168: 214–221, 1986), as is the AS from the *N. tabacum* cell line of the present invention which is designated AB15-12-1. Because the ASA2 structural gene product, e.g., as produced by the cell line AB15-12-1, of the present invention is much more Trp feedback-insensitive than other identified plant AS, except for an AS found in Ruta graveolens (Bohlmann et al., *Plant Physiol*, 111: 507–514, 1996), higher concentrations of Trp analogs could be used for more effective selection. Therefore, the ASA2 structural gene from *N. tabacum* of the present invention which encodes for a feedback-insensitive form of the enzyme would be a much more effective selectable marker in tissue culture transformation experiments than the AS structural gene identified by Li and Last (*Plant Physiol.* 110: 51–59, 1996).

Li and Last (*Plant Physiol.* 110: 51–59, 1996) also identified a single amino acid change (aspartate at position 341 was changed to asparagine) that they suggest results in the Trp feedback insensitivity of the *A. thaliana* mutant AS. In contrast, the tobacco ASA2 structural gene of the present invention produces a protein containing the amino acid sequence phenylalanine$_{107}$-arginine$_{108}$ near a site on AS important to Trp feedback inhibition. The wild-type and mutant Arabidopsis AS proteins and the tobacco ASA1 gene product (FIGS. 4A to 4C) contain serine-glutamine at this point in the aligned sequences, and these amino acids may be the cause of the Trp feedback insensitivity in 5MT-selected tobacco. The changes in the two amino acids (Phe$_{107}$ and Arg$_{107}$) located near a conserved region affecting feedback inhibition are similar to a change found in the amino acid (Arg$_{140}$) in the AS$\alpha$1 of Ruta graveolens encoding a feedback-insensitive AS $\alpha$-subunit as described by Bohlmann et al. (*Plant Physiol.* 111: 507–514, 1996). However, the Phe$_{107}$ is missing from the Bohlmann et al.'s sequence.

WO 97/26366, international publication date Jul. 24, 1997, of DeKalb Genetics Corporation (herein referred to as "DeKalb patent application") discloses maize AS gene and its uses. The application claims that the amino acid sequence at 377, Lys instead of Met, is important for feedback inhibition to Trp.

In contrast, we found that in tobacco ASA2, the amino acids Phe and Arg at positions 107 and 108, respectively, are responsible for feedback insensitivity to Trp and resistance to 5MT. This was confirmed by site-directed mutagenesis of Example 7.

In summary, the main region of the amino acid sequence responsible for feedback insensitivity to Trp and analogs such as 5MT, and degree of feedback sensitivity of AS enzyme against exogenous Trp are different between the maize ASA2 of the DeKalb patent application and the tobacco ASA2 of the present application.

Further, the DeKalb patent application claims its maize ASA2 sequence is highly homologous to Arabidopsis ASA genes which will allow the maize ASA2 to be used as a probe to hybridize to other AS genes under high stringency conditions.

In contrast, we had failed, despite numerous tries, in using Arabidopsis ASA1 and ASA2 cDNA as probes to hybridize with tobacco genomic DNA. There was no clear hybridization even under low stringency conditions, despite sequence alignment which appeared to show 62% amino acid identity between Arabidopsis and tobacco AS genes. Only under very low stringency conditions, and using 200 bp of the 3' fragment of the Arabidopsis ASA1 cDNA as a probe, did we find very faint hybridization.

If the ASA2 gene (cDNA clone) were driven by the ASA2 promoter of the present invention, then it should only be expressed for selective purposes in cultured cells and not in regenerated plants as demonstrated using the selection and regeneration experimental protocols described in Brotherton et al. (Brotherton et al., *Planta* 168: 214–221, 1986 and Widholm, in *Plant Cell Cultures: Results and Perspectives*, F. Sala, B. Parisi, R. Cella, O. Ciferri (eds.), Elsevier/North Holland Biomedical; Press, Amsterdam, pp. 157–159, 1980).

The cloned ASA2 gene may also be overexpressed in *E. coli* to obtain large amounts of the enzyme for further study. The protein may be expressed with a 6 histidine ("6xHIS") tag that facilitates its purification from the *E. coli* cell extract. The 6xHIS attached to the overexpressed protein through a transcriptional fusion would allow one to purify the protein by binding to Ni-affinity resin since the His amino acids bind to this complex. There are many other similar strategies including fusing a protein of interest to glutathione-S-transferase and binding this to glutathione-affinity media. The ASA2 protein could then be used to study the Trp binding/inhibition and can be used as an antigen to produce antibodies, both monoclonal and polyclonal, for several uses. Purified antibody to the ASA2 encoded protein could be used in Western Blot analysis of various plant tissues. Somewhere in a normal plant under the appropriate conditions, the ASA2 gene may be expressed at low levels. Western blots and dot blots probed with antibody directed to ASA2 could be used to try to identify or confirm Northern blot results localizing ASA2 expression. Alternatively, antibody could also be used as an immunohistochemical probe to determine when in the plant's life cycle, under what environmental condition, or where in the cell or whole plant, the Trp feedback-insensitive AS is expressed.

Antibodies could also be used to study and purify the native protein from wild-type and 5MT-selected cells in order to understand the subunit composition of the enzyme from both types of cells. In addition, antibodies could also be used to study AS from cells and plants of other species including potato, where like in tobacco, 5MT-selection resulted in two separable AS forms.

If the *E. coli* expressed ASA2 encoded protein is enzymatically active, its feedback characteristics could be studied in several ways. Site-directed mutagenesis would be a direct method to confirm the relationship between a particular amino acid(s) in the protein sequence and Trp feedback insensitivity. Other methods would include mutagenesis followed by selection for Trp analog resistance that should produce random changes in the AS sequence.

The ASA2 cDNA indeed produces a protein when expressed in *E. coli* that is appreciably more feedback-insensitive to Trp than is Arabidopsis ASA1. enzyme (FIG. 6) indicating that indeed this is a gene for a feedback-insensitive AS and that the amino acid alterations mentioned above are responsible for this.

We have also tested and confirmed that the tobacco ASA2 produces free Trp by using the *E. coli* system (see Example 7). In Example 7, to study overproduction of free Trp by ASA2, we plated the ASA2 complemented *E. coli* in the center of 300 $\mu$M 5MT-containing minimal medium without Trp and the *E. coli* cells transformed with site-directed mutagenized ASA2 which was feedback-sensitive, were plated adjacent to the ASA2 complemented *E. coli* strain. It was found that the *E. coli* cells transformed with the site-directed mutagenized ASA2 could only grow where they were located close to the *E. coli* cells transformed: with the ASA2 on the 300 $\mu$M 5MT-containing minimal medium but without Trp, while the *E. coli* cells transformed with the site-directed mutagenized ASA2 alone could not grow even on 10 $\mu$M 5MT-containing minimal medium without Trp.

The original 5MT-resistant cell lines used as a source to clone the ASA2 gene exhibits 50% enzyme activity of the feedback-insensitive ASA2 at 100 $\mu$M Trp. This value is at least six times higher than those found for maize ASA2 (described in the DeKalb patent application, above) and mutant Arabidopsis ASA1 enzyme activities. This enzyme activity of tobacco ASA2 was also shown in partially purified tobacco ASA2 using the *E. coli* system.

To achieve the different aspects of the present invention, methods known in the art may be modified by using the ASA2 gene, ASA2 promoter, and ASA3 gene sequences disclosed in the present application. Such methods are found, e.g., in the DeKalb patent application, which is herein incorporated by reference in its entirety. Examples of how such methods may be applied to the present invention are: methods for transforming cells with the genes of the present invention, strategy for selecting the resulting Trp overproducer cell lines, selection and characterization of the resistant cell lines, plant regeneration and production of seeds, and development of Trp overproducer commercial hybrid seeds; formation of an expression cassette containing the sequences disclosed herein, optional and additional DNA sequences to be added into the expression cassette, methods for screening for expression of the AS gene or expression cassette of the present invention; methods of imparting tolerance to an amino acid analog of Trp and/or altering Trp content in the cell or tissue of a plant or microorganism by introducing the genes of the present invention, methods for introducing the genes of the present invention and producing AS; and commercial approaches to Trp extraction from the resulting high Trp seeds, such as maize and soybean seeds. Non-limiting examples of these methods are further described below.

Definitions

As used in the present application, the term "substantial sequence homology" or "homologous" is used to indicate that a nucleotide sequence [in the case of DNA or ribonucleic acid (RNA)] or an amino acid sequence (in the case of a peptide, protein or polypeptide) exhibits substantial functional or structural equivalence with another nucleotide or amino acid sequence. Any functional or structural differences between sequences having substantial sequence homology will not affect the ability of the sequence to function as indicated in the present application. For example, a sequence which has substantial sequence homology with a DNA sequence disclosed to be a plant cell tissue culture specific promoter will be able to direct the plant cell tissue culture specific expression of an associated DNA sequence. Sequences that have substantial sequence homology with the sequences disclosed herein are usually variants of the disclosed sequence, such as mutations, conservative amino acid changes, but may also be synthetic sequences. Structural differences are considered to be negligible if there is a significant sequence overlap or similarity between two or more different sequences or if the different sequences exhibit similar physical characteristics. Such characteristics can include, for example, immunological reactivity, enzyme activity, structural protein integrity, etc.

Two nucleotide sequences may have substantial sequence homology if the sequences have at least 70 percent, more preferably 80 percent and most preferably 90 percent sequence similarity between them. Two amino acid sequences have substantial sequence homology if they have at least 50 percent, preferably 70 percent, and most preferably 90 percent similarity between the active portion of the polypeptides.

In the case of promoter DNA sequences, "substantial sequence homology" also refers to those portions of a promoter DNA sequence that are able to operate to promote the expression of associated DNA sequences. Such operable fragments of a promoter DNA sequence may be derived from the promoter DNA sequence, for example, by cleaving the promoter DNA sequence using restriction enzymes, synthesizing in accordance with the sequence of the promoter DNA sequence, or may be obtained through the use of PCR technology (Nisson et al., *PCR Methods and Applications*, 1: 120, 1991).

Further, as used in this application and claims, the SEQ ID Nos. and disclosed nucleotide sequences include: (1) the DNA sequences as disclosed, (2) the complementary nucleotide sequences (which may be RNA or DNA) to the disclosed sequences or their coding sequences, (3) the corresponding RNA sequences to the listed DNA sequences wherein the thymidine ("T") in the disclosed DNA sequences is replaced with uracil ("U"), (4) nucleotide sequences wherein other nucleotides known in the art such as nucleotide analogs, replace those in the foregoing sequences, for example, 5-methyl-cytosine replacing cytosine, (6) nucleotide sequences that are homologous to the disclosed sequences, and (7) nucleotide sequences coding for the homologous peptides, polypeptides, or proteins. These sequences may be naturally occurring or synthetic. Since nucleotide codons are redundant, also within the scope of this invention are nucleotide sequences which code for the same proteins or homologous proteins. These latter nucleotide sequences may also be used in the practice of the invention.

Similarly, as used in this application and claims, the SEQ ID Nos. and disclosed amino acid sequences include sequences that are homologous to or have substantial sequence homology to these SEQ ID Nos. and disclosed amino acid sequences. Also within the scope of the present invention are peptides, polypeptides, and proteins which are homologous to those disclosed herein, such as ASA1 and ASA2.

The term "operatively associated" as used herein, refers to DNA sequences on a single DNA molecule which are associated so that the function of one is affected by the other. Thus, a promoter is operatively associated with a structural gene when it is capable of affecting the expression of that structural gene (i.e., the structural gene is under the transcriptional control of the promoter). The promoter is said to be "upstream" from the structural gene, which is in turn said to be "downstream" from the promoter.

Conversely, "not operatively associated" as used herein, refers to DNA sequences on a single DNA molecule which are not associated so that the function of one is not affected by the other. Thus, the ASA2 promoters of the present invention can be used with or without being operatively associated with the desirable gene on the DNA construct described below.

DNA constructs of the present invention may include 5' to 3' in the direction of transcription, a promoter of the present invention and a structural gene operatively associated with the promoter. The structural gene may encode a tobacco AS which is resistant to free Trp or an amino acid analog of Trp, such as 5MT. The preferred tobacco AS is the 5MT resistant form of the AS from *N. tabacum* of the present invention or any of the other selectable markers described below.

In another aspect of the invention, the structural gene of tobacco AS which is resistant to free Trp or an amino acid analog of Trp may be operatively associated with promoters of the present invention or a promoter known in the art. Non-limiting examples of promoters known in the art are: CaMV 35S, cassava vein mosaic virus, potato ubiquitin, *A. thaliana* actin, *Pea mays* ubiquitin and soybean seed lectin promoters. The promoter is preferably inducible. The inducible promoter may preferentially promote the expression the ASA2 gene in cultured cells or tissue but not in plant, or vice versa. Such a promoter includes those disclosed in the present invention. Alternatively, the inducible promoter may be induced to promote the expression of the ASA2 gene based on other external factors such as temperature, chemicals and metals to which the transformed cells are exposed. Inducible promoters known in the art may be used, non-limiting examples of which are: auxin, tetracycline, copper and ethanol.

Another DNA construct that may be constructed would also include a desirable gene that when expressed affects the plant in a desired way. As described below, this gene may or may not be operatively associated with the promoter of the present invention. For example, the DNA construct may have ASA2 gene operatively associated with an inducible promoter, and the desirable gene operatively associated with another independent promoter. The independent promoter may be inducible. The inducible promoters and promoters known in the art described above, may be used. Thus, one skilled in the art may selectively induce expression, in the transformed cells or plant, of the ASA2 gene but not the desirable gene. For example, if the ASA2 promoter of the present invention or another inducible promoter is operatively associated with the ASA2 gene, it would be useful for controlling the ASA2 gene (the latter serving as a selectable marker) which would be expressed in and be used to select for the transformed cultured cells but not expressed in plants regenerated from these transformed cells; meanwhile, the desirable gene is operatively associated with yet another promoter which allows the expression of the desirable gene in the transformed cultured cells and/or transformed plants. Alternatively, the ASA2 gene may be constitutively expressed, by being operatively associated with a constitutive promoter, such as the constitutive truncated ASA2 promoters of the present invention. Yet another embodiment of the invention presents the ASA2 gene and the desirable gene being operatively associated with the same promoter. One skilled in the art would realize that in the above embodiment, one or more desirable gene(s) and promoter(s) may be used in the construct.

Thus, for example, in the present invention, the ASA2 sequence and/or the desirable gene may be inserted into a DNA construct such as a recombinant expression vector. The term "recombinant expression vector" refers to a plasmid, virus or other vehicle known in the art that has been manipulated by insertion or incorporation of ASA2 genetic sequence. Such expression vectors contain a promoter sequence which facilitates the efficient transcription of the inserted genetic sequence in the host. The expression vector typically contains an origin of replication, a promoter, as well as selectable marker genes (described further below) which allow phenotypic selection of the transformed cells. The latter genes are unnecessary, if ASA2 gene is used as the selectable marker. The transformed host cells can be cultured according to means known in the art to achieve optimal cell growth. Known biologically functional DNA vectors capable of expression and replication in a host and methods for preparing fused, operably linked genes and expressing them in prokaryotes and eukaryotes may be used. Examples of plasmids which can be used in the invention are listed in Sambrook et al. (*Molecular Cloning: A Laboratory Manual*, 2nd ed., Cold Spring Harbor Laboratory Press, 1989) which also discloses the general methods for making DNA constructs, expressing them in transformed cells, selecting for and growing the transformed cells.

Structural genes are those portions of genes which comprise a DNA segment coding for a peptide, protein, polypeptide, or portion thereof, possibly including a ribosome binding site and/or a translational start codon, but lacking a promoter. The term can also refer to copies of a structural gene naturally found within a cell but artificially introduced. The structural gene may encode a protein not normally found in the plant cell in which the gene is introduced or in combination with the promoter to which it is operatively associated, in which case it is termed a heterologous structural gene.

In one embodiment of the invention, the structural gene that would be operatively associated with the promoter of the present invention is tobacco AS which is resistant to free Trp or an amino acid analog of Trp, and is most preferably the ASA2 gene encoding the α-subunit of the 5MT resistant form of AS from *N. tabacum*. The structural gene could function as a selectable marker in plant cell tissue culture transformation, allowing one to identify plant cells harboring the DNA construct containing the selectable marker and the gene that affects the plant in some desired way. Unlike other selectable markers described below, this selectable marker of the present invention is of plant origin. Commonly used selectable markers provide protection against antibiotics, toxins, heavy metals, and the like. Genes which may be employed as selectable markers include neomycin phosphotransferase (nptII) which provides kanamycin resistance; hygromycin phosphotransferase (hpt) which provides hygromycin resistance; and phosphinothricin-acetyl transferase which provides phosphinothricin resistance. Expression of antibiotic detoxifying genes in plants is a concern since it could lead to antibiotic resistant forms of plants and this antibiotic resistance could be spread to microorganisms. Likewise, herbicide resistance could be spread to weeds. In addition, possible allergic reactions to foreign proteins expressed in plants could be alleviated if the selectable marker were of plant origin or not expressed in the plant as would be the case if the selectable marker were under the control of the promoters of the present invention.

The structural gene of the present invention that may or may not be operatively associated with the promoter of the present invention on a DNA construct is described next. Desirable genes of interest for use in plants include those affecting a wide variety of phenotypic and non-phenotypic properties. Some phenotypic properties commonly selected for include resistance to herbicides, disease, salt, metals, high or low pH, flooding, heat, cold, drought, insects and low nutrients. These genes may be obtained from prokaryotes, eukaryotes or archaebacteria and may be synthesized in whole or in part. Other structural genes are further described below, using the truncated ASA2 promoters as examples, though these structural genes could also be used with the full promoter.

The recombinant DNA vectors of the present invention are those vectors that contain sequences of DNA that are required for the transcription of cloned copies, of genes and for the translation of their mRNAs in a host. The recombinant DNA vectors typically have at least one origin of replication. For convenience, it is common to have a replication system functional in *E. coli* such as ColE1, pSC101, pACY184, or the like. In the present invention, such vectors as pGEM5, pBluescript SK– and pUC19 were used.

Plant cells, cells of other organisms (including both prokaryotes and eukaryotes, such as *E. coli*, bacterial, insect, yeast, and mammalian cells), and viruses may be transformed with the DNA constructs of the present invention according to a variety of known methods including particle bombardment of cells or tissues with a device such as the particle inflow gun (Vain et al., *Plant Cell Tissue Organ Culture*, 33: 237–246, 1993), electroporation of protoplasts (Shillito et al., *Bio/Tech* 3: 1099–1103, 1985)., and Agrobacterium mediated transformation (Vermeulen et al., *Plant Cell Reports*, 11: 243–247, 1992) if the promoter and selectable marker and/or desirable gene are placed into the correct plasmid in the bacterium. The cells can be cultured cells or cell lines. In the case of transformed plant cells, they may then in suitable cases be regenerated into whole plants in which the new nuclear material is stably incorporated into the genome. Both transformed monocot and dicot plants may be obtained in this way, although the latter are usually more easy to regenerate.

Any plant tissue capable of subsequent clonal propagation, whether by organogenesis or embryogenesis, may be transformed with a vector of the present invention. The term "organogenesis" as used herein, means a process by which shoots and roots (organs) are developed sequentially from meristematic centers; the term "embryogenesis", as used herein, means a process by which shoots and roots develop together in a structure similar to an embryo in a concerted fashion (not sequentially), whether from zygotic or somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

The ASA2 structural gene of the present invention could be used to transform cells, tissues, and plants such as either monocot or dicot plant species, plant tissues, or plant cells, in order to increase intracellular free Trp, which is of nutritional value. In addition, these transformed plants and cells would be candidates for investigating the effect of the ASA2 gene product on AS characteristics and metabolism. The AS may be harvested or recovered from such transformed cells, tissues, or plant species and preferably further purified using methods known in the art, with or without using the antibodies of the present invention.

Alternatively or additionally, the ASA2 structural gene of the present invention could be used to transform a cell, tissue, or plant to make it more resistant to Trp analogs as compared to its untransformed counterpart.

The ASA1 cDNA clone also disclosed herein can be used for comparison with the ASA2 cDNA clone since ASA1 encodes a feedback-sensitive AS. This is shown by the nucleotide sequence that reveals ASA1 to be similar to *A. thaliana* ASA1 and different from the tobacco ASA2.

The promoter sequences disclosed herein may be used to express a structural gene, such as the ASA2 gene encoding the α-subunit of the feedback-insensitive form of AS, in any plant species capable of utilizing the promoter. Other structural genes are described above. Additional structural genes are further described below, using the truncated ASA2 promoters as examples, though these structural genes could also be used with the full promoter. These would include both monocot and dicot plant species. The ASA2 promoter of the present invention should be capable of functioning in any system where relatively undifferentiated. cells in culture are used for the selection.

The ASA2 promoter and its truncated versions can be used in place of CaMV 35S for driving the genes generally driven by CaMV 35S. The constructs containing the promoters of the present invention and any downstream genes may be constructed using techniques described herein or modifications thereof which will be obvious to one skilled in the art based on the teaching of this application.

In addition, the truncated versions of the tobacco ASA2 promoter and promoter homologous to it which can drive high level transcription in many tissues of plants of some species (constitutive expression) are useful as promoters for many downstream structural genes. Examples of such truncated versions of the tobacco ASA2 promoter are the 606 fragment and promoters homologous to it. In the transient expression assays of FIG. 8 (and Example 3, below), the 606 fragment showed the highest expression in leaves while reducing the ASA2 promoter to 370 bp gave the resulting fragment a somewhat lower level of expression. In experiments using the protocols of Example 3, it was found that smaller fragments of the tobacco ASA2 promoter, i.e., a 151 fragment (from position −1 to −1,51) and a 214 fragment (from position −1 to −214) also provide constitutive expression (data not shown). The 214 fragment has double the expression level of the 151 fragment. Thus, using the teaching in this application, one skilled in the art can determine, without undue experimentation, a fragment of the promoter that will produce a desired constitutive expression. At the very least, a fragment from about −151 to about −606 of the ASA2 promoter, and fragments homologous to it are expected to control constitutive expression. These fragments, in addition to the full ASA2 promoter, may be used in a construct to transform and produce cultured cells and regenerated plants using methods known in the art. For example, these fragments may be used, in place of the full ASA2. promoter, in the construct in Example 6 to produce cultured cells and regenerated plants which express a downstream structural gene with desired characteristic(s) (desirable gene).

Non-limiting examples of the downstream structural genes are genes of various kinds which could be used for plant improvement or modification, some of these are structural genes described above. Other non-limiting examples of the downstream structural genes include: genes that might make plants resistant to diseases [e.g., the *Phaseolus vulgaris* Ch 18 (chitinase): gene (Broglie et al., Sci. 254: 1194–1197, 1991)]; resistant to insects [e.g., the *Bacillus thuringiensis* (hereinafter referred to as *B. thuringiensis*) cry1AC gene (Stewart et al., *Plant Physiol.* 112: 121–129, 1996)]; resistant to drought [e.g., the *Vigna aconitifolia* P5CS (Pyrroline-5-carboxylate synthetase) gene (Kishor et al., *Plant Physiol.* 108: 1387–1394 (1995)]; or resistant to herbicide [e.g., the csr1-1 gene from *A. thaliana* (acetolactate synthase) (Vermeulen et al., *Plant Cell Reports* 11: 243–247, 1992)] among many other possibilities. For example, the expression noted for 606 in Example 3, below, was as good as or better than the CaMV 35S promoter that has been used to drive high level transcription of many genes, for example an insect resistance gene, cry1Ac from *B. thuringiensis*, in soybean and cause the soybean plants to be resistant to four different insects (Stewart et al., *Plant Physiol.* 112: 121–129, 1996). As a non-limiting example of an expression construct, the truncated 0.6 kb ASA2 promoter fragments (SEQ ID NO: 14) can be attached to many possible desirable genes to be expressed in plants since this portion of the ASA2 promoter drives constitutive expression of genes in many species (Table 2, FIG. 8). The transformation would be accomplished as explained in Example 5, below. The 606 promoter drives high levels of constitutive expression of structural genes placed downstream in plant tissues so various genes can be then expressed to impart many useful traits such as insect resistance if a gene such as the *B. thuringiensis* cry1AC is expressed (Stewart et al., 1996) and other traits as described above.

The 606 promoter and promoters homologous to it will drive expression in cultured cells so they can also be used to drive selectable marker genes. The expression in tissue cultures would also allow one to express genes in cultured cells to show that these genes can be expressed and to determine the effect on the cells. The gene product could also be isolated for other studies. Since these promoters are of plant origin, there should not be a real or perceived environmental problem if the promoters are present in plants.

The invention may be better understood with reference to the accompanying examples, which are intended for purposes of illustration only and should not be construed as in any sense limiting the scope of the invention as defined in the claims appended hereto.

EXAMPLE 1

Plant Regeneration from 5MT Resistant Cell Lines

A. Selection and Plant Regeneration

As described in further detail in Widholm (in *Plant Cell Cultures: Results and Perspectives*, F. Sala, B. Parisi, R. Cella, O. Ciferri (eds.), Elsevier/North Holland Biomedical Press, Amsterdam, pp. 157–159, 1980) and Brotherton et al. *(Planta* 168: 214–221, 1986), suspension cultured *N. tabacum* cells were selected for 5MT resistance by growing about 3 ×10$^6$ cells (one gram fresh weight) in each flask in the presence of a completely inhibitory concentration of the Trp analog (46 μM). Some cells grew in some flasks in 60 days and these continued to grow if placed in 229 μM 5MT. Plants were regenerated by placing some cells onto an agar-solidified medium containing the plant growth regulators, 1.0 mg/l indole-3-acetic acid (Sigma Chemical Company, St. Louis, Mo.) and 0.64 mg/l kinetin (Sigma Chemical Company), instead of 0.4 mg/l 2, 4-dichlorophenoxyacetic acid (Sigma Chemical Company) that was in the suspension culture medium. Shoots that formed in about a month were rooted in solid medium with no growth regulators.

B. Demonstration that 5MT Resistance is Lost in Regenerated Plants

As further described in Widholm (in *Plant Cell Cultures: Results and Perspectives*, F. Sala, B. Parisi, R. Cella, O. Ciferri (eds.), Elsevier/North Holland Biomedical Press, Amsterdam, pp. 157–159, 1980), *N. tabacum* L. cv. Xanthi suspension cultures were selected for 5MT resistance. The selected cells grew in the presence of 229 μM 5MT, contained a Trp feedback-insensitive AS and elevated levels of intracellular free Trp. Leaves of six plants regenerated from this 5MT-selected cell line did not contain a detectable level of the Trp feedback-insensitive AS, but cultures reinitiated from leaf pieces from these plants were again 5MT-resistant, contained the Trp feedback-insensitive AS and had elevated levels of Trp. Brotherton et al. *(Planta* 168: 214–221, 1986) reported that extracts of shoot tips, stems and roots of another set of plants regenerated from 5MT resistant tobacco cultures did not contain kinetically detectable levels of Trp feedback-insensitive AS. Using Sephacryl S-200 chromatography or steric exclusion high performance liquid chromatography, two forms of AS were separated from extracts of 5MT-selected and wild-type cultured cells. The 5MT-selected cultured cells contained more of the Trp feedback-insensitive As than did the wild-type cells. No Trp feedback-insensitive AS could be detected in extracts of plants regenerated from either 5MT-selected or wild-type cell lines using,Sephacryl S-200 chromatography. These results were interpreted to support the hypothesis that the two forms of AS present in wild-type and 5MT-selected cultured cells were two unique enzymes whose expression was independently regulated. This mechanism of 5MT resistance was different from that observed in other species such as carrot where only one enzyme form was detected in wild-type and 5MT-selected cultured cells (Brotherton et al., *Planta* 168: 214–221, 1986). Wild-type carrot cells contained a Trp feedback-sensitive AS and 5MT-selected cells contained a Trp feedback-insensitive AS suggesting a structural mutation causing insensitivity in the only or principal AS form. Unlike *N. tabacum*, plants regenerated from 5MT-selected *D. innoxia* cultured cells contained Trp feedback-insensitive AS and elevated levels of Trp suggesting a mechanism of 5MT-resistance more like that seen in carrot than in *N. tabacum* (Ranch et al., *Plant Physiol.*, 71: 136–140, 1983).

EXAMPLE 2

Cloning and Characterization of the ASA2 Gene

A. Preparation of Plant Total RNA for Cloning

The 5MT-resistant tobacco (*N. tabacum*) suspension cell line, AB15-12-1 was used as the source of plant material. The AB lines originated from progeny of one plant regenerated from unselected *N. tabacum* cv. Xanthi tissue cultures. Callus induced from the leaf of the AB-15-12-1 plant, tested resistant to 5MT, and has been maintained until now with both MX medium (Murashige & Skoog, *Physiol. Plant.* 15: 431, 1962, containing 0.4 mg/l 2,4-dichlorophenoxyacetic acid) containing 300 $\mu$M 5MT and 5MT-free MX medium. The AB-15-12-1 cell line maintained in MX medium containing 300 $\mu$M 5MT (A.T.C.C. Accession Number 209176) was used for the preparation of plant total RNA for cloning below.

Plant total RNA was prepared from one-week-old AB15-12-1 suspension cultured cells by using a combination of a phenol extraction method (McCarty, D. R., et al., *Maize Genetics Coop, Newslett*. 60, 61, 1986 and Ausubel et al., *Current Protocol in Molecular Biology*, New York: Greene Publishing Associates and Wiley-Interscience, 1989) and CsCl-gradient purification (Sambrook et al., *Molecular Cloning: A Laboratory Manual*, 2nd ed., Cold Spring Harbor Laboratory Press, 1989).

Tobacco AS cDNAs were isolated by using 5' and 3' RACE (Rapid Amplification of cDNA End System, Gibco BRL, Grand Island, N.Y.) and cloned into the pGEM-T vector (Promega, catalog #A360, Madison, Wis.).

B. Cloning the ASA2 Gene (SEQ ID NO: 4)

FIG. 1 shows a diagram of the tobacco ASA2 cDNA clone in the pGEM-T vector, the three primers used to isolate 5' and 3' ends of the ASA2 cDNA clones, and the unique restriction enzyme sites required to ligate these two cDNA clones to create the full-length ASA2 cDNA clone. Because we isolated a 5' end truncated tobacco ASA1 cDNA before isolating the ASA2 cDNA, primers for cloning the 5' end of the ASA2 cDNA were designed based on the sequence of the tobacco ASA1 cDNA clone (SEQ ID NO: 24).

For 5' RACE, first stranded cDNA was synthesized with primer I (SEQ ID NO: 1). A nested PCR was performed with primer 2 (SEQ ID NO: 2,). The first stranded cDNA was used as a template for the nested PCR. The PCR reaction was prepared with a final concentration of 0.2 mM of primer (primers 1 and 2 as explained above), 2.5 mM MgCl$_2$, 0.2 mM dNTP mixture and 2.5 units of Taq DNA polymerase. Two sets of thermocycling conditions were programmed by using a PTC-100 (Programmable Thermal Controller, MJ Research, Inc, Watertown, Mass.). Additional denaturation at 94° C. for 5 min and at 80° C. for 3 min. was performed before starting the thermocycling. Taq DNA polymerase was added at 80° C. The first 10 cycles were programmed for denaturation at 94° C. for 1 min., annealing at 50° C. for 2 min., and extension at 72° C. for 2 min. The second 20 cycles were programmed for denaturation at 94° C. for 1 min., annealing at 45° C.+0.4° C. (0.4° C. increasing at each cycle) for 2 min., and extension at 720° C. for 2 min. Additional extension at 72° C. for 10 min. was performed after 30 cycles.

An approximately 1.1 kb fragment was detected by Southern hybridization with tobacco ASA1 and Arabidopsis ASA1 (pKN41/XhoI, 1.8 kb) and ASA2 cDNA clones (pKN108A/BamHI, 2.0 kb) (Niyogi & Fink, *The Plant Cell*, 4: 721–733, 1992) as probes by using a Megaprime DNA labelling system (Amersham) with [$\alpha$-$^{32}$P]dCTP (3000 Ci/nmol). Southern hybridization was done at 42° C. with a hybridization solution (50% formamide, 5×SSPE, 5× Denhardt's solution, 0.1% SDS, and 100 $\mu$g/ml salmon sperm DNA). The membranes were washed at high stringency. This involved washing the membranes twice at room temperature with 2×SSC and 0.5% SDS for 20 min. and at 65° C. with 0.1×SSC and 0.1% SDS until background signal disappeared. This tobacco ASA2 5' end cDNA fragment was cloned into commercially available pGEM-T vector (Promega) and sequenced by the Genetic Engineering Lab, University of Illinois at Urbana-Champaign.

Most of the procedures to isolate the 3' end of the tobacco ASA2 cDNA were the same as for 5' RACE except for primers and dATP tailing at the 5' end of the cDNA. Primer 3 (SEQ ID NO: 3) was designed based on the sequence of the 5' ASA2 cDNA clone. An approximately 1.9 kb fragment was detected by Southern hybridization with the 5' ASA2 cDNA clone as a probe, cloned into the pGEM-T vector, and sequenced (FIGS. 4A to 4C.).

The sequencing results analyzed by the BLAST program showed that these two clones are the same AS gene, since the nucleotide sequences of an 828 bp overlapping region (indicated as a white bar in FIG. 1) perfectly matched. There is only one XbaI site in the 828 bp overlapping region, only one NsiI site in pGEM-T vector, and no NsiI site in both 5' and 3' fragments. The 5' cDNA clone in pGEM-T vector was digested with XbaI and NsiI to remove the 3' end of the sequence downstream of the XbaI site, which is approximately 318 bp including 57 bp of multiple cloning site. The 3' cDNA clone was digested with XbaI and NsiI to isolate the 3' end fragment of the ASA2 gene (approximately 1.4 kb including 16 bp poly(A) and 57 bp of the multiple cloning site), which was cloned into the 5' end of the ASA2 gene in pGEM-T vector. These two fragments were ligated to create the full-length tobacco ASA2 cDNA (A.T.C.C. Accession Number 209152).

Figure 2:
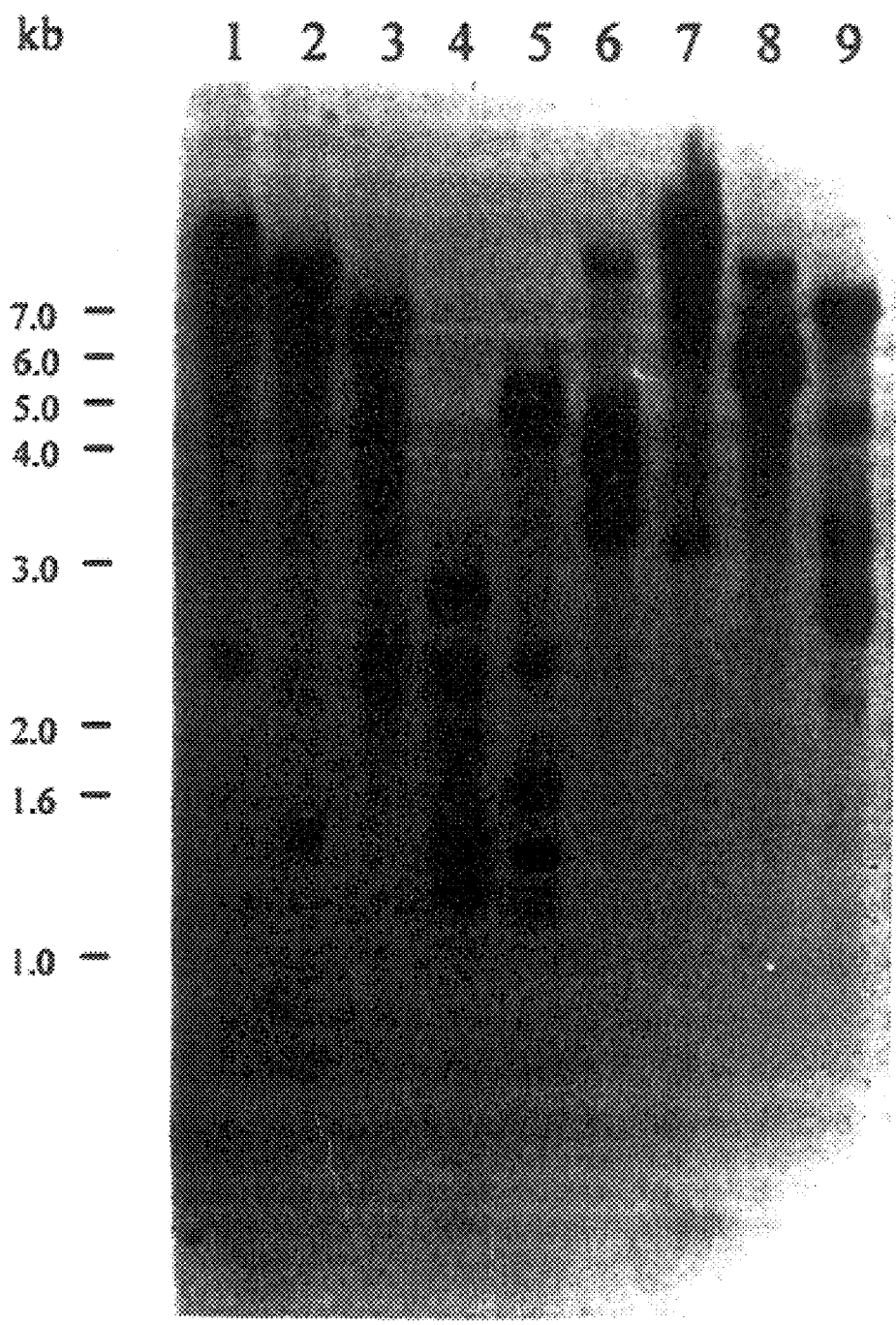
FIG. 2 shows a Southern hybridization of AB15-12-1 genomic DNA. The DNA was digested with nine different restriction enzymes (lane 1 to 9: BamHI, EcoRI, EcoRV, HincII, HindIII, KpnI, PstI, ScaI, and XbaI in order) and probed with the full-length (2.16 kb) ASA2 cDNA fragment.

The full-length (2.16 kb) ASA2 cDNA fragment including 5' and 3' UTR was used as a probe to determine how many ASA2 genes exist in the tobacco genome by using Southern hybridization (FIG. 2). Twenty $\mu$g of AB15-12-1 genomic DNA isolated by using CsCl-gradient purification (Ausubel et al., *Current Protocol in Molecular Biology*, New York: Greene Publishing Associates and Wiley-Interscience, 1989 and Sambrook et al., *Molecular Cloning*, 2nd ed., Cold Spring Harbor Laboratory Press, 1989) were digested with nine different restriction enzymes (lane 1 to 9: BamHI, ECoRI, EcoRV, HincII, HindIII, KpnI, PstI, ScaI, and XbaI in order), followed by electrophoresis in a 0.8% agarose gel at 30 volts overnight. Southern hybridization was performed at 42° C. Membranes were washed at high stringency as described before.

C. mRNA Expression of the ASA2 gene

Figure 3:
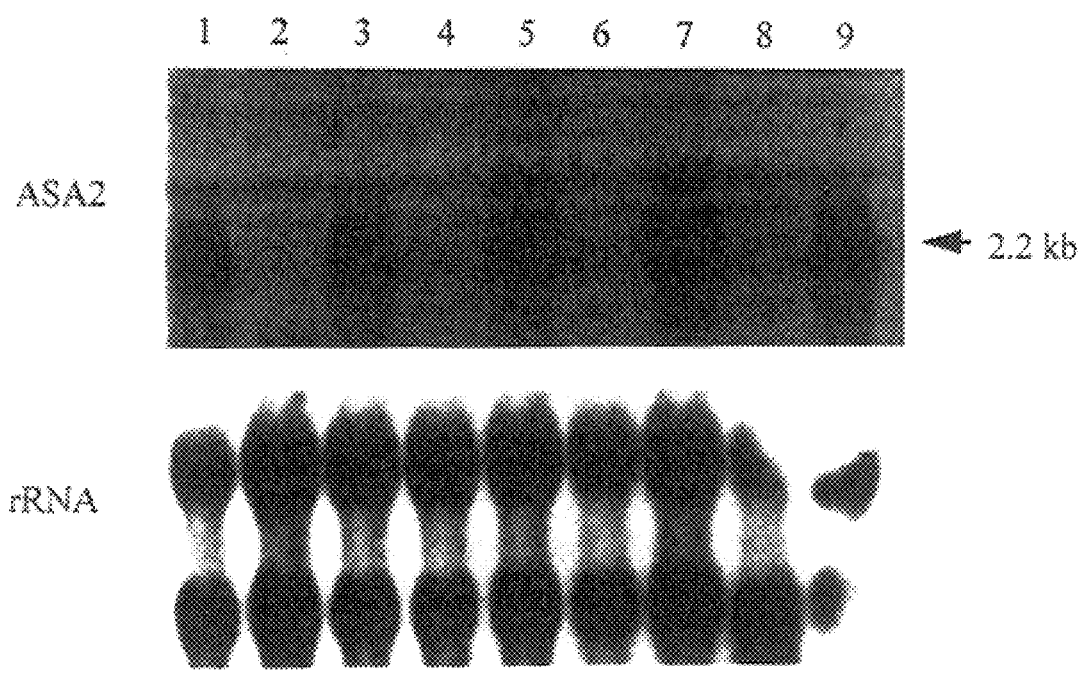
FIG. 3 illustrates mRNA expression of the tobacco AS genes. mRNA expression was detected with the tobacco ASA2 cDNA clone (full-length cDNA) and a ribosomal RNA as probes.

FIG. 3 illustrates mRNA expression of the tobacco AS genes. mRNA expression was detected with the ASA2 cDNA clone. (full-length cDNA described above) and ribosomal RNA as probes. Lane 1, 3, 5, and 7 represent four different 5MT-resistant *N. tabacum* cell lines. Lane 1 and 7 are 5MT-resistant AB15-12-1 cell lines which have been maintained for at least four years in MX medium without 5MT and with 300 $\mu$M 5MT, respectively. Lanes 3 and 5 were recently selected 5MT-resistant tobacco cell lines maintained in 300 $\mu$M 5MT-containing medium. Lane 9 represents a 5MT-resistant *Nicotiana sylvestris* cell line which had been maintained in 300 μM 5MT containing medium for at least one year. Lane 2, 4, and 6 represent three different 5MT-sensitive *N. tabacum* cell lines. Lane 8 represents mRNA extracted from leaves of a plant regenerated from the AB15-12-1 cell line. For these studies, total RNA was isolated from one-week-old suspension cultured cells and leaves harvested from three-week-old seedlings. Ten to 20 μg of total RNA were extracted by using a phenol extraction method, electrophoresed in a denaturing formaldehyde gel, and blotted onto N+-hybond membrane following a general capillary transfer method (McCarty, E. R., 1986, supra, Ausubel et al., 1989, supra, and Sambrook et al., 1989, supra). Northern hybridization and washing of membranes were performed under the same conditions as for Southern hybridization described above (Example 2, Section B).

D. Southern Hybridization

The full-length ASA2 cDNA clone hybridized to multiple bands in AB15-12-1 genomic DNA digested with nine different restriction enzymes (FIG. 2). This result indicated that there was more than one ASA2 like genes in tobacco. This result is understandable, since *N. tabacum* is an allotetraploid.

The tobacco ASA2 cDNA clone hybridized very weakly to Datura and potato DNAs under high stringency conditions (data not shown). These results suggest that it may be possible to select 5MT-resistant cell lines from these plants which may carry similar characteristics to AB15-12-1. It may also be possible to isolate feedback-insensitive AS genes from these plants by using tobacco ASA2 cDNA as probe.

The tobacco full-length ASA2 clone detected an approximately 2.2 kb transcript only in 5MT-resistant suspension cultured cells (FIG. 3). 5MT-sensitive suspension cultured cells and leaves did not show expression of the ASA2 gene at the mRNA level under the condition of overnight exposure of x-ray film with an intensifying screen.

These results indicated that the ASA2 gene may encode a feedback-insensitive AS that was tissue-specific and detected very strongly in only 5MT-resistant tissue cultured cell lines.

E. Amino Acid and Nucleotide Sequence Analysis of the ASA2 Gene

SEQ ID NO: 4 is the ASA2 nucleotide sequence including 5' UTR (nucleotides 1 to 89) and 3' UTR (nucleotides 1941 to 2144). The translation start codon (ATG) begins at nucleotide position 90. The translation stop codon (TAG) ends at nucleotide position 1940. The coding region in SEQ ID NO: 4 corresponds to nucleotides 90 to 1,940. The ASA2 amino sequence is presented in SEQ ID NO: 5 and corresponds to translation of nucleotides 90 to 1940 of SEQ ID NO: 4.

The ASA2 amino acid sequence (SEQ ID NO: 5 and also shown as aligned to SEQ ID NO: 25) was compared to other AS genes from plants and prokaryotes, and the five best matches were chosen based on BLAST analysis (Altshul et al., *J. Mol. Biol.*, 215: 403–410, 1990). An amino acid sequence alignment with these AS genes was performed by using Pileup program (Genetics Computer Group, Wisconsin Sequence Analysis Package) and is shown in FIGS. 4A to 4C. TASA1 (SEQ ID NO: 23, predicted amino acid sequence from the nucleotide sequence of SEQ ID NO: 24), TASA2 (SEQ ID NO: 5), RASA1, RASA2, AASA1, AASA2, and CTRPE correspond to *N. tabacum* ASA1 and ASA2, *Ruta graveolens* ASα1 and ASα2 (Bohlmann, J. et al., *Plant J.* 7(3): 491–501, 1995), *A. thaliana* ASA1 and ASA2 (Niyogi & Fink, 1992), and *Clostridium thermocellum* trpE (Sato, S. et al., *J. Biochem.* 105: 362–366, 1989) cDNA clones, respectively. Dots within sequences indicate gaps. Asterisks represent a perfect match among these seven different AS sequences. Dots under the sequence indicate a perfect match among six plant AS sequences. There was no sequence for *N. tabacum* ASA1 from nucleotides 1 to 125 when aligned in FIGS. 4A to 4C, since a truncated 5' end of the ASA1 cDNA clone was obtained. Even though *N. tabacum* ASA1 cDNA clones (5' and 3' end cDNAs) were not ligated because of a difference of two nucleotides in an overlapping region between 5' and 3' clones, the ASA1 amino acid sequence was used to align in order to compare sequence similarity to other AS genes. These two nucleotides created amino acid $Pro_{243}$ in the 5' clone and $Asn_{243}$ in the 3' clone which is indicated by a plus (+) on the top of the amino acid in FIGS. 4A to 4C. *N. tabacum* ASA2 has a transit peptide sequence (approximately 60 amino acids) downstream of the translation initiation codon which does not have any homology to the transit peptide sequences of other AS genes. Conserved amino acids for feedback sensitivity in AS of other species have not been changed in the *N. tabacum* ASA2 gene, which are indicated by bold letters and asterisks on the top of the amino acids. A single amino acid change in an Arabidopsis AS mutant ($Asp_{341}$ to $Asn_{341}$: indicated by bold letter and underlining in FIGS. 4A to 4C—at position 363 when aligned in the figures) which causes feedback insensitivity (Li & Last, *Plant Physiol.* 110: 51–59, 1996) was not found in the *N. tabacum* ASA2 gene in FIGS. 4A to 4C (SEQ ID NO: 4). However, we have identified two amino acids ($Phe_{107}$ and $Arg_{108}$: indicated by bold letter and underlining in FIGS. 4A to 4C at positions 142 and 143 when aligned in the figure) of the *N. tabacum* ASA2 amino acid sequence in FIGS. 4A to 4C (SEQ ID NO: 5), which possibly affect the Trp binding site in *N. tabacum* ASA2, resulting in feedback insensitivity.

The predicted amino acid sequence of the *N. tabacum* ASA2 gene showed 72%, 68% and 67%, 68% and 61% and 32% and amino acid identity to the *N. tabacum* ASA1, *A. thaliana* ASA1 and ASA2 (Niyogi & Fink, 1992) and *R. graveolens* ASα1 and ASα2 (Bohlmann, J. et al., 1995), and *C. thermocellum* trpE gene (Sato, S. et al., 1989), respectively, while the *N. tabacum* ASA1 cDNA clone exhibits 98% amino acid identity to the Arabidopsis ASA1 (Table 1).

TABLE 1

|       | *TASA1  | TASA2 | RASA1 | RASA2 | AASA1 | AASA2 | CTRPE |
|-------|---------|-------|-------|-------|-------|-------|-------|
| TASA1 | 100 (%) | 72    | 73    | 72    | 98    | 68    | 35    |
| TASA2 | 72      | 100   | 68    | 67    | 65    | 61    | 32    |

F. Complementation and Inhibition Test

1. Construction of ASA2 cDNA in an Expression Vector

The tobacco ASA2 cDNA, from $Ser_{61}$ to the translation stop codon, has been amplified using primer 4 (SEQ ID NO:

6) and primer 5 (SEQ ID NO. 7) containing BamHI and KpnI overhangs, respectively. An expression vector (pQE30 from Qiagen) and the PCR fragment were digested with BamHI and KpnI and ligated in frame as confirmed by sequencing. This construct was named pQES61K.

2. Complementation and Inhibition Tests

FIG. 5 shows a picture of the complementation and inhibition test. The pQES61K was transformed into a trpE nonsense (trpE 5972) mutant *E. coli*. The trpE nonsense mutant *E. coli* (trpE 5972) transformed with an expression vector itself (Vector) and the ASA2 cDNA ligated into the expression vector (ASA2) were plated on the M9 minimal medium containing, isopropyl-thiogalactoside (IPTG, 0.1 mM) and ampicillin (100 µg/ml) and either with Trp (+Trp, FIG. 5A) or without Trp (−Trp, FIG. 5B). The complemented strain grew well on M9 medium without Trp and also with 300 µM 5MT (FIG. 5C) which inhibits the growth of the complemented strain carrying feedback-sensitive plant AS (Bohlmann et al., *Plant Physiol.*, 111: 507–514, 1996). The complementation and inhibition tests suggest that the ASA2 cDNA produces a functional enzyme which is resistant to high concentrations of 5MT. These results support the conclusion that the ASA2 gene is encoding a feedback-insensitive AS enzyme and can be used as a selectable marker. Complementation for the Trp requirement was also obtained with the *E. coli* deletion mutant (ΔtrpE 5390: Leu- and Trp-), which showed the same result as above (data not shown).

3. *E. coli* expression of ASA2 Gene

The tobacco ASA2 gene was expressed in *E. coli* strain trpE5972, a mutant line containing a nonsense trpE gene, grown to late log phase on Luria Bertani medium with 100 µM Trp. Expression was induced by addition of 100 µM isopropylthiogalactoside. A protease inhibitor, 135 µM phenylmethylsulfonylfluoride (PMSF), was added with further incubation for three hours at 30° C., 150 rpm. The cells were collected by centrifugation and resuspended in 50 mM Tris, 5 mM $MgCl_2$, 100 mM $NH_4Cl$, 2 mM dithiothreitol, 20% glycerol, pH 8.0 plus 100 µM PMSF and disrupted using a French press (2 passes, 20,000 psi). Cell debris was removed by centrifugation and the supernatant treated with Ni-affinity resin. Bound protein was eluted with 100 µM imidazole in pH 6.3 buffer. The Arabidopsis ASA1 gene was similarly expressed except that the *E. coli* strain JM109 was used and enzyme activity in a crude cell extract without Ni-affinity purification was characterized.

Enzyme activity was measured with and without Trp in 50 mM Tris, 5 mM M?$gCl_2$, 1 mM EDTA, 100 mM $NH_4Cl$, 2 mM dithiothreitol, 20% glycerol, pH 7.8 plus 100 µM chorismate. Anthranilate produced in; 30 min at 30° C. was extracted using ethyl acetate and fluorescence measured at excitation 340 and emission 400.

Figure 6:
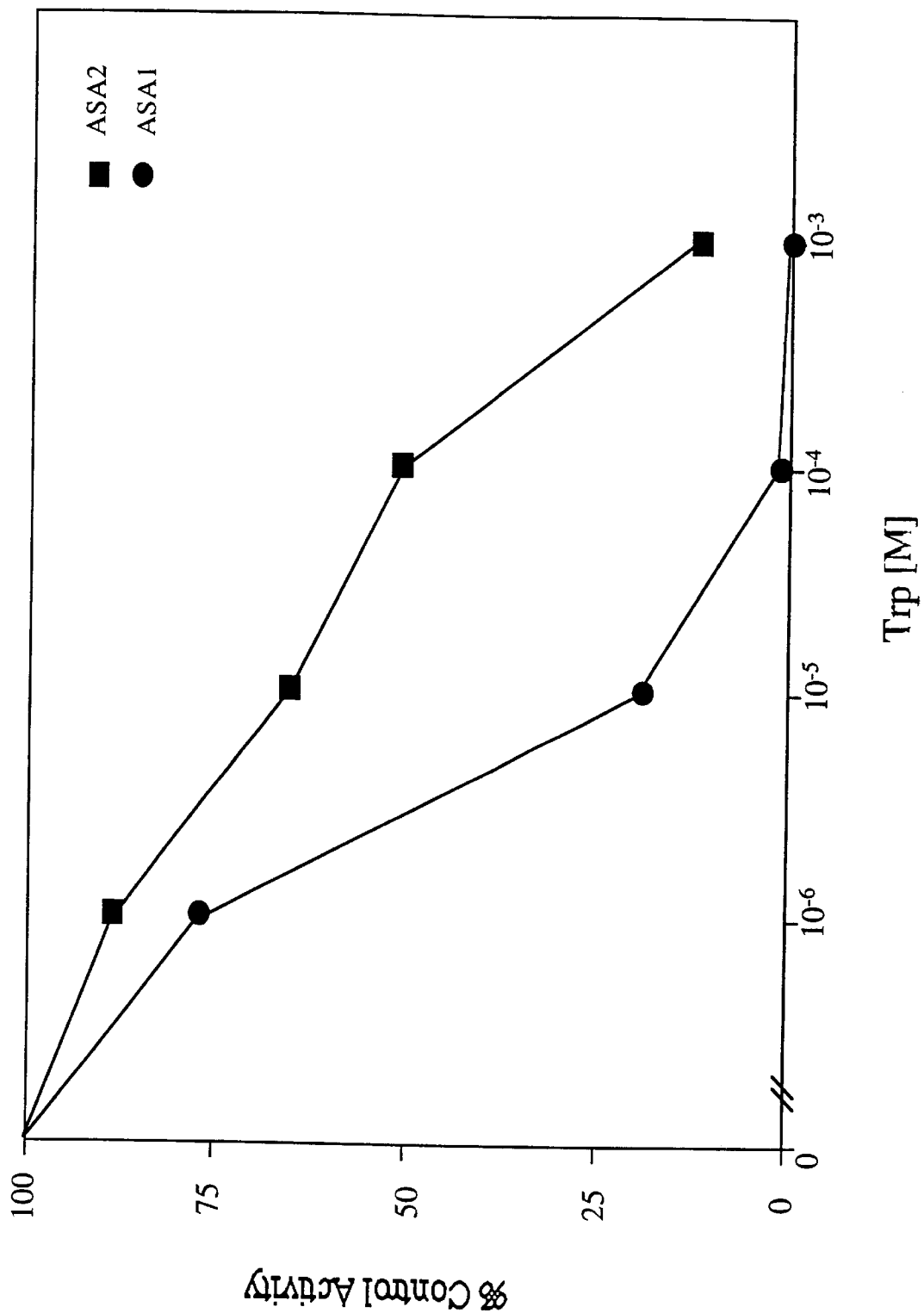
FIG. 6 shows feedback inhibition assay of tobacco ASA2 and Arabidopsis ASA1 activities expressed in E. coli.

FIG. 6 shows that the partially purified ASA2 gene expressed in *E. coli* is still active at 100 µM Trp (50%). The Arabidopsis ASA1 gene product is completely inhibited at this and lower concentrations of Trp. This shows that the ASA2 cDNA does encode an AS α-subunit that is feedback-insensitive.

EXAMPLE 3

Figure 7:
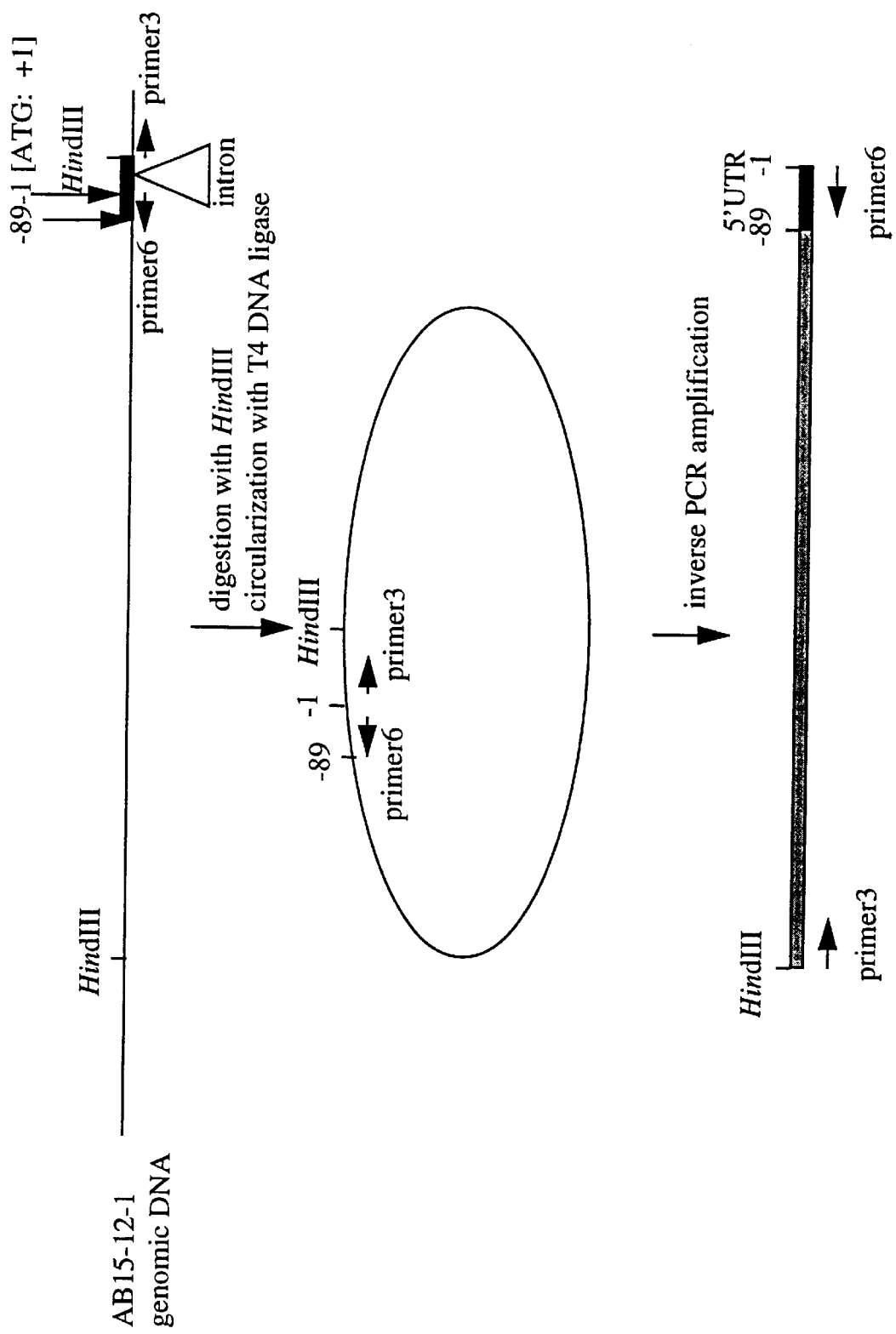
FIG. 7 shows a diagram of the strategy used to isolate the ASA2 promoter DNA sequence.

Construction of ASA2 Promoter-GUS Constructs A. Cloning of the *N. tabacum* ASA2 Promoter The promoter of the *N. tabacum* ASA2 gene was isolated using inverse PCR. FIG. 7 shows a diagram of the strategy used to isolate the ASA2 promoter. The HindIII digested AB15-12-1 genomic DNA was circularized with T4 DNA ligase and used as a template for inverse PCR with primer 3 (SEQ ID NO: 3) and primer 6 (SEQ ID NO: 8). These two primers were designed based on the sequence of the full-length ASA2 cDNA in Example 2 (SEQ ID NO: 4). The thermocycling program was as follows: denaturation at 95° C. for 1 min., annealing at 50° C. for 1 min., and extension at 72° C. for 2 min for 30 cycles. There was an initial 5 min. denaturation at 95° C. prior to beginning the thermocycling program above. Upon completion of the thermocycling program, there was an extension at 72° C. for 10 min. An approximately 2.3 kb fragment strongly hybridized to the full-length ASA2 cDNA clone from Example 2. This was expected since there was a 90 bp overlap between the inverse PCR fragment and the 5' end of the ASA2 cDNA. The sequencing results showed a perfect match in this overlapping region.

B. Construction of ASA2 Promoter-GUS Constructs

Figure 8:
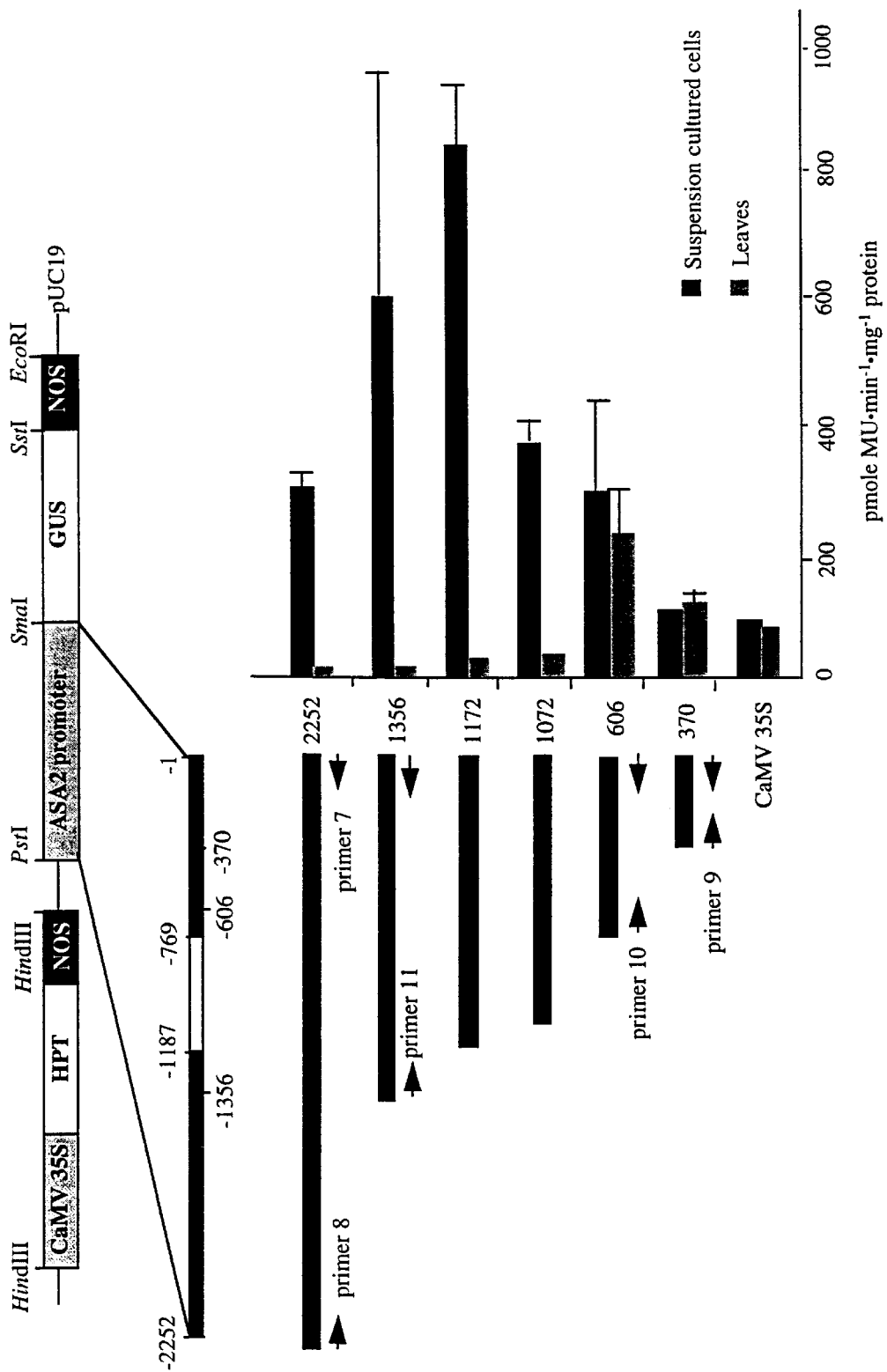
FIG. 8 describes the construction of the ASA2 promoter—GUS reporter gene constructs, and the subsequent deletion analysis of the ASA2 promoter.

FIG. 8 describes the construction of the ASA2 promoter-beta-glucuronidase reporter gene constructs, and the subsequent deletion analysis of the ASA2 promoter. Beta-glucuronidase is abbreviated as GUS. The pBI221 (Clontech- Catalog# 6019-1, Palo Alto, Calif.) vector was used to provide the GUS reporter gene and NOS3' terminator. "NOS" denotes nopaline synthase terminator. A database search. (Find Pattern program for transcription factors) obtained using the Wisconsin Package from the Genetics Computer Group, Inc. (575 Science Dr., Madison, Wis.) showed that there were eight possible TATA boxes in the 2,297 bp fragment. BLAST analysis showed that nucleotide sequences between −769 and −1,187 exhibited 81% identity to the promoter region of the *N. tabacum* plant defense-related str246C gene (Froissard et al., *Plant Mol. Biol.* 26(1): 515–521, 1994) and part of the coding region of organ-specific and auxin-inducible tobacco parA-related gene (Genbank accession number: D42119). Based on these database search results, deletion was performed by using PCR amplification with four sets of primers.

Each primer contained a restriction enzyme site overhang for cloning. Primer 7 (SEQ ID NO: 9) contains. the SmaI site. Primers 8 (SEQ ID NO: 10), 9 (SEQ ID NO: 11), 10 (SEQ ID NO: 12), and 11 (SEQ ID NO: 13) contain the PstI site. The four sets of primers: primers 7 (SEQ ID NO: 9) and 8 (SEQ ID NO: 10); primers 7 (SEQ ID NO: 9) and 9 (SEQ ID NO: 11); primers 7 (SEQ ID NO: 9) and 10 (SEQ ID NO: 12); and primers 7 (SEQ ID NO: 9) and 11 (SEQ ID NO: 13), amplified 2,252 bp, 370 bp, 606 bp, 1356 bp fragments, respectively. These four fragments were cloned into the pBI221 vector in place of the CaMV 35S promoter and were designated 2252, 370, 606, and 1356, respectively (FIG. 8). An additional construct was also prepared in which the hygromycin resistance selectable marker gene (hpt) was ligated into a HindIII site, so that expression of the hpt gene was controlled by the CaMV 35S promoter and the NOS-terminator. All constructed plasmid DNAs were transformed into *E. coli* DH5α and stored at −70° C. with 15% glycerol.

The following describes another ASA2 Promoter-GUS construct. In this construct, the 5' end of the ASA2 promoter fragment (−1356 to −1) has additionally been deleted by using ExoIII nuclease and S1 mungbean nuclease (Stratagene) to determine the specific region which controls tissue-specific expression. The deleted fragments, −1172 to −1 and −1072 to −1 were ligated into pBI221 replacing the CaMV 35S promoter between the HindIII and SmaI sites, designated 1172 and 1072, and GUS expression was determined.

C. Sequence Analysis

The full-length ASA2 promoter was sequenced using standard sequencing methods (Sanger dideoxynucleotide sequence method) of the full-length promoter clone described in Example 3, section A. The sequencing results indicated that an approximately 2.3 kb fragment is the promoter region of the ASA2 gene (FIG. 9; SEQ ID NO: 14), since the sequence of a 89 bp overlapping region between the promoter fragment and 5' upstream of the translation start codon of the ASA2 cDNA (SEQ ID NO: 4) showed a perfect match. The −1 nucleotide position in FIG. 9 corresponds to the nucleotide sequence upstream of the translation start codon (ATG). There were eight possible TATA boxes (−121, −280, −432, −457, −566, −634, −1169, and −2031), one CAAT site (−730), and many transcriptional factor binding sites such as a Pu box (−61 to −66), PEA3 (−62 to −67), AP-1 (−697 to −703) as activator or enhancer motifs. Nucleotide sequences between −769 and −1,187 exhibited 81% identity to the promoter region of *N. tabacum* plant defense-related str246C gene (Froissard et al., 1994), and part of the coding region of the organ-specific and auxin-inducible tobacco parA-related gene (Genbank accession number: D42119). These results indicated that more than one transcript could possibly be transcribed by this promoter region. Si-nuclease assay by hybridizing the 372 bp (−1 to −372) promoter fragment as a single stranded probe against total RNA obtained from the AB15-12-1 tissue culture cells showed more than one band, which supports this conclusion (data not shown). This work will be continued to show clearly which sites are involved in transcription initiation.

D. Expression of the GUS Constructs

1. Transformation. The constructed plasmid DNAs were isolated by using a Plasmid Maxi Kit (Qiagen, catalog # 12162, Chatsworth, Calif.) and transformed into tobacco suspension cells (AB15-12-1 cells) and leaves (from plants regenerated from the AB15-12-1 cell line) using a Particle Inflow Gun (PIG) (1 $\mu$g DNA and 0.5 mg of 1.0 $\mu$m diameter tungsten particles/shot at 80 psi). The sample was incubated at 240° C. (60 $\mu$Em-$^{2}$s-$^{1}$) for 3 days after transformation. The promoter activity was determined by GUS histochemical assay with 5-bromo-4-chloro-3-indoyl glucuronide (X-Gluc) as substrate and by fluorimetric MUG assay with 4-methylumbelliferyl β-D-glucuronide (Jefferson, R. A., *Plant Mol. Biol.* Reporter, 5: 387–405, 1987).

Two chimeric GUS constructs controlled by 2252 and CaMV 35S promoters in a binary vector (pBI101, Clontech) were stably transformed into tobacco plants using *Agrobacterium tumefaciens*, and GUS activity was determined with the transgenic tobacco plants.

2. Expression. Strong transient GUS gene expression controlled by the full-length ASA2 promoter started to appear within one hour of incubation with the substrate (X-Gluc) in tobacco suspension cells (AB15-12-1 cells) bombarded with this clone. Little expression was observed in leaves after 10 to 12 hours incubation. Transformed leaves were extracted with ethanol at 37° C. overnight. The level of GUS gene expression controlled by the CaMV 35S promoter showed no significant difference between cultured cells and leaves. These experiments were repeated and the GUS activity was quantitated by the fluorimetric MUG assay and similar results were obtained (FIG. 8). These results suggest that the ASA2 promoter controls tissue-specific gene expression which was also strongly supported by the results of the ASA2 gene expression at the mRNA level (FIG. 3). In addition, these data indicate that the promoter is very active in cultured cells, and following selection the plants that were regenerated would not express the selectable marker gene at an appreciable level.

Strong transient GUS gene expression in suspension cultured cells especially 5MT-resistant suspension cultured cells has been found in the chimeric GUS constructs 2252, 1356, 1172, and 1072, while comparably low expression has been detected in leaves. The promoter region between −606 to −1 produced similar GUS gene expression in suspension cultured cells and leaves. These results suggest that the region between −2252 to −606 is involved in a tissue-specific gene expression. Transgenic tobacco plants carrying 2252 did not show any GUS activities in most tissues except for restricted epidermal cells in the very young leaves (FIGS. 10A and 10B) and calli induced from the transgenic tobacco leaves, which also supports the hypothesis that the region between −2252 to −606 regulates tissue-specific expression.

E. Strong Constitutive Promoter (−606 to −1) in Dicotyledonous Plants

The transient and stable GUS expression controlled by the three ASA2 deleted promoters (2252, 1356, and 606) and the control promoter (the CaMV 35S promoter), were investigated in several dicotyledonous plants such as Chinese Milk Vetch, *D. innoxia*, *N. sylvestris*, peanut, potato, soybean, tomato, and a monocotyledonous plant such as wheat (Table 2). Different plant tissues of each plant were used for GUS expression, as follows: leaves and suspension cultured cells of *D. innoxia*, roots of Chinese Milk Vetch, leaves and suspension cells (5MT$^s$) and (5MT$^r$) of *N. sylvestris*, embryonal axis of peanut, leaves of potato, embryogenic cells, leaves, and suspension cultured cells of soybean, leaves (wild-type and regenerant from 5MT$^r$ suspension cells), roots, stems, and suspension cells (5MT$^s$ and 5MT$^r$) of tobacco, leaves of tomato, and scutellum of wheat. The 606-GUS construct showed strong constitutive expression in most tissues of dicotyledonous. plants. The 1356-GUS construct showed tissue-specific expression in tobacco and possibly *D. innoxia*, *N. sylvestris*, potato, and tomato which belong to the Solanaceae family, and weak expression in wheat similar to that of the CaMV 35S promoter.

TABLE 2

GUS activity controlled by the ASA2 and CaMV 35S promoters in 9 different plant species.

| Plants | Sources of plant tissues | GUS activity | | | |
|---|---|---|---|---|---|
| | | 606 | 1356 | 2252 | 35S |
| Chinese Milk Vetch | roots | nt | +++* | +* | +++* |
| *D. innoxia* | suspension cultured cells (SC) | +++ | nt | ++ | ++ |
| | leaves | ++ | very low | very low | ++ |
| *N. sylvestris* | 5MT$^s$ SC | ++ | low | low | ++ |
| | 5MT$^r$ SC | ++++++ | ++++++ | ++++ | +++ |
| | leaves (wild type) | +++ | low | low | ++ |
| Peanut | embryonal axis | ++ | ++++ | nt | + |
| Potato | leaves | ++ | + | + | ++ |
| Soybean | SC | ++++ | nt | + | + |
| | embryogenic cells | ++++ | ++ | nt | +++ |
| | leaves | ++++ | nt | ++ | + |
| Tobacco | 5MT$^s$ SC | ++ | + | + | ++ |
| | 5MT$^r$ SC | ++++ | ++++ | +++ | |
| | leaves (wild type) | +++ | low | very low* | +++* |
| | regenerant leaves from 5MT$^r$ SC | +++ | very low | very low | ++ |
| | roots | nt | nt | −* | +++* |
| | stems | nt | nt | −* | +++* |

TABLE 2-continued

GUS activity controlled by the ASA2 and CaMV 35S promoters in 9 different plant species.

| Plants | Sources of plant tissues | GUS activity | | | |
|---|---|---|---|---|---|
| | | 606 | 1356 | 2252 | 35S |
| Tomato | leaves | + | low | low | ++ |
| Wheat | scutellum | − | + | nt | + |

−: no expression,
+ to ++++++: weak to strong expression,
nt: not tested,
*: GUS expression on transgenic plants transformed with different chimeric constructs using Agrobacterium.

EXAMPLE 4

Cloning of the N. tabacum ASA1 and ASA3 Genes

A. Cloning Strategy

Figure 11:
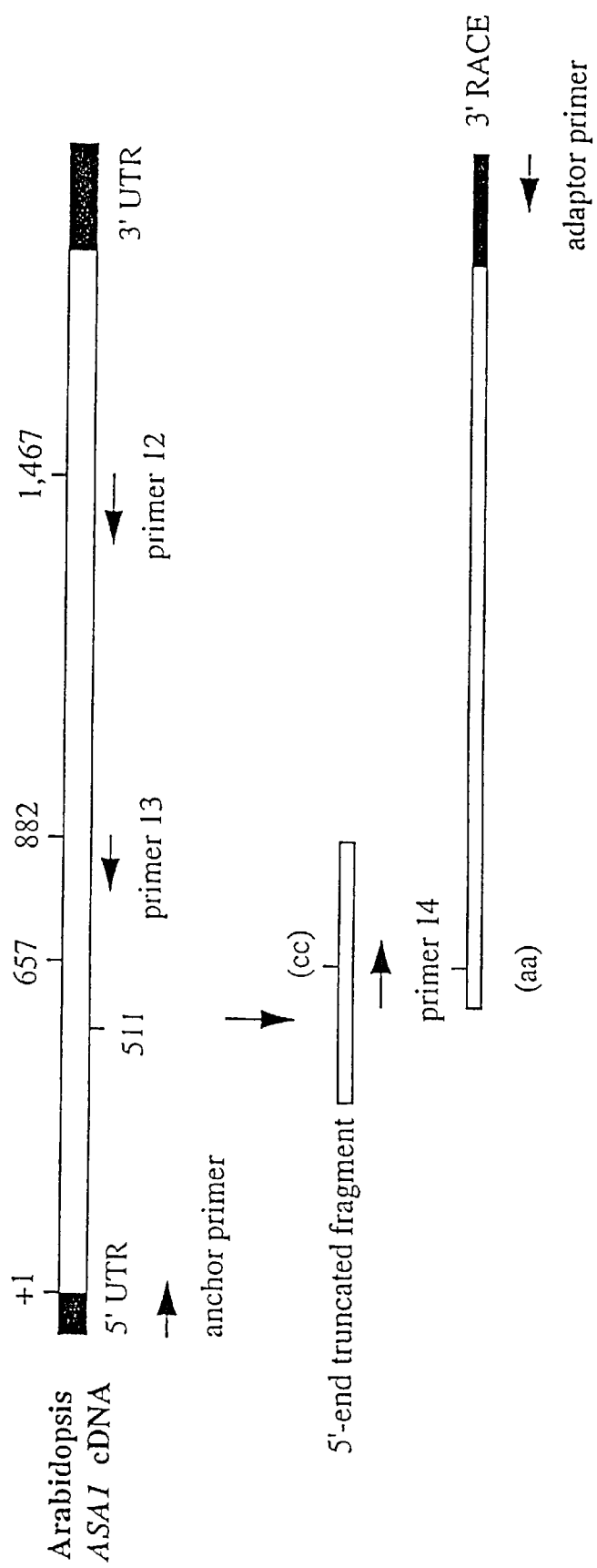
FIG. 11 shows a diagram of the A. thaliana ASA1 cDNA. The A. thaliana ASA1 cDNA sequence was used to design degenerate primers to clone the N. tabacum ASA1 gene (5' end truncated) The direction of the arrows, numbers, and black and white bars represent orientation of primers, nucleotide sequence of 5' end of primers, 5' and 3' UTR, and an overlapping region between the 5' and 3' clones, respectively.

The N. tabacum ASA1 cDNA (5' fragment), ASA1 cDNA (3' fragment), ASA1 genomic, and ASA3 partial genomic clones were obtained by using 5' and 3' RACE, genomic library screening, and PCR amplification, respectively. FIG. 11 shows a diagram of the N. tabacum ASA1 cDNA. The A. thaliana ASA1 cDNA amino acid sequence was used to construct heterologous primers to clone the N. tabacum ASA1 gene (5' end truncated). The N. tabacum ASA1 cDNA was also isolated by using 5' and 3' RACE. All procedures including the PCR reaction were exactly the same as those described for cloning the N. tabacum ASA2 gene (Example 2). The 5' end cDNA was isolated with degenerate primer 12 (SEQ ID NO: 15). The sequence of primer 12 was based upon the predicted amino acid sequence of the A. thaliana ASA1 gene. Primer 13 (SEQ ID NO: 16) was used for nested PCR to produce an approximately 0.6 kb 5' end truncated clone. Primer 14 (SEQ ID NO: 17) was used to isolate an approximately 1.4 kb fragment of the 3' end of the ASA1 cDNA clone. Both fragments were cloned into a commercially available pGEM-T vector (Promega) and sequenced by the Genetic Engineering Lab at the University of Illinois, using the Sanger dideoxynucleotide sequencing method (SEQ ID NO: 24).

Figure 12:
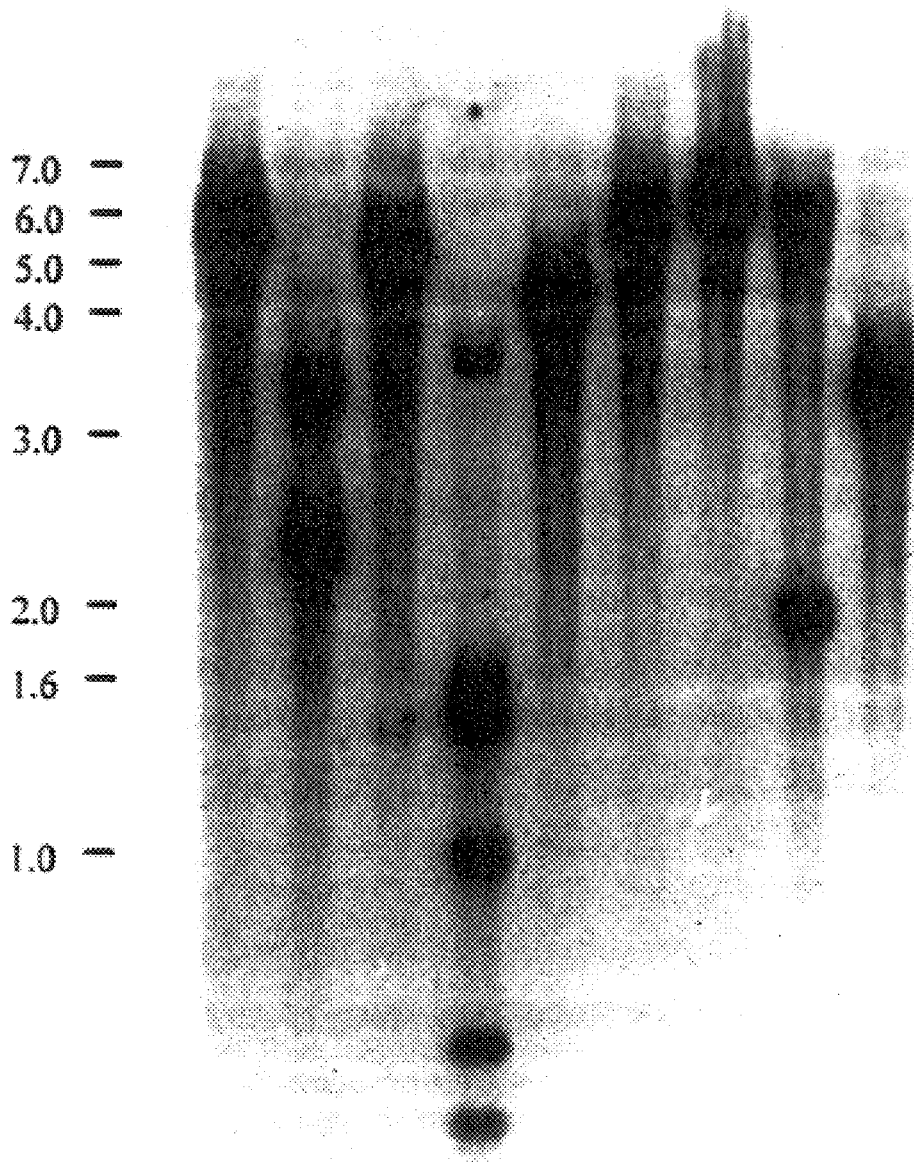
FIG. 12 is a Southern hybridization using a four kb PstI fragment of the ASA genomic clone as a probe to determine how many ASA genes exist in the tobacco genome.

The tobacco genomic ASA clone was obtained by screening a wild-type N. tabacum genomic library (Clontech, 5×10⁵ pfu/ml—catalog # FL1071d, Palo Alto, Calif.). This genomic library screening was done before cloning the N. tabacum ASA2 gene, therefore, A. thaliana ASA1 and ASA2 cDNA clones were used as probes. A total of 18 positive colonies were selected. Only one colony seems to contain an AS gene which was supported by PCR amplification (data not shown). The N. tabacum ASA genomic clone (approximately 7 kb) was digested with SalI and cloned into pBluescript SK−. A four kb PstI fragment of the ASA genomic clone was used as a probe to determine how many ASA genes exist in the tobacco genome by using Southern hybridization (FIG. 12). Sequencing will be necessary to prove whether or not this clone is an ASA gene.

Figure 13:
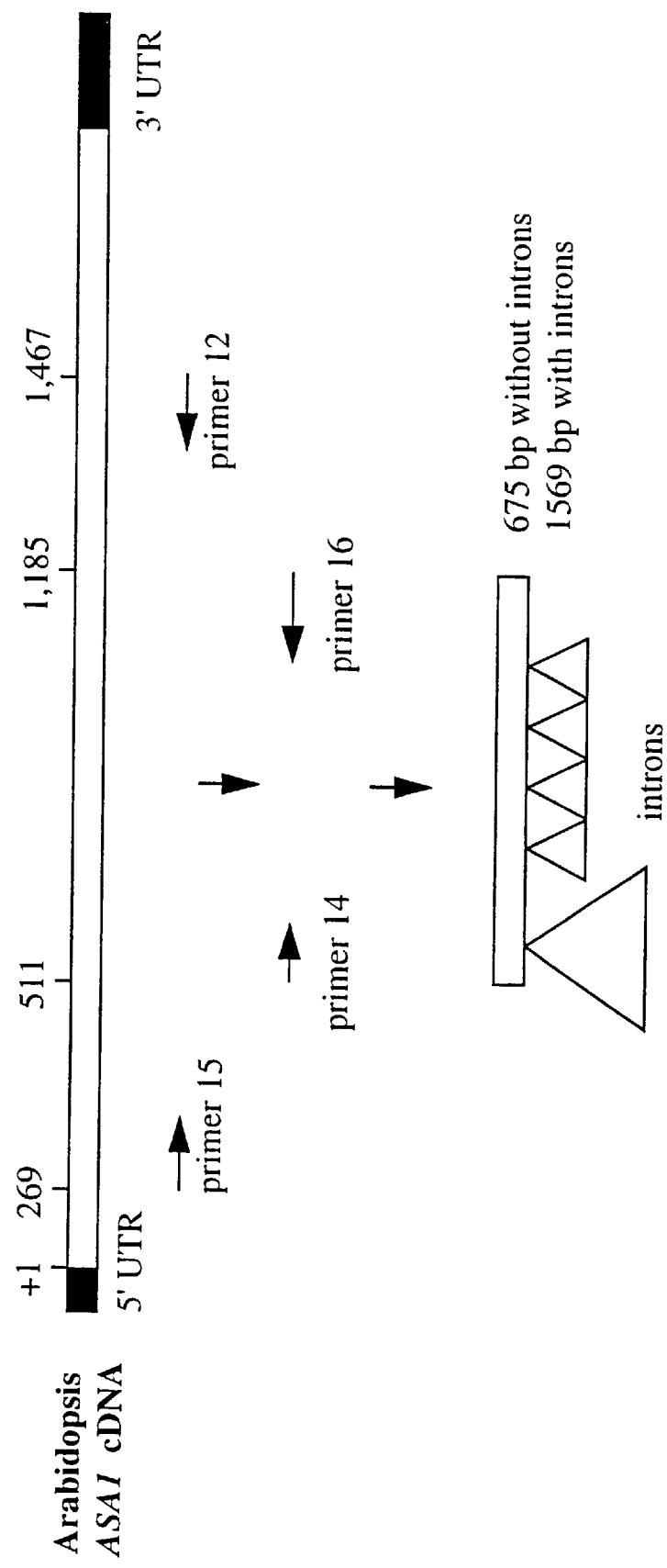
FIG. 13 shows the strategy for nested polymerase chain reaction (PCR) amplification used to isolate tobacco partial genomic DNAs by PCR amplification with primer 15 (SEQ ID NO: 18) and primer 12 (SEQ ID NO: 15), primer 14 (SEQ ID NO: 17) and primer 16 (SEQ ID NO: 19). These degenerate primers were designed based on the amino acid sequence predicted from the nucleotide sequences of the A. thaliana ASA1 gene.

Tobacco partial genomic DNAs, with and without intron (s), were isolated by using PCR amplification with degenerated primers: primer 15 (SEQ ID NO: 18) and primer 12 (SEQ ID NO: 15), primer 14 (SEQ ID NO: 17) and primer 16 (SEQ ID NO: 19) for nested PCR (FIG. 13). These degenerated primers were designed based on the predicted amino acid and nucleotide sequences of the A. thaliana ASA1 gene, respectively.

Figure 14:
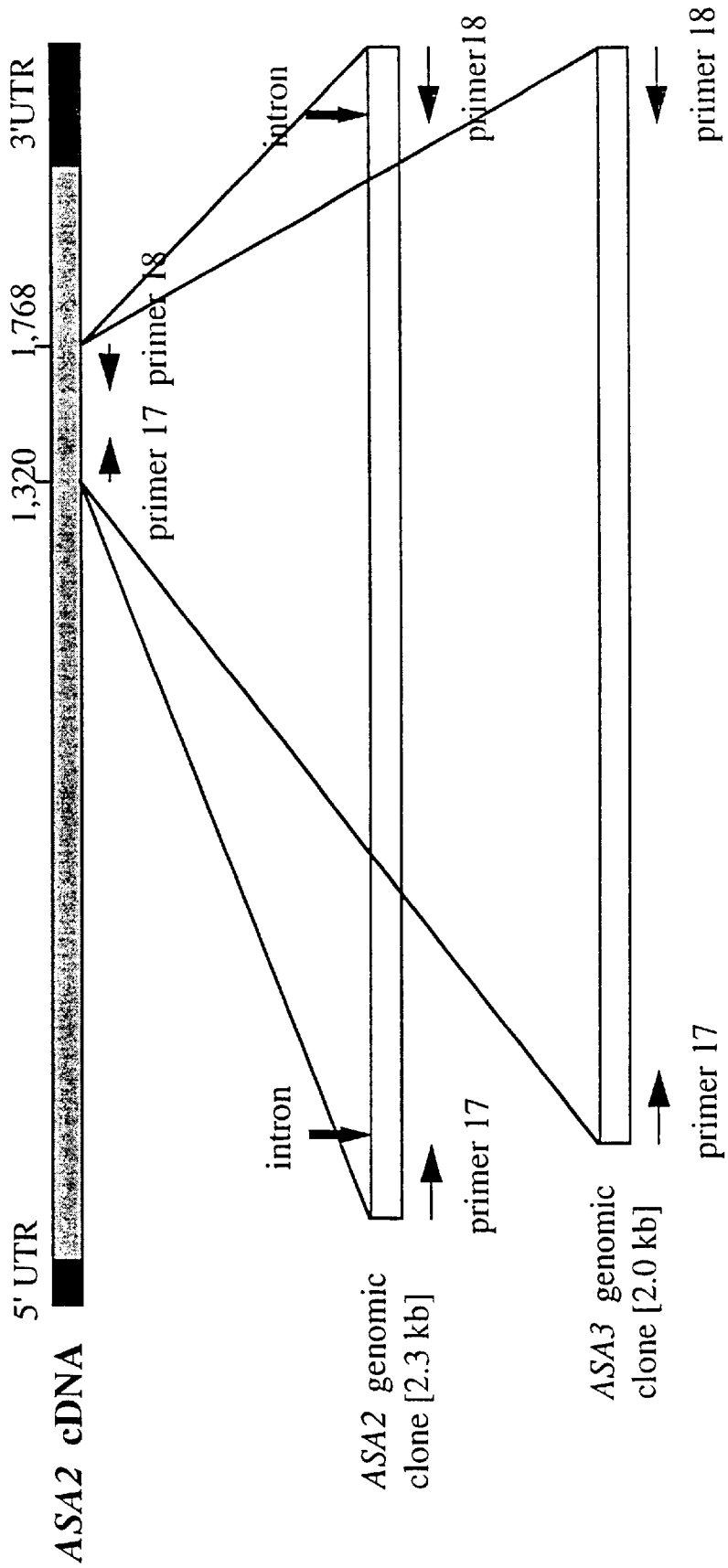
FIG. 14 shows the strategy of how N. tabacum ASA2 and ASA3 partial genomic clones were obtained by PCR amplification with primer 16 (SEQ ID NO: 19) and primer 17 (SEQ ID NO: 20) with AB15-12-1 genomic DNA as a template.

N. tabacum ASA2 and ASA3 partial genomic clones were obtained by PCR amplification with primer 17 (SEQ ID NO: 20) and primer 18 (SEQ ID NO: 21) with AB15-12-1 genomic DNA as a template (FIG. 14). The annealing temperature was 55° C. for 1 min. in 30 cycles. The final composition of the PCR reaction and the reaction conditions were the same as described in Example 2, section B. Two fragments (2.0 kb and 2.3 kb) were amplified that strongly hybridized to the ASA2 clone. These fragments were cloned into pGEM-T vector, and sequenced.

B. Sequence Analysis of the ASA Genes

We have isolated one 5' end truncated ASA1 cDNA, one ASA genomic, one full-length ASA2 cDNA, and one partial ASA3 genomic clones. These AS genes encode the α-subunit of AS in tobacco (ASA). We have also cloned AS genes without introns. Both ASA1 genes probably encode feedback-sensitive AS, but characteristics of both genes are different at the mRNA level such as size of transcript and tissue-specificity. The ASA genomic clone hybridized to a single band for most restriction enzyme digestions, which indicates that this ASA gene is different from the ASA1 cDNA clone (FIG. 12). Tobacco ASA1 cDNA showed 98% amino acid identity to A. thaliana ASA1. Even though tobacco and Arabidopsis are not closely related phylogenetically, we could isolate partial ASA1 cDNA and genomic clones with and without intron(s) from N. sylvestris, N. tomentosiformis, and N. tabacum, which showed almost 98% identity to Arabidopsis ASA1 (data not shown). Based on these results, the ASA1 gene is a more conserved AS gene among different plant families or orders than is the ASA2 gene.

The ASA2 gene may encode a feedback-insensitive AS based on gene expression at the mRNA level (FIG. 3), feedback inhibition characteristics (FIG. 6) of the gene product expressed in E. coli, and ASA2 promoter activity with GUS constructs (Example 3). ASA3 may be another ASA2-like gene which originated from the other parent, since N. tabacum is an allotetraploid between N. sylvestris and N. tomentosiformis. The partial sequence between the ASA2 and ASA3 genomic clones (ASA2G, ASA3G) showed approximately 85% (56 nucleotides mismatch out of 657) nucleotide identity to each other (FIGS. 15A and 15B). We need to complete cloning and sequencing of the rest of the ASA3 gene (SEQ ID NO: 22). It is possible that the size of both transcripts is very similar, since we found only one transcript size detected by the ASA2 cDNA clone. It is necessary to check Northern hybridization with the ASA3 clone as a probe to determine whether or not the ASA3 gene may also encode a feedback-insensitive AS that has a transcript of size similar to that of ASA2.

EXAMPLE 5

Use of the ASA2 Promoter to Drive Different Selectable Markers

A. Possible: Expression Constructs

The 2.3 kb ASA2 promoter fragment (SEQ ID NO: 14) can be attached to many possible selectable markers including the ASA2 structural gene (SEQ ID NO: 4) that should impart resistance to 5MT, to the-neomycin phosphotransferase II gene that should impart resistance to kanamycin, to the hygromycin phosphotransferase gene that should impart resistance to hygromycin and to the phosphinothricin-acetyl transferase gene that should impart resistance to phosphinothricin (Basta).

B. Transformation

Once the promoter and selectable marker gene with a suitable terminator sequence are assembled in a plasmid the construct can be used to transform plant cells using any of the possible transformation systems including particle bombardment of cells or tissues, electroporation of protoplasts or cells and Agrobacterium mediated transformation if the construct is placed into correct plasmid in the bacterium.

C. Utility of the ASA2 Promoter and ASA2 Structural Gene

The use of the ASA2 structural gene as a selectable marker would provide a new selectable marker for use in selecting transformed cells from the mass of untransformed cells. An effective selectable marker is required since the transformation process is relatively inefficient.

The use of the ASA2 promoter to drive any of the possible selectable markers should allow selection for the resistance marker in cultured cells, but not in the regenerated plant. This is because the promoter is very active in cultured cells (see Example 3, Section C), but following selection the plants that are regenerated will not express the selectable marker gene at an appreciable level. This lack of expression at the whole plant level will blunt any arguments that expression in the plants will cause environmental harm or that expression of the selectable marker gene will have a detrimental effect on the plant itself.

EXAMPLE 6

Expression of the N. tabacum ASA2 Promoter and ASA2 Structural Gene in Different Plant Species A. Expected Expression Patterns The N. tabacum ASA2 promoter and structural gene were isolated from the dicot N. tabacum, where the characteristics described of tissue culture specificity imparted by the promoter (see Example 3) and very clear resistance to 5MT imparted by the ASA2 structural gene (see Example 1) have been demonstrated. It is expected that the 5MT resistance carried by the structural gene would be expressed in other plant species (both monocot and dicot), since the AS genes are conserved and the alteration in the sequence should provide resistance. The expression characteristics of the promoter are less predictable.

B. Strategy for Construction of Vectors for Expression

To test the expression of the N. tabacum ASA2 promoter and structural gene in different plant species, we will use the following constructs to transform cell cultures of N. tabacum, carrot, D. innoxia, corn, Astragalus sinicus (hereinafter referred to as "A. sinicus"), and soybean using the optimum transformation protocol for each plant species. The following constructs will be tested: (A) The ASA2 promoter driving the ASA2 gene (cDNA clone; A.T.C.C. Accession Number 209150), (B) the ASA2 promoter driving the nptII gene, (C) the CaMV 35S promoter driving the ASA2 structural gene, and (D) the CaMV 35S promoter driving the nptII gene as a control. Following DNA introduction, the transformed cells will be selected with the suitable agent and the selected transformed cells regenerated into plants. The expression of the selectable marker gene will be determined in the cultured cells and in the regenerated plants. Untransformed controls will be used for comparison. The expected results are shown in Table 3.

TABLE 3

| | Expected outcome | | | |
|---|---|---|---|---|
| | Resistance in Cells | | Expression in Plants | |
| Construct | 5MT | Kanamycin | ASA2 | nptII |
| A. ASA2 promoter-ASA2 | + | − | − | − |
| B. ASA2 promoter-nptII | − | + | − | − |
| C. CaMV35S-ASA2 | + | − | + | − |
| D. CaMV35S-nptII | − | + | − | + |
| untransformed control | − | − | − | − |

C. Construction of the ASA2 promoter fused to ASA2 cDNA

The ASA2 cDNA from ATG [+1] codon to +2072 including 3' UTR was amplified with primers containing SmaI site at 5' (primer 19, SEQ ID. NO: 26) and EcoRI site at 3' (primer 20, SEQ ID NO: 27). Both chimeric construct plasmids, ASA2 promoter-GUS, and the ASA2 cDNA PCR product were digested with both SmaI and ECoRI. The ASA2 cDNA fragment was inserted in place of the fragment containing a GUS gene and NOS 3' terminator in the chimeric construct plasmids with the different sizes of the deleted ASA2 promoters. The construct such as CaMV 35S promoter-ASA2, was constructed using the same method as above. In order to fuse other selectable marker genes into the ASA2 promoter, the selectable marker gene including terminator was amplified with primers containing restriction enzyme sites which do not exist in promoter, gene, or terminator sequences. The PCR fragment can be ligated downstream of the ASA2 promoter. These constructs can be transformed by either using Agrobacterium, a biolistic bombardment, or protoplasts electroporation as described above.

EXAMPLE 7

Determination of Amino Acid Residues Involved in Feedback Inhibition

Several regions of the AS amino acid sequence have been shown to affect feedback inhibition (Bohlmann et al., 1996, supra; Kreps, et al., 1996, supra; and Li & Last, 1996, supra). In the tobacco ASA2 of the present patent application, two amino acids, $Phe_{107}$ and $Arg_{108}$ in the same region as that found in Ruta graveolens ASα1 ($Arg_{138}$ for $Gln_{138}$, based on ASα1 amino acid sequence) are shown to be different from those in feedback-sensitive AS which are $Ser_{107}$ and $Gln_{108}$. To determine if $Phe_{107}$ and $Arg_{108}$ residues cause feedback insensitivity, the following site-directed mutagenesis was performed by changing the $Phe_{107}$ and $Arg_{108}$ residues to $Ser_{107}$ and $Gln_{108}$ as found in feedback-sensitive AS.

Site-Directed Mutagenesis and Complementation/Inhibition Tests

Site-directed mutagenesis was performed by PCR using a primer containing mismatch nucleotide sequences by changing four of the original nucleotides (CCTGGTTTTCGA) to (CCCGGGTCTCAA). The first two mismatch nucleotides do not change the amino acid codon, $Pro_{105}$ and $Gly_{106}$ but create a SmaI site. The last two mismatch nucleotides change $Phe_{107}$ and Arg108 to $Ser_{107}$ and $Gln_{108}$. Two PCR products were obtained using primers identified as SEQ ID NO. 28 (5'-ACTAGTGGATCCTGCCTTCACTCTTCATCTCTAG-3, BamHI overhang) and SEQ ID NO. 29 (5'-ACCTTGAGACCCGGGTTCAACGGATTCAAAGAGAAAGCTTGG-3', SmaI overhang); and SEQ ID,NO. 30 (5'-TCCGTTGAA CCCGGGTCTCAAGGTTCTAGTGTTGGTCGCTAC-3', SmaI overhang), and SEQ ID NO. 31 (5'- TTGCGG GGTACCCTAGTTTCTTTTCTCATGTAC-3', KpnI overhang). These two PCR fragments were ligated followed by SmaI digestion and then ligated in frame into the pQE30 vector after double digestion with BamHI and KpnI.

Figure 16:
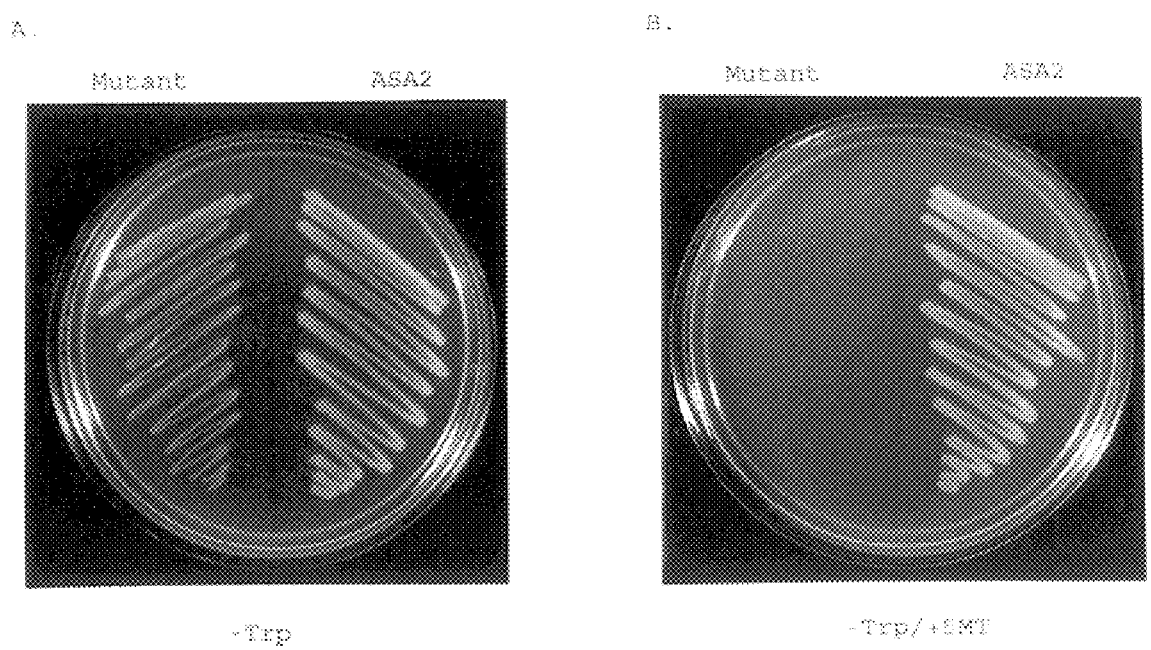
FIG. 16 shows the complementation of E. coli trpE5972 by the tobacco. ASA2 and its site-directed mutants which were plated onto M9minimal medium containing ampicillin. (100 $\mu$g/ml) and isopropylthiogalactoside (0.1 mM) without 300 $\mu$M 5MT (FIG. 16A), and with 300 $\mu$M 5MT (FIG. 16B).

The chimeric constructs were transformed into trpE mutant E. coli (trpE5972, nonsense mutant) using $CaCl_2$ transformation (Sambrook et al., 1989, supra). Complemented strains were plated on M9 minimal medium containing ampicillin (100 μg/ml) and isopropylthiogalactoside (IPTG, 0.1 mM), but no Trp. For the inhibition test, 300 μM 5MT was added to the minimal medium described previously. FIGS. 16A and 16B were taken two days after streaking.

Results of Complementation and Inhibition Tests

The E. coli trpE5972 nonsense mutant transformed with the tobacco ASA2 cDNA and site-directed mutant ($Phe_{107}$, $Arg_{108}$ changed to $Ser_{107}$, Gln,108) both grew on minimal medium containing ampicillin and IPTG but no Trp (FIG. 16A). However, the complemented strain transformed with the site-directed mutant did not grow on the 300 μM 5MT-containing minimal medium without adding Trp (FIG. 16B), while the growth of the strain transformed with the ASA2 cDNA was not inhibited by 300 μM 5MT.

The results presented here support the conclusion that the ASA2 cDNA encodes the α-subunit of a feedback-insensitive AS in tobacco and the $Phe_{107}$ and $Arg_{108}$ residues are especially important in the control of feedback inhibition.

EXAMPLE 8

Use of the Tobacco Feedback-insensitive Anthranilate Synthase Gene (ASA2) as a Plant Transformation Selectable Marker The feedback-insensitive ASA2 cDNA gene, isolated from a 5MT-resistant tobacco cell line, was placed under the control of the constitutive cauliflower mosaic virus 35S promoter and introduced into the legumes: A. sinicus (see Section A, below) and soybean (see Section B, below), and the 35S-ASA2 gene construct was expressed effectively and constitutively in both.

A. A. sinicus

A. sinicus hairy root lines transformed with the 35S-ASA2 gene construct grow in concentrations of up to 100 μM 5MT, while the growth of untransformed control hairy root lines was inhibited by 10–20 μM 5MT and no growth was observed with 30 μM or higher 5MT. Transgenic root lines exhibited a 1.2 to 5.3-fold increase in free Trp. The apparent $K_1$ values for Trp, estimated from the Trp concentration causing 50% inhibition of anthranilate synthase activity in crude extracts, were 4, 5, 16 and 30 μM for the ASA2 transformed lines, and 2 and 3 μM for the controls. Effective direct selection of 35S-ASA2 transformed roots was also achieved at low 5MT concentrations (15–40 μM). Thus, transformation of A. sinicus hairy root lines with ASA2 increases the free Trp concentration and makes the roots resistant to 5MT showing that ASA2 could be a useful selectable marker in plant transformation systems.

1. MATERIALS AND METHODS (i) Construction of Chimeric 35S Promoter-ASA2 Vector

Two oligonucleotides, 5' CGA TTG GAT CCA TGC AGT CGT TAC CTA 3' (SEQ ID NO: 32) and 5' CAG CCG GAA TTCCCA AAT TGC TGA TGG CAT 3' (SEQ ID NO: 33) (the start codon is bolded) containing BamHI and EcoRI overhangs respectively (underlined), were synthesized and used for PCR amplification of full template (Song, H. S., et al., Plant Physiol. 117: 533–543, 1998, which is herein incorporated by reference in its entirety. The cloning and characterization of ASA2 gene is also disclosed in Example 2, above.) with pfu DNA polymerase. PCR amplification was performed for 30 cycles (95° C., 1 min; 50° C., 40 s; 72° C., 2 min). The amplified fragment was digested with BamHI and EcoRI and this fragment used to replace the gfp4 gene of binary vector pBIN-GFP4 (Haseloff et al., Proc. .Natl. Sci. Acad.USA. 94: 2122–2127,1997) to create pBIN-ASA2. The chimeric construct, was transformed into E. coli DH5α using $CaCl_2$ transformation (Sambrook, J., et al., Molecular Cloning: A Laboratory Manual, 1989, supra).

The Agrobacterium rhizogenes (hereinafter referred to as "A. Rhizogenes") strains DC-AR2 (Cho, H.-J., et al., Plant Sci. 138:53–65, 1998) and K599 (Savka, M. A., et al., Phytopathology 80:503–508, 1990) were grown at 28° C. in LB medium to an OD6000=0.5–0.7, the cells were collected by centrifugation (5800×g for 10 min) at 4° C., washed three times in 300, 150 and 6 ml cold 10% (v/v) glycerol, and finally resuspended in 3 ml 10% glycerol and stored as 0.2 ml aliquots at −70° C. For electroporation, 200 μl of cells were mixed with 40 ng of binary plasmid DNA and transferred to a disposable chamber with a 0.2 cm gap and electroporated in a Bio-Rad Gene Pulser TM (Bio-Rad Laboratories, Richmond, Calif., USA). A single pulse of 14.5 KV $cm^{-1}$ initial voltage using the 25 μF capacitor was applied immediately. After electroporation, the chamber was rinsed with 0.8 ml LB medium, and the cells were collected in a sterile tube, incubated with agitation for 1 h at 28° C. and plated on LB agar solidified (1.2% w/v) medium containing 150 μg/ml kanamycin. After incubation at 28° C. for 48 h, colonies were picked, and DNA extracted from randomly selected clones was analyzed using restriction enzymes.

ii) Plant Materials and Transformation

Plantlets of A. sinicus were grown under axenic conditions as described previously (Cho et al., 1998, supra). A 20 ml culture of A. rhizogenes K599 and DC-AR2 strains with binary vector pBIN-ASA2 were grown on LB medium containing 150 μg/ml kanamycin, and A. rhizogenes lacking the binary vector were grown in LB medium without any antibiotic.

Four to seven day old seedlings of A. sinicus with roots removed were then fully immersed in the 1 day cultured bacterial suspension in a petri dish for 10 min, wiped with sterilized filter paper and then placed on partially water immersed filter paper and incubated under 16 h light (45 pmol m-2 s-1, cool white fluorescent lamps). Three days after co-cultivation, plants were transferred to Murashige and Skoog (Murashige, T., & Skoog, F. Physiol. Plant. 15:473–497, 1962), MS, medium solidified with 3g/l Gellan Gum containing 500 mg/l of carbenicillin disodium and 75 mg/l kanamycin.

(iii) Measurement of Growth

Hairy roots were weighed to determine fresh weight, and these samples were dried for 12 h at 750° C. before dry weight determination.

(iv) PCR Screening

PCR was performed on a PTC-100TM Programmable Thermal Controller (MJ Research, Inc.) with DNA extracted from hairy root tissues (150–300 mg) according to the methods of Dellaporta [Dellaporta, S., "Plant DNA miniprep and microprep", Pgs. 522–525 in: The Maize Handbook. M. Freeling & V. Walbot, eds. Springer-Verlag, New York, Inc. (1994)]. The primers used for amplification of a 1107 bp fragment of the ASA2 cDNA gene were 5' CTG CAG CAA TTC ATG CAG TCG TTA CCT ATC 3'(SEQ ID NO: 34) and 5' CTT CCC TCT TCT GCT TGT CCC 3' (SEQ ID NO: 35), and those used for amplification of a 409 bp fragment of the nptII gene were 5' ATC TCA CCT TGC TCC TGC 31 (SEQ ID NO: 36) and 5' ATA CCG TAA AGC ACG AGG 3' (SEQ ID NO: 37). The PCR reaction mixture consisted of 5 μl (100–200 ng) of plant DNA, 2.5 μl of 10×Taq buffer, 1.25 μl of 50 mM MgCl$_2$, 0.25 μl of Taq DNA polymerase (5U/ml, GIBCO BRL), 0.5 μl of 10 mM dNTPs, 0.5 μl each of 10 μM primers and 15 μl of sterile distilled water. Samples were heated to 95° C. for 5 min, followed by 29 cycles of 95° C. (1 min), 57° C. (40 s), 72° C. (90 s) and then 72° C. for 10 min. Amplified products were detected by UV light fluorescence (302 nm) after electrophoresis on 1.0% agarose gels and staining with ethidium bromide.

(v) Nucleic Acid Analysis

Genomic DNA was isolated from 1-week-old suspension cultured cells and 1-month-old hairy root cultures using the CTAB extraction method according to Rogers et al. (*Plant Mol. Biol.*, 5:69–76, 1985), and further purified by CsCl ethidium bromide density centrifugation (Sambrook, J., et al., *Molecular Cloning: A Laboratory Manual*, 1989, supra). Total RNA was prepared using a phenol-extraction method (Wang, C. S., et al., *Plant Physiol.* 105:739–748, 1994) from 1-week-old suspension cultured cells and 1-month-old hairy root cultures. DNA and RNA gels were blotted onto a nylon membrane (Hybond-N+, Amersham) following a general capillary-transfer method and cross-linked to the membrane by UV Stratalinker. The, *N. tabacum* ASA2 cDNA fragment was used as a probe following labeling with a Megaprime DNA labeling system (RPN1605, Amersham) with [α-$^{32}$P] dCTP (3000 Ci/mmol). Filters were prehybridized in 5×SSC, 5× Denhardt's solution, 0.5% SDS, 20 mg/ml denatured salmon sperm DNA at 60° C. and subsequently hybridized overnight with labeled probe. The membranes were washed at high stringency twice at room temperature with 2×SSC and 0.5% SDS for 20 min each time and at 65° C. with 0.1×SSC and 0.1% SDS until the background signal disappeared and then exposed to radiographic film at −70° C. overnight with an intensifying screen.

(vi) Free Trp Analysis

Tissue samples were frozen in liquid nitrogen and stored at −70° C. until analyzed. Samples were ground frozen into a coarse powder and approximately 100 mg of tissue homogenized with 0.1 N HCl (2 ml/g tissue) in a microfuge tube using a plastic pellet pestle (Kontes Glass Co., Vineland, N.J.). The sample was then frozen in liquid nitrogen, thawed and microfuged to sediment debris. A portion of the supernatant was deproteinated using an UltraFree-MC (10,000) filter unit (Millipore Corp., Bedford, Mass.) according to the manufacturer's directions. The filtrate was further diluted with 0.1 N HCl as necessary (1:10 for most samples) and 10 μl analyzed by high performance liquid chromatography, using a 250×4.6 mm Adsorbosil C$_{18}$ column (Alltech Associates, Inc., Deerfield, Ill.), an isocratic buffer system (85%: 140 mM sodium acetate, 17 mM triethylamine, adjusted to pH 5.05 using phosphoric acid, and 15%: 60% acetonitrile in water; 1 ml/min), and fluorescence detection (Kratos FS970; excitation: 215 nm, emission: band pass filter >375 nm). The fluorescence detection method used was similar to that developed by Berardino et al. (Berardino, M. B., et al., *J. Nutr. Biochem.*, 1: 220–222, 1990), except our buffer system was adapted from an unrelated method (Cohen, S. A., et al., *Anal. Biochem.*, 211: 279–287, 1993).

(vii) AS Activity

Extracts were prepared using a Tenbroeck tissue grinder (Kontes Glass Co., Vineland, N.J.), and the ASA1 extraction buffer (2 ml/g tissue) described by Bernasconi and coworkers (Bernasconi, P., et al., *Plant Physiol.*, 106: 353–358, 1994). After removal of cellular debris by centrifugation (10 min at 35,000 × g and 4° C.), one volume of the supernatant was combined with two volumes of room temperature saturated (NH$_4$)$_2$SO$_4$, and then centrifuged as before. The resulting pellet was resuspended in extraction buffer (1 ml/g tissue) and used immediately. When glutamine was used as the second substrate for the AS catalyzed reaction, the resuspended enzyme solution was desalted using Sephadex G25 to remove residual (NH$_4$)$_2$SO$_4$.

AS activity was measured as described in Song et al. (1998, supra) except the assay buffer was that described by Bernasconi et al. (1994, supra) without NH$_4$Cl in the buffer. Either 100 mM NH$_4$Cl or 10 mM glutamine was added to the assay mixture to determine α-subunit activity or AS holoenzyme activity, respectively.

Protein concentration was determined using a protein dye-binding assay kit (Bio-Rad).

2. RESULTS (i) Nucleic Acids Analysis of Transgenic *A. sinicus* Hairy Roots

Figure 17:
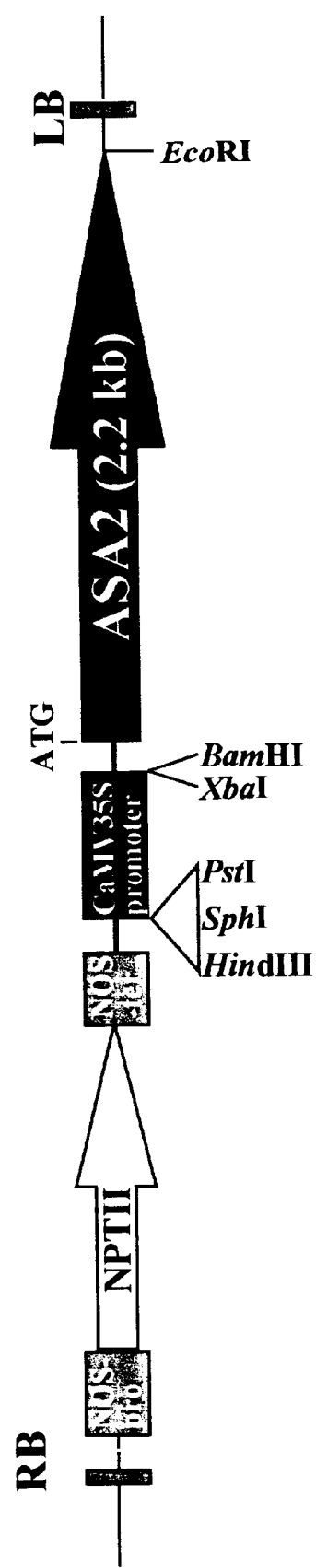
FIG. 17 presents the T-DNA region of pBIN-ASA2. Arrows indicate the direction of transcription. RB denotes right border, LB: left border, NOS-pro: nopaline synthase promoter, NOS-ter: nopaline synthase terminator, NPTII: neomycin transferase gene., 35S: 35S promoter of CaMV, and ASA2: the 2.2 kb coding and 3' downstream regions of the anthranilate synthase gene.
Figure 18:
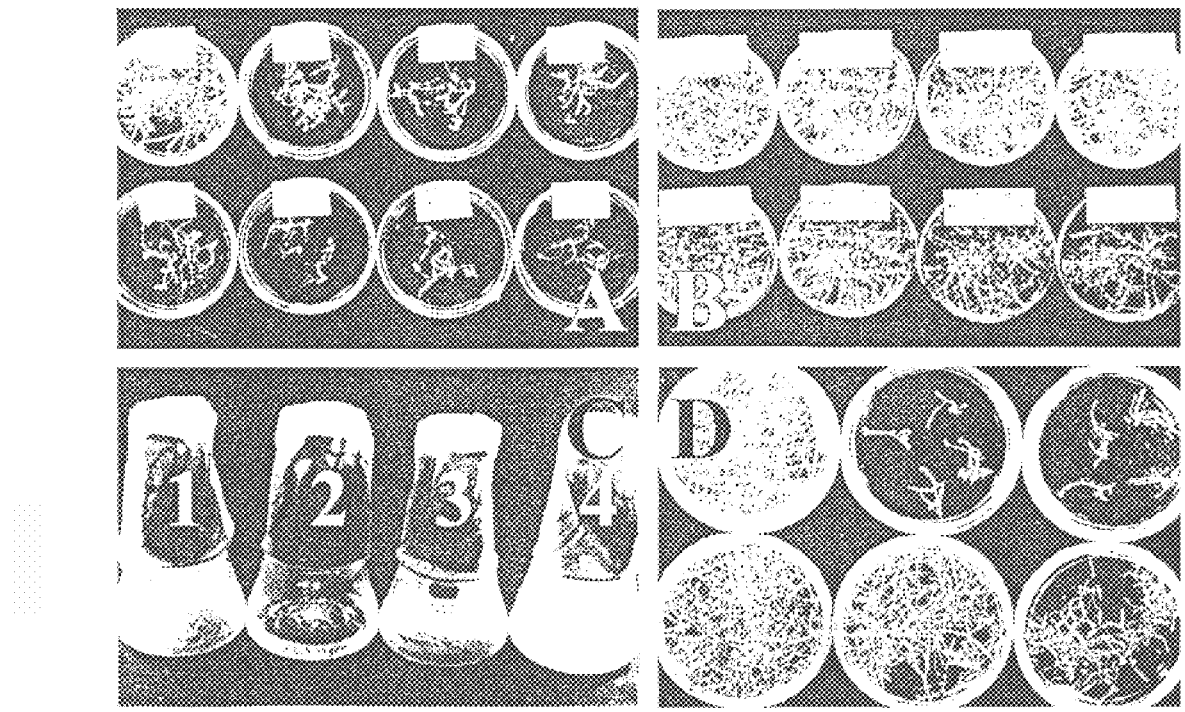
FIGS. 18A to 18D show the-effects of 5MT on the growth of Astragalus sinicus (hereinafter referred to as "A. sinicus") hairy root lines. (A) Control A. sinicus hairy root line C-75 after 6 weeks cultivation. Upper left: 0, 10, 15 and 20 $\mu$M 5MT. Bottom left: 25, 30, 40 and 50 $\mu$M 5MT. (B) Transformed A. sinicus hairy root line A-10 after 6 weeks cultivation on the same 5MT concentrations as FIG. 18A. (C) A. sinicus hairy root growth in liquid medium after 6 weeks cultivation. Flask 1: Control hairy root line C-75 in the absence of 5MT. Flask 2: Control hairy root line C-75 in 50 $\mu$M 5MT. Flask 3: Transformed hairy root line A-9 in the absence of 5MT. Flask 4: Transformed hairy root line A-9 in 50 $\mu$M 5MT. (D) Growth of soybean hairy root lines after 8 weeks cultivation. Upper: Control hairy root lines in 0, 15 and 40 $\mu$M 5MT. Bottom: Transformed hairy root lines in 0, 15 and 40 $\mu$M 5MT. Plates are 9 cm in diameter and the flasks are about 6 cm in diameter at the base.
Figure 19A:
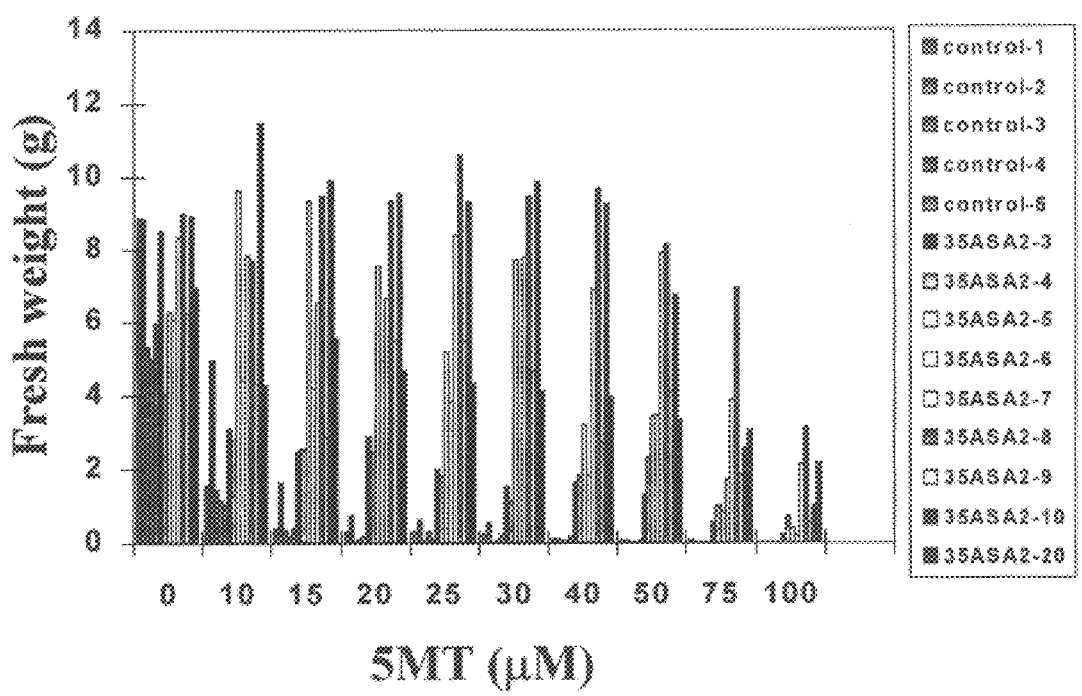
FIGS. 19A to 19B present the quantitative data on the effect of 5MT on the growth of hairy root lines. The quantitative root growth test demonstrated the increased 5MT resistance conferred to the transformed A. sinicus hairy root lines by the introduced 35S-ASA2 gene construct. Hairy roots, initially about 200 mg, were grown for 6 weeks on MS medium containing serial concentrations of 5MT. At least 3 independent experiments were analyzed.
Figure 19B:
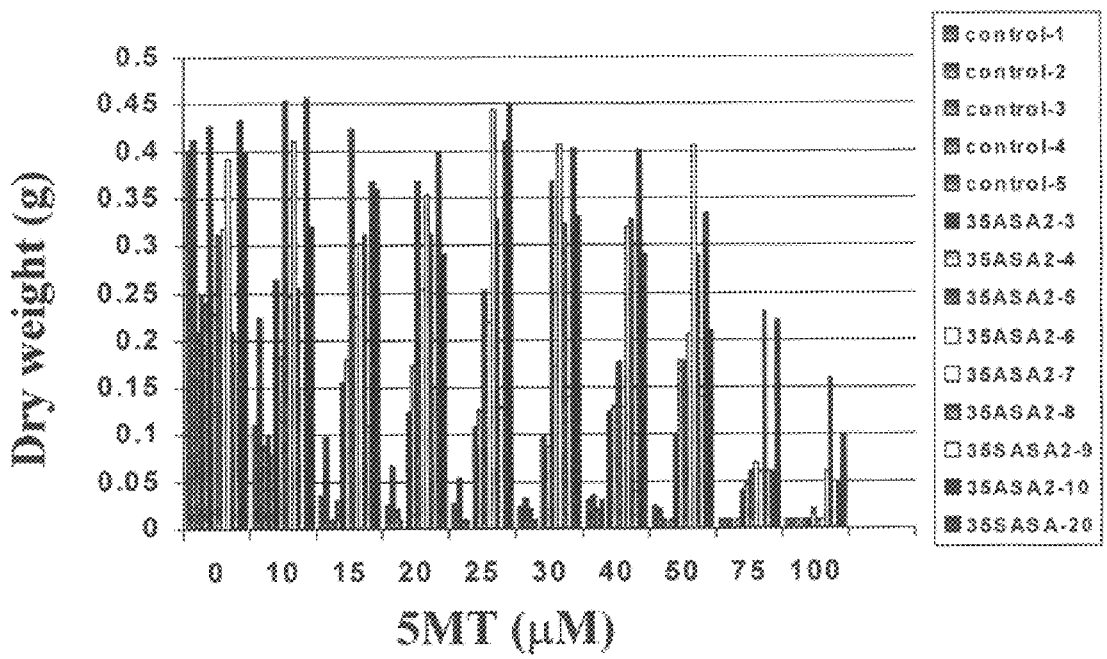

As shown in FIG. 17, the pBIN-ASA2 plasmid contains the 2.2 kb coding and 3' downstream regions of the ASA2 cDNA isolated from 5MT$^r$ tobacco cell line AB15-12-1 (Song et al., 1998). Expression of the ASA2 cDNA is under the control of the CaMV 35S promoter. This plasmid also contains a kanamycin resistance gene, nptII, as a selectable marker. After selection of apparent kanamycin resistant *A. sinicus* roots, these root lines were decontaminated by 2–3 subcultures on carbenicillin-containing medium and then were maintained in carbenicillin-free medium.

Large numbers of kanamycin resistant root lines were produced from Astragalus seedlings transformed with pBIN-ASA2 and some were tested by the PCR reaction using primers to the ASA2 cDNA. The primers used for amplification of a fragment (approximately 1107 bp) of the ASA2 cDNA gene were 5' CTG CAG CAA TTC ATG CAG TCG TTA CCT ATC 3' (SEQ ID NO: 34) and 5' CTT CCC TCT TCT GCT TGT CCC 3' (SEQ ID NO: 35). The controls were a hairy root line transformed with. *A. rhizogenes* strain DC-AR2, and the amplified 1107 bp fragment from the binary vector pBIN-ASA2. Thirty-four independent transgenic hairy root lines transformed with *A. rhizogenes* strain DC-AR2 harboring pBIN-ASA2 were analyzed. An 1107 bp band corresponding to the relevant sequence of ASA2 cDNA was reproducibly detected in all 34 kanamycin resistant transgenic hairy root lines and not in the control sample.

Southern blot analysis corroborated the PCR screening and further demonstrated the stable incorporation of the 35S-ASA2 gene construct into the *A. sinicus* hairy root genome. The Southern blot hybridization analyzed DNA samples isolated from control and transformed *A. sinicus* hairy roots, probed with $^{32}$P-labeled 2.2 kb ASA2 cDNA. Two Southern blot hybridizations were conducted with all the DNAs digested either with (1) BamHI; or (2) EcoRI, in the respective Southern blots. DNA from a control hairy root line transformed with *A. rhizogenes* strain DC-AR2 and DNA from independent hairy root lines (A-3, 5, 6, 7, 8, 9, 10 and 20) transformed with *A. rhizogenes* strain DC-AR2 harboring pBIN-ASA2 were tested.

Plant genomic DNAs digested with BamHI or EcoRI were separated by gel electrophoresis and hybridized with the labeled 2.2 kb ASA2 cDNA probe. The hybridization signal band corresponding to the 35S-ASA2 gene construct was detected in all DNAs isolated from the hairy root lines transformed by A. rhizogenes strain DC-AR2 containing the pBIN-ASA2 binary vector but not from those transformed by DC-AR2 without the binary vector. Since BamHI and EcoRI are unique sites in the T region of the binary vector, the presence of one to five fragments of variable size in the genomic DNA indicates the insertion of about one to five copies of the T-DNA with ASA2 into the plant genome.

To demonstrate the expression of the ASA2 cDNA, total RNA isolated from transformed and control hairy root lines was hybridized with labeled ASA2 cDNA as the probe, and a single signal was detected in RNA from all hairy root lines transformed by 35S-ASA2 gene construct. Approximately 30 mg of total RNA was used for the Northern blot hybridization and a full-length (2.2 kb) ASA2 cDNA clone was used as probe for hybridization. Total RNA was prepared from a 1-week-old 5MT$^s$ N. sylvestris suspension cultured cell line, a 1-week-old 5MT$^r$ N. sylvestris suspension cultured cell line, a control hairy root line transformed with A. rhizogenes strain DC-AR2, and 10 independent hairy root lines (A-3, 4, 5, 6, 7, 8, 9, 10, 20 and 45) transformed with A. rhizogenes strain DC-AR2 harboring pBIN-ASA2. The amount of rRNA in each sample was equal as shown by staining with ethidium bromide. The size of the hybridized RNA species in all the transformed hairy root lines was approximately 2.2 kb, identical to the size of the ASA2 transcript from the 5MT$^r$ N. sylvestris suspension cultured cell line. No hybridization signal was detectable in RNA from the control hairy root line or the 5MT$^s$ N. sylvestris suspension cultured cell line. Hairy root lines A-8, 9 and 20 showed very strong hybridization signals which were comparable to or higher than that found with the 5MT$^r$ N. sylvestris suspension cell line. This indicates that the ASA2 expression is very high in these three lines but the ASA2 transcript level was lower in some individual hairy root lines.

In another Northern hybridization, approximately 30 mg of total RNA isolated from leaves, stems, and roots from regenerated plants was used for the Northern blot hybridization and a full-length (2.2 kb) ASA2 cDNA clone was used as probe for hybridization. Total RNA was prepared from a 1-week-old 5MT$^s$ N. sylvestris suspension cultured cell line, a 1-week-old 5MT$^r$ N. sylvestris suspension cultured cell line, a control hairy root line transformed with A. rhizogenes strain DC-AR2, and leaves, stems, and roots from plants regenerated from the transformed hairy root line A-20. The amount of rRNA in each sample was equal as shown by staining with ethidium bromide. The Northern hybridization showed that leaf, stem and root tissues from plants regenerated from the transformed hairy root line A-20 showed strong expression of the ASA2 transcript. A single 2.2 kb ASA2 transcript was detected in total RNA isolated from all the tissues but not from control plantlets not transformed with ASA2. Thus, we can conclude that ASA2 cDNA was effectively and constitutively expressed in tissues of a legume plant, A. sinicus, when under the control of the 35S promoter.

(ii) 5MT Resistance

Since expression of the feedback-insensitive ASA2 gene should increase resistance to the Trp analog 5MT as shown previously with E. coli (Song et al., 1998), a quantitative root growth test was used to assess the extent of 5MT resistance of the transformed hairy root lines. Transformed roots were grown for 6 weeks with 0, 10, 15, 20, 25, 30, 40, 50, 75 and 100 $\mu$M 5MT in both MS liquid and solid medium, respectively (FIGS. 18A to 18C and FIGS. 19A and 19B).

Control hairy root growth was inhibited by 10–20 $\mu$M 5MT and almost complete inhibition occurred at 30 $\mu$M or higher 5MT concentrations. Hairy root lines A-7, 8, 9, 10 and 20 are, however, able to grow with 5MT concentrations of up to 100 $\mu$M, the maximum concentration tested. All of the hairy root lines transformed with the ASA2 gene also showed increased resistance to 5MT compared to control hairy root lines when grown in liquid medium. Hairy root lines A-7, 8, 9, 10 and 20 grew at concentrations of up to 100 $\mu$M 5MT in liquid medium. On the other hand, control hairy root lines turned brown and eventually died at 20 $\mu$M or higher 5MT concentrations. These results indicate that the hairy root lines are more sensitive to 5MT inhibition in liquid medium than in solid medium and that the transformed lines are clearly more resistant than untransformed lines. Based on these observations, we conclude that the 35S-ASA2 gene construct can confer resistance to 5MT to A. sinicus hairy root lines.

(iii) Free-Trp

Table 4, below, presents the free Trp values in ASA2 transformed A. sinicus hairy root lines. Duplicate extracts of each line were analyzed as described in section A1(vi), above, of this Example 8.

When the free Trp levels were measured in A. sinicus hairy root lines (Table 4), the five control lines tested contained an average free Trp level of 60 nmol g$^{-1}$ fresh weight. One control line, 2.3 GUS(4), consistently contained free Trp levels higher than this average (93 nmol g$^{-1}$ fresh weight). Of the 22 independent ASA2 transformed lines tested, 20 contained more free Trp than the control average and these ranged from 73 to 316 nmol g$^{-1}$ fresh weight, a 22 to 427% increase. When tobacco suspension cultured cells are selected using 5MT and ASA2 is overexpressed in the resistant line (Song et al., 1998, supra), a similar 5-fold increase in free Trp is observed.

TABLE 4

ASA2 Transformed Hairy Root Analysis: Trp Concentration

| Line | Trp Concentration (nmol/g[fw]) | Fold Increase (Ave Cntrl: 60) |
| --- | --- | --- |
| 1.3GUS(75) | 34 | |
| 35SASA2(76) | 42 | 0.7 |
| 2.3GUS(76) | 42 | |
| 35SASA2(44) | 43 | 0.7 |
| GFP4(77) | 56 | |
| 1.3GUS(90) | 61 | |
| 35SASA2(11) | 73 | 1.2 |
| 35SASA2(19) | 79 | 1.3 |
| 35SASA2(10) | 81 | 1.3 |
| 35SASA2(1) | 92 | 1.5 |
| 35SASA2(18) | 92 | 1.5 |
| 2.3GUS(4) | 103 | |
| 35SASA2(5) | 127 | 2.1 |
| 35SASA2(22) | 127 | 2.1 |
| 35SASA2(6) | 128 | 2.1 |
| 35SASA2(12) | 144 | 2.4 |
| 35SASA2(25) | 149 | 2.5 |
| 35SASA2(4) | 180 | 3.0 |
| 35SASA2(16) | 198 | 3.3 |
| 35SASA2(9) | 202 | 3.4 |
| 35SASA2(42) | 215 | 3.6 |
| 35SASA2(3) | 247 | 4.1 |
| 35SASA2(7) | 256 | 4.3 |
| 35SASA2(8) | 264 | 4.4 |
| 35SASA2(20) | 297 | 4.9 |
| 35SASA2(27) | 313 | 5.2 |
| 35SASA2(45) | 316 | 5.3 |

(iv) AS Activity

Figure 20A:
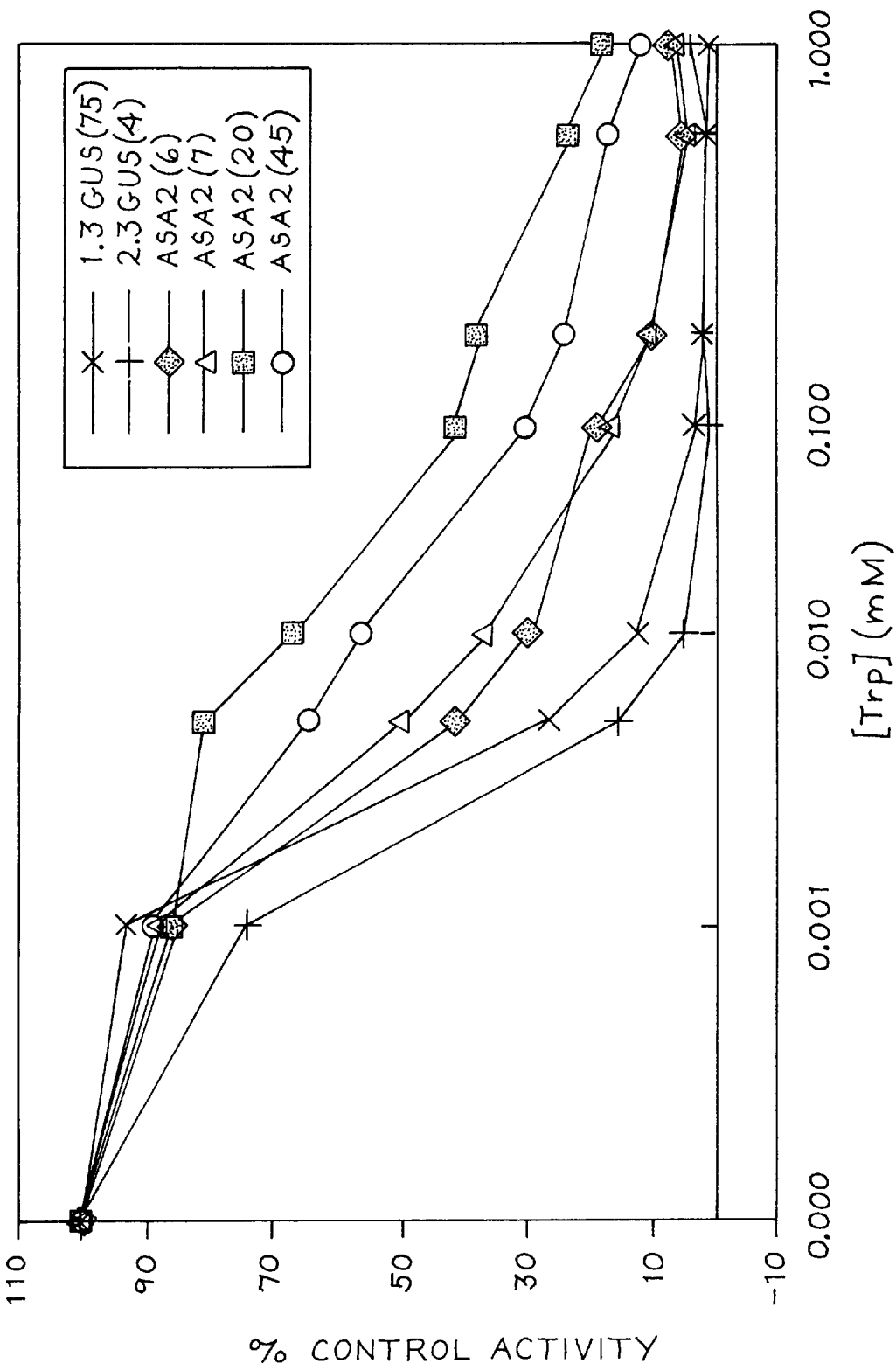
FIGS. 20A to 20C graphically presents the inhibition by Trp of AS activity in extracts of A. sinicus hairy root lines. Control lines: 1.3GUS-75 (x), 2.3GUS-4 (+) and ASA2 transformed lines: A-6 (♦), 7 (Δ), 20 (■), and 45(○). (A) AS activity in the presence of Trp was measured as described in Example 8, below, with 100 mM-NH$_4$Cl and 100$\mu$M chorismate as substrates. Relative AS activity is the percentage of the activity observed when no Trp was added. The specific activity with no Trp added for each line was 35, 36, 26, 29, 58 and 53 pmol min$^{-1}$ mg$^{-1}$ protein, respectively. (B) AS activity measured using either 100 mM NH$_4$Cl or 10 mM Gln as the second substrate for AS. (C) AS Trp insensitivity versus free Trp found in the roots. The apparent K$_i$ values for the six A. sinicus lines were estimated by determining the Trp concentration that resulted in 50% AS inhibition as in FIG. 20A with NH$_4$Cl as the second substrate. The Trp values are from Table 4.

The feedback inhibitory effects of Trp on the AS activity in extracts of control and ASA2 transformed *A. sinicus* hairy root lines were first measured using $NH_4Cl$ and not glutamine as the second substrate for the enzyme. Because free ASA2 subunits are capable of producing anthranilate from chorismate using ammonium, this assay measured ASA2 subunits present both as part of a holoenzyme complex with native β-subunits or as free subunits. In all four ASA2 transformed lines tested, AS was less sensitive to Trp inhibition than was AS from the two control line extracts (FIG. 20A).

The apparent $K_i$ values for Trp, estimated from the Trp concentration causing 50% inhibition, were 4, 5, 16 and 30 μM for the ASA2 transformed lines, and 2 and 3 μM for the controls. This compares to AS activity in extracts of wild-type and 5MT-resistant tobacco suspension cultured cells where the apparent $K_i$ values were 2 and 300 μM, respectively, and for ASA2 expressed in *E. coli*, 100 μM (Song et al., 1998, supra). Though the changes in $K_i$ are modest compared to that observed in these other cell extracts containing ASA2, there is still a significant difference in the amount of AS activity at higher Trp concentrations especially in transformed lines where ASA2 transformation also increased the total AS activity (*A. sinicus* hairy root lines 20 and 45). This apparently results in the higher free Trp observed in these lines. In the two ASA2 transformed lines where total activity was lower than the control lines, AS activity was still less sensitive to Trp inhibition and free Trp was higher than in the controls.

Figure 20B:
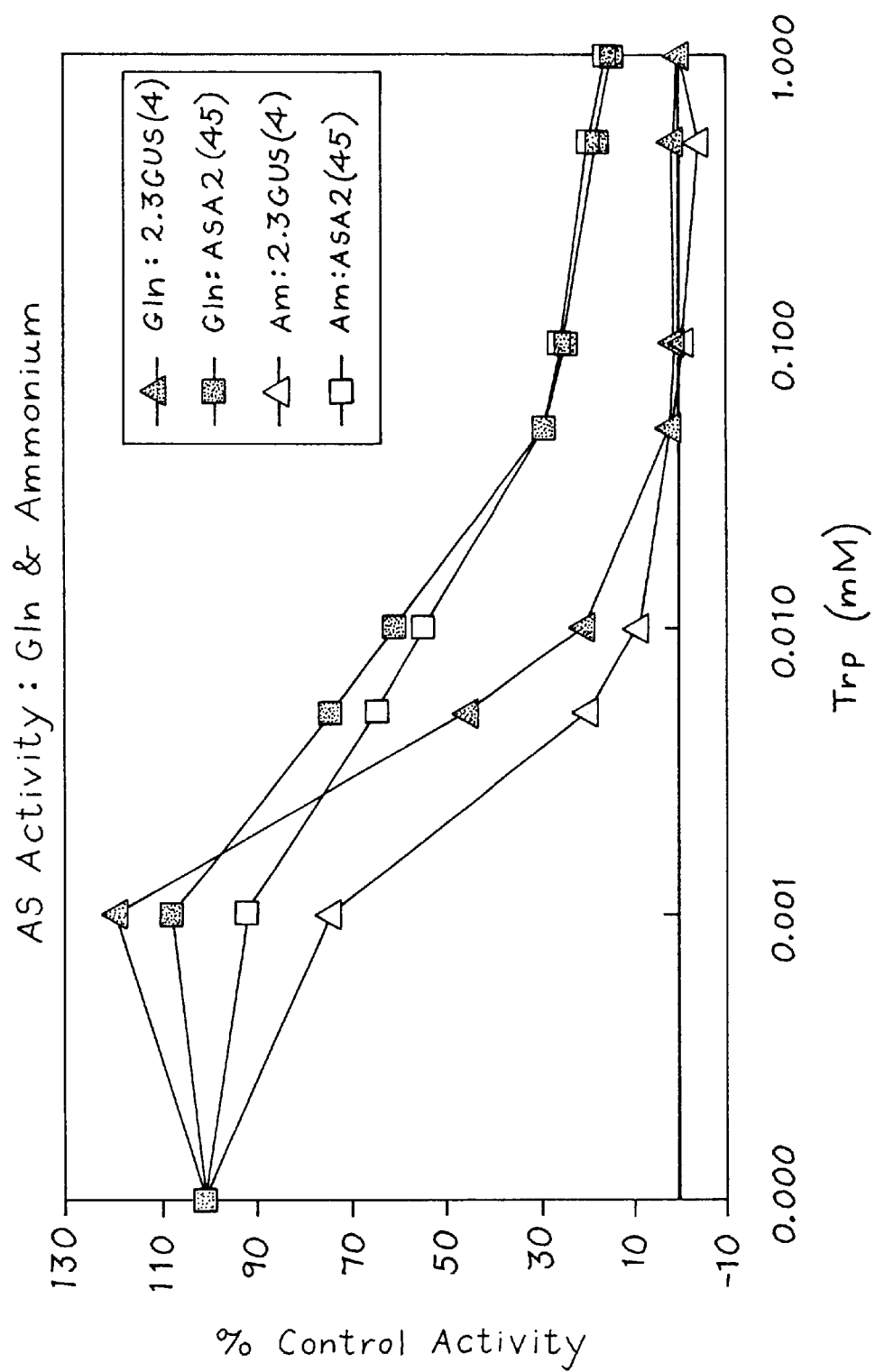

The AS activity was also measured in extracts of a control and an ASA2 transformed *A. sinicus* hairy root line using either 100 mM $NH_4Cl$ or 10 mM Gln as the second substrate for AS (FIG. 20B). AS activity in the ASA2 transformed line extract was as Trp insensitive when Gln was used as the second substrate as when $NH_4Cl$ was used.

This suggests that the ASA2 transgene product has complexed 5 with a native α-subunit or subunits to form a holoenzyme capable of catalyzing a Gln dependent reaction. The ratio of $NH_4Cl$ dependent activity to Gln dependent activity was higher in the extract of the ASA2 transformed line than in the control. A similar change in this ratio is observed in 5MT-selected tobacco 10 suspension cultured cells where ASA2 is overexpressed (data not shown). This may suggest that some free ASA2 subunits are present in the transformed line extract and are detected only when $NH_4Cl$ is used in the assay. Alternately, this may represent an inherent kinetic difference between the ASA2 gene product and other α-subunits.

Figure 20C:
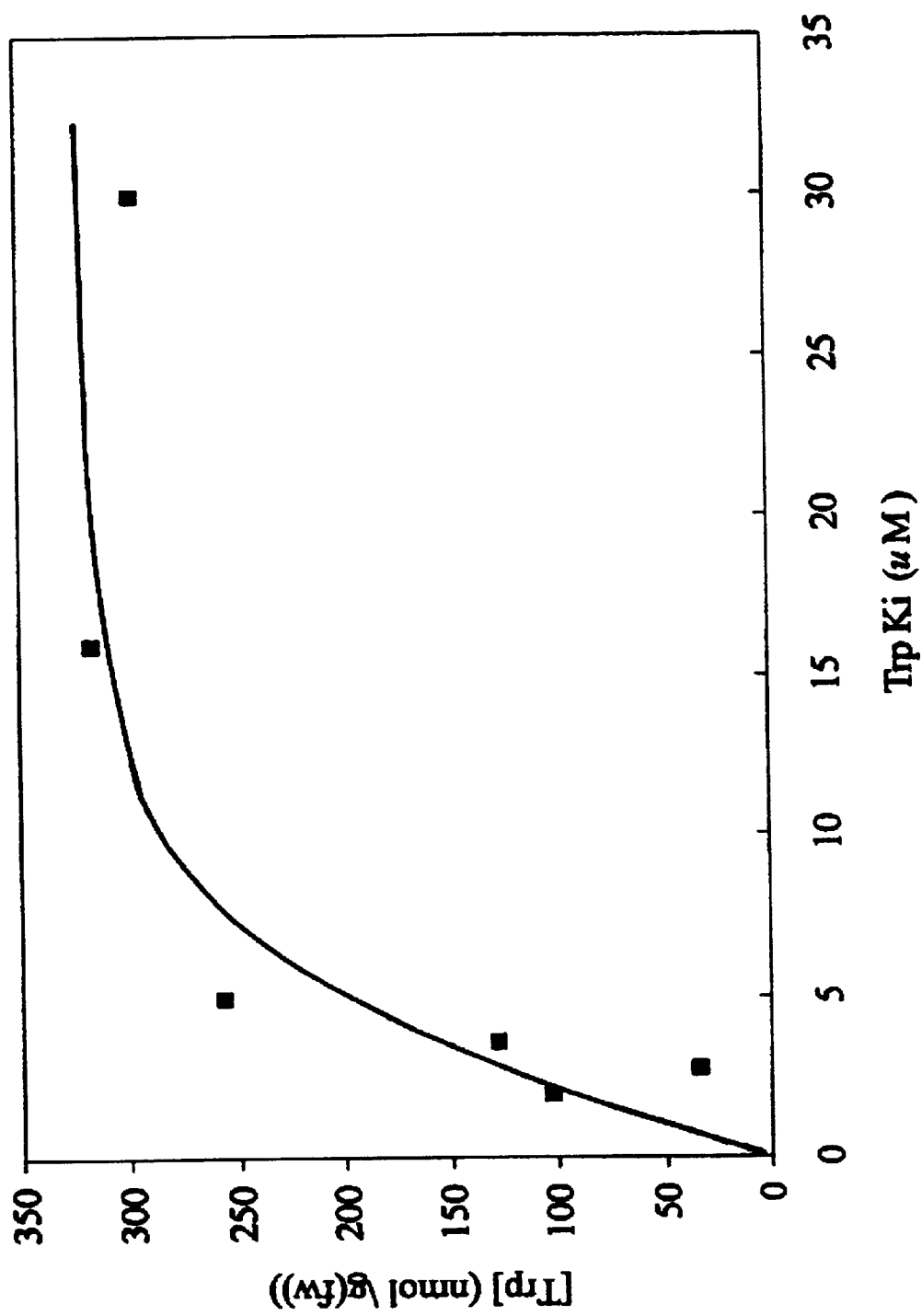

There is a correlation between free Trp and AS feedback insensitivity ($K_i$) (FIG. 20C).

(v) Direct Selection With 5MT

Figure 21:
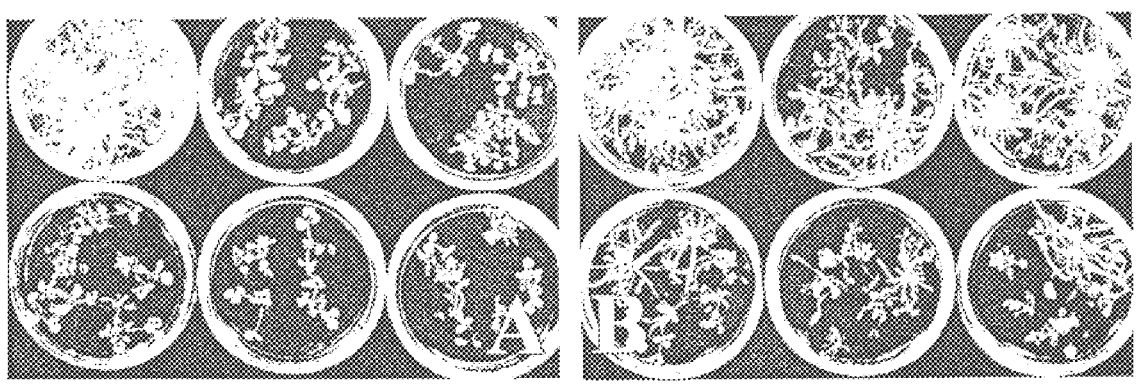
FIGS. 21A and 21B show the direct selection of 5MT resistant hairy root lines from *A. sinicus* seedlings. (A) Control *A. sinicus* seedlings transformed with an *Agrobacterium rhizogenes* (hereinafter referred to as "*A. rhizogenes*") DC-AR2 after 4 weeks cultivation with top row: 0, 15 and 20 µM 5MT and bottom row: 25, 30, and 40 µM 5MT. (B) *A. sinicus* seedlings transformed with *A. rhizogenes* DC-AR2 containing the pBIN-ASA2 vector after 4 weeks cultivation with top row: 0, 15 and 20µM 5MT and bottom row; 25, 30 and 40 µM 5MT. Plates are 9 cm in diameter.

Since the *A. sinicus* hairy root lines initially selected for kanamycin-resistance but which were also transformed with the feedback-insensitive ASA2 cDNA show resistance to growth inhibition by 5MT (FIG. 18), we wanted to determine if direct selection could be done for *A. sinicus* hairy root line formation on medium containing 5MT (FIGS. 21A and 21B). Transformation of *A. sinicus* seedlings with DC-AR2 harboring pBIN-ASA2 gave rise to hairy root line formation on medium containing 0, 15, 20, 25, 30 and 40 μM 5MT but inhibition occurred at 50, 75 and 100 μM.

Rooting frequencies were similar to those found for kanamycin selection. Control plates transformed with DC-AR2 gave rise to only a few short hairy root lines on medium containing 5MT at 15 and 20 μM and none were formed at 25, 30, 40, 50, 75 and 100 μM. All the individual roots obtained in these experiments were excised and placed on medium containing the same 5MT concentration. After 2–3 subcultures, some of these roots stopped growing while others grew vigorously. On the other hand, all control roots derived from *A. sinicus* seedlings transformed with DC-AR2 turned brown and died in 5MT concentrations of 15 μM or higher. These results were comparable to those obtained in *A. sinicus* transformation experiments using kanamycin as a selective agent and show that ASA2 can be used as a selectable marker.

When the 5MT resistant roots were placed on 75 μg/ml kanamycin supplemented medium, the growth of some roots was inhibited while most grew vigorously. All control roots derived from *A. sinicus* seedlings transformed with DC-AR2 and grown on medium lacking 5MT did not grow on medium containing kanamycin.

PCR analysis and gel electrophoresis were used to directly detect ASA and nptII transgenes in *A. sinicus* hairy root lines selected with different concentrations of 5MT. An amplified 1107 bp fragment from the binary vector pBIN-ASA2 was compared to a control hairy root line transformed with *A. rhizogenes* strain DC-AR2, four independent transgenic hairy root lines selected with 15 μM 5MT, six independent transgenic hairy root lines selected with 20 μM 5MT, five independent transgenic hairy root lines selected with 25 μM 5MT, five independent transgenic hairy root lines selected with 30 μM 5MT, four independent transgenic hairy root lines selected with 40 μM, and a 1 kb DNA ladder. Two PCR analyses were used: (A) in the first analysis, the primers used for amplification of an approximately 1107 bp fragment of the ASA2 cDNA gene were 5' CTG CAG CAA TTC ATG CAG TCG TTA CCT ATC 3' (SEQ ID NO: 34) and 5' CTT CCC TCT TCT GCT TGT CCC 3' (SEQ,ID NO: 35); (B) in the second analysis, the primers used for amplification of an approximately 409 bp fragment of the nptII gene were 5' ATC TCA CCT TGC TCC TGC 3(SEQ ID NO: 36) and 5' ATA CCG TAA AGC ACG AGG 3' (SEQ ID NO: 37).

The 5MT resistant hairy root lines tested by the first PCR analysis using primers to the ASA2 cDNA and nptII genes produced a band of 1107 bp corresponding to the relevant sequence of ASA2 cDNA while the control roots did not. In the second PCR analysis, a band of 409 bp corresponding to the relevant sequence of nptII was also reproducibly detected in all the 5MT resistant hairy root lines but not in the control sample. These results indicate that all of the 24 individual 5MT resistant hairy root lines analyzed contain both the ASA2 and nptII genes.

To demonstrate the expression of the ASA2 cDNA in transformed hairy root lines after three rounds of direct selection on medium containing 5MT, total RNA isolated from transformed and control hairy root lines was hybridized with labeled ASA2 cDNA as the probe and a single band was detected in RNA from all hairy root lines transformed by the 35S-ASA2 gene construct. The details of the analysis is as follows: Approximately 30 μg of total RNA was used for the Northern blot hybridization and a full-length (2.2 kb) ASA2 cDNA clone was used as probe for hybridization. Total RNA was prepared from a control hairy root line transformed with *A. rhizogenes* strain DC-AR2; a 1-week-old 5MT$^r$ *N. sylvestris* suspension cultured cell line; 2 independent hairy root lines (A20–72 and 73) after 3 times direct selection with 20 μM 5MT; 3 independent hairy root lines (A25–70, 72 and 76) after 3 times direct selection with 25 MM 5MT; 2 independent hairy root lines (30–70 and 80) after 3 times direct selection with 30 μM 5MT; and 2 independent hairy root lines (A40–80 and 90) after 3 times direct selection with 40 μM 5MT transformed with *A. rhizogenes* strain DC-AR2 harboring pBIN-ASA2. The amount of rRNA in each sample was equal as shown by staining with ethidium bromide.

The size of the hybridized RNA species in the transformed hairy root lines was approximately 2.2 kb, identical to the size of the ASA2 transcript from the 5MT$^r$ *N. sylvestris* suspension cultured cell line. No hybridization signal was detectable in RNA from the control hairy root line. Hairy root lines A20–72, 73, A30–70, A40–80 and 90 showed very strong hybridization signals which were comparable to or higher than that found with the 5MT$^r$ *N. sylvestris* suspension cell line.

The results presented here indicate that the tobacco feedback-insensitive ASA2 cDNA can be used as an efficient selectable marker with the *A. rhizogenes*-mediated *A. sinicus* transformation system and suggest that ASA2 could be a very useful and versatile marker gene of plant origin for transformation of other plant species.

B. Transformation and Expression of the Tobacco Feedback-Insensitive Anthranilate Synthase Gene (ASA2) in Soybean 1. Materials and Methods The soybean (cv. Williams 82) cotyledons from 4 to 6-day-old-seedlings were harvested and wounded with a scalpel previously-dipped into an overnight culture of the *A. rhizogenes* strain K599. Cotyledons were inoculated by cutting the adaxial face several times to form a checked wound site and the abaxial side was placed on sterile distilled water partially immersed filter paper and incubated as described above. Three days after inoculation, cotyledons were transferred to medium containing Murashige and Skoog basal minerals and B5 organics (Gamborg, O. L., et al. Expt. *Cell. Res.* 50: 148–151, 1968) solidified with 3 g/l Gellan gum (Kelko, Division of Merck) (MXB medium) in 100×25 mm petri dishes. To inhibit the growth of bacteria and to select transformed roots, 500 mg/l of carbenicillin disodium and 200 mg/l kanamycin were added to the MXB medium. After hairy roots developed from wounded cotyledons,. single root tips (2–3 cm) were excised and used to establish bacteria-free root clones by subculture to fresh MXB solid medium grown at 28° C. in the dark. After 3 to 4 subcultures, the roots were maintained on MXB medium lacking antibiotics and the established root cultures were transferred every 4–6 weeks according to their growth rate for maintenance. Forty to sixty cotyledons were inoculated for each bacterial strain and binary vector.

2. Results

Figure 22A:
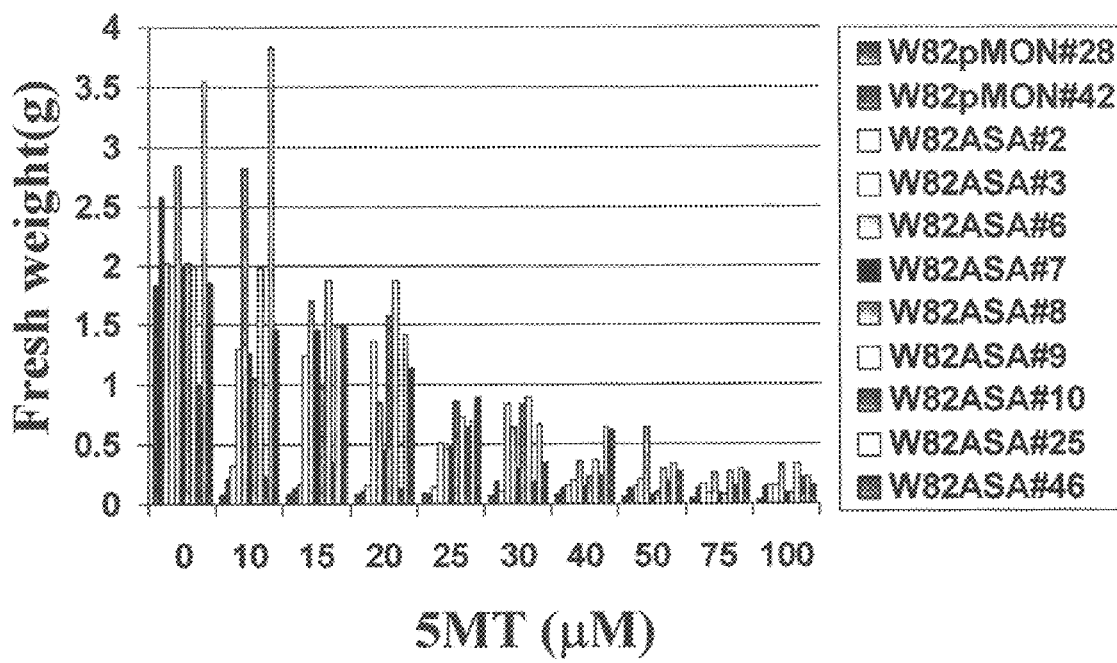

Large numbers of kanamycin resistant root lines were produced from soybean cotyledons transformed with pBIN-ASA2 and a quantitative root growth test was also performed to assess the extent of 5MT resistance of the transformed hairy root lines. Transformed roots were grown for 8 weeks with 0, 10, 15, 20, 25, 30, 40, 50, 75 and 100 μM 5MT in solid medium (FIGS. 18D, 22A and 22B). The results were similar to those obtained with *A. sinicus* but the soybean hairy root lines are more sensitive to 5MT inhibition than those of *A. sinicus*. Based on these observations, we conclude that the 35S-ASA2 gene construct can also confer resistance to 5MT with soybean hairy root lines.

Deposit of Strains

The following cell line and clones were deposited under at the American Type Culture Collection, 12301 Parklawn Drive, Rockville, Md. 20852 according to the terms of the Budapest Treaty and will be maintained for a period of thiry (30 years) from the date of deposit, or for five (5) years after the last request for the deposit, whichever is longer.

The *N. tabacum* AB-15-12-1 cell line maintained in MX medium containing 300 μM 5MT were deposited on Jul. 22, 1997, and accorded A.T.C.C. deposit number 209176.

The *N. tabacum* ASA2 promoter (as plasmid DNA pUCASA2-GUS and accorded A.T.C.C. deposit number 209150), *N. tabacum* ASA3 partial genomic clone (as plasmid DNA pGemTASA3 and accorded A.T.C.C. deposit number 209151), and *N. tabacum* ASA2 cDNA clone (as plasmid DNA pGemTASA2 and accorded A.T.C.C. deposit number 209152) were deposited on Jul. 22, 1997.

Availability of the deposited recombinant transfer vector is not to be construed as a license to practice the invention in contravention of the rights granted under the authority of any government in accordance with its patent laws.

The deposits and any other deposited material described herein are provided for convenience only, and are not required to practice the present invention in view of the teachings provided herein.

Also, the present invention is not to be considered limited in scope by the deposited recombinant transfer vector, since the deposited vector is intended only to be illustrative of particular aspects of the invention. Any recombinant transfer vector which can be used to prepare recombinant microorganism which can function to produce a recombinant protein product described herein is considered to be within the scope of this invention.

All publications and patent applications mentioned in this Specification are herein incorporated by reference to the same extent as if each of them had been individually indicated to be incorporated by reference.

Although the foregoing invention has been described in some detail by way of illustration and example for purposes of clarity and understanding, various modifications and changes in addition to those shown and described herein which are apparent to those skilled in the art from the preceding description are considered to fall within the scope of the appended claims. Future technological advancements which allows for obvious changes in the basic invention herein are also within the claims.

We claim:

1. An isolated nucleic acid molecule comprising a nucleotide sequence selected from the group consisting of SEQ ID NO: 4, a nucleotide sequence which encodes SEQ ID NO: 5, and a nucleotide sequence that is completely thereof.

2. An isolated nucleotide sequence selected from the group consisting of SEQ ID NO: 4, a nucleotide sequence encoding SEQ ID NO: 5, and a nucleotide sequence which is completely complementary thereof.

3. An isolated DNA construct comprising an expression cassette, wherein sad expression cassette comprises a promoter operatively linked with a DNA sequence selected from the group consisting of: SEQ ID NO: 4 and a DNA sequence which encodes SEQ ID NO: 5.

4. The DNA construct of claim 3, further comprising a desirable gene.

5. A cell transformed with the DNA construct of claim 3.

6. A plant comprising transformed plant cells containing the DNA construct of claim 3.

7. A cell obtained from a *Nicotiana tabacum* plant cell line designated AB-15-12-1.

8. A recombinant cell containing a nucleotide sequence selected from the group consisting of: SEQ ID NO: 4 and a nucleotide sequence which encodes SEQ ID NO: 5.

9. A method of selecting a transformed plant cell, comprising the steps of:
  (a) introducing into a plant cell an expression cassette comprising a nucleotide sequence to yield a transformed plant cell, said nucleotide sequence is selected from the group consisting of: SEQ ID NO: 4 and a nucleotide sequence which encodes SEQ ID NO: 5 wherein the transformed plant expresses said nucleotide sequence; and
  (b) culturing the transformed plant cell in a medium containing free tryptophan or an amino acid analog of tryptophan that inhibits the growth of a plant cell which does not contain the nucleotide sequence, and selecting said transformed plant cell that grows in the presence of said free tryptophan or said amino acid analog of tryptophan.

10. The method of claim 9, wherein the expression cassette further comprises a desirable gene.

11. A method of generating a plant cell which is resistant to free tryptophan or to an amino acid analog of tryptophan comprising the steps of:
  (a) introducing an expression cassette comprising a nucleotide sequence encoding an exogenous tobacco anthranilate synthase operably linked to a promoter functional in a plant cell into a cell of a plant to yield a transformed plant cell, wherein the tobacco anthranilate synthase is resistant to inhibition by free tryptophan or by an amino acid analog of tryptophan and wherein said nucleotide sequence is selected from the group consisting of: SEQ ID NO: 4 and a nucleotide sequence which encodes SEQ ID NO: 5; and
  (b) expressing the tobacco anthranilate synthase encoded by the nucleotide sequence in the plant cell so as to yield said tobacco anthranilate synthase to render the transformed plant cell resistant to inhibition by an amount of free tryptophan or an amino acid analog of tryptophan that inhibits the growth of an untransformed plant cell.

12. A transformed plant regenerated from the transformed plant cell obtained by the method of any one of claims 9, 10, and 11.

13. A method for increasing the tryptophan content in a plant, comprising:
  (a) introducing into cells of a plant an expression cassette comprising a recombinant DNA segment encoding an anthranilate synthase operably linked to a promoter functional in a plant cell to yield a transformed plant cells, wherein the DNA segment encodes the anthranilate synthase which is resistant to inhibition by free tryptophan or by an amino acid analog of tryptophan and wherein said recombinant DNA segment is selected from the group consisting of: SEQ ID NO: 4 and a DNA sequence which encodes SEQ ID NO: 5; and
  (b) regenerating a differentiated plant from said transformed plant cells wherein the cells of the differentiated plant express the anthranilate synthase encoded by the DNA segment to increase the tryptophan content in the cells of the differentiated plant relative to the tryptophan content in the cells of an untransformed plant.

14. A method of producing tobacco anthranilate synthase comprising:
   (a) introducing an expression cassette comprising a DNA segment encoding a tobacco anthranilate synthase into a host cell;
   (b) expressing the DNA segment encoding the tobacco anthranilate synthase in said host cell so as to yield tobacco anthranilate synthase; and
   (c) recovering the tobacco anthranilate from said host cell; wherein said DNA segment is selected from the group consisting of SEQ ID NO: 4 and a DNA sequence which encodes SEQ ID NO: 5.

15. A transformed seed of a transformed plant, wherein the transformed plant contains an exogenous nucleotide sequence selected from the group consisting of: SEQ ID NO: 4 and a nucleotide sequence which encodes SEQ ID NO: 5 wherein the transformed seed contains said exogenous nucleotide sequence.

16. A transformed seed of a transformed plant regenerated from a transform plant cell which contains an exogenous nucleotide sequence selected from the group consisting of: SEQ ID NO: 4 and a nucleotide sequence which encodes SEQ ID NO: 5 wherein the transformed seed contains said exogenous nucleotide sequence.

17. A cell transformed with the DNA construct of claim 4.

18. A plant comprising transformed plant cells containing the DNA construct of claim 4.

* * * * *

SEQUENCE LISTING

<160> NUMBER OF SEQ ID NOS: 37

<210> SEQ ID NO 1
<211> LENGTH: 21
<212> TYPE: DNA (cDNA)
<213> ORGANISM: Nicotiana tabacum -continued

```
<400> SEQUENCE: 1
gcggctttgt tctggcactc a                                              21

<210> SEQ ID NO 2
<211> LENGTH: 21
<212> TYPE: DNA (cDNA)
<213> ORGANISM: Nicotiana tabacum

<400> SEQUENCE: 2
ctgcaaatgt tcgccgctca a                                              21

<210> SEQ ID NO 3
<211> LENGTH: 21
<212> TYPE: DNA (cDNA)
<213> ORGANISM: Nicotiana tabacum

<400> SEQUENCE: 3
ctagttatgg atgaggacag g                                              21

<210> SEQ ID NO 4
<211> LENGTH: 2161
<212> TYPE: DNA (cDNA)
<213> ORGANISM: Nicotiana tabacum

<400> SEQUENCE: 4
gtcaaaaatc cccatttcac cgtttcctcg tttctcctcc tcactaattt tgtctctttc      60
tcttggtttg ctattgtgct cttgtaggaa tgcagtcgtt acctatctca taccggttgt     120
ttccggccac ccaccggaaa gttctgccat tcgccgtcat ttctagccgg agctcaactt     180
ctgcacttgc gcttcgtgtc cgtacactac aatgccgctg ccttcactct tcatctctag     240
ttatggatga ggacaggttc attgaagctt ctaaaagcgg aacttgattc cgctgcaca      300 aaaccatttt ttctgatcat ctgactccgg tgctggctta ccgtgtttg gtgaaagaag      360 acgaccgtga agctccaagc tttctctttg aatccgttga acctggtttt cgaggttcta     420
gtgttggtcg ctacagcgtg gtgggggctc aaccatctat ggaaattgtg ctaaggaac      480 acaatgtgac tatattggac caccacactg gaaaattgac ccagaagact gtccaagatc     540
ccatgacgat tccgaggagt atttctgagg atggaagcc cagactcatt gatgaacttc      600
ctgatacctt ttgtggtgga tgggttggtt atttctcata tgacacagtt cggtatgtag      660
agaacaggaa gttgccattc ctaagggctc cagaggatga ccggaacctt gcagatattc     720
aattaggact atacgaagat gtcattgtgt ttgatcatgt tgagaagaaa gcacatgtga     780
ttcactgggg gcagttggat cagtattcat ctcttcctga ggcatatctt gatgggaaga     840
aacgcttgga aatattagtg tctagagtac aaggaattga gtctccaagg ttatctcccg     900
gttctgtgga tttctgtact catgctttg gaccttcatt aaccaaggga acatgacaa      960 gtgaggagta caagaatgct gtcttacaag caaaggagca cattgctgca ggagacatat    1020
ttcaaatcgt tttaagtcaa cgctttgaga agaacatt tgctgaccca tttgaagtgt     1080
acagagcatt aagaattgtg aatccaagcc catatatgac ttacatacaa gccagaggct    1140 gtatttagt tgcatcgagc ccagaaattt tgacacgtgt gaagaagaga gaattgtta     1200 atcgaccact ggctgggaca agcagaagag ggaagacacc tgatgaggat gtgatgttgg    1260
aaatgcagat gttaaaagat gagaaacaac gcgcagagca catcatgctg gttgatttag    1320
gacgaaatga tgtaggaaag gtgtcaaaac ctggttctgt gaatgtcgaa aagctcatga    1380
gcgttgagcg gtattcccat gtgatgcaca taagctccac ggtctctgga gagttgcttg    1440
```

```
atcatttaac ctgttgggat gcactacgtg ctgcattgcc tgttgggacc gtcagtggag      1500
caccaaaggt aaaggccatg gagttgattg atcagctaga agtagctcgg agagggcctt      1560
acagtggtgg gtttggaggc atttcctttt caggtgacat ggacatcgca ctagctctaa      1620
ggacgatggt attcctcaat ggagctcgtt atgacacaat gtattcatat acagatgcca      1680
gcaagcgtca ggaatgggtt gctcatctcc aatccggggc tggaattgtg ctgatagta      1740 atcctgatga ggaacagata gaatgcgaga ataaagtagc cggtctgtgc cgagccattg      1800
acttggccga gtcagctttt gtaaagggaa gacacaaacc gtcagtcaag ataaatggtt      1860
ctgtgccaaa tctattttca agggtacaac gtcaaacatc tgttatgtcg aaggacagag      1920
tacatgagaa aagaaactag cgaatatgaa gatgtacata aattctaaag tggttttctt      1980
gttcagttta atcttttact ggattgagac tgtagttgct gaagatagtt gtttagaatg      2040
accttcattt tggtgttcct gaaaggacag tgcacatata tagcaaattg atcaaatgtt      2100
taatccttgt atgcgggtga gaatcaatgc catcagcaat ttggaaaaaa aaaaaaaaaa      2160
a                                                                      2161
```

<210> SEQ ID NO 5
<211> LENGTH: 616
<212> TYPE: PRT
<213> ORGANISM: Nicotiana tabacum

<400> SEQUENCE: 5

```
Met Gln Ser Leu Pro Ile Ser Tyr Arg Leu Phe Pro Ala Thr His Arg
 1               5                  10                  15

Lys Val Leu Pro Phe Ala Val Ile Ser Ser Arg Ser Ser Thr Ser Ala
            20                  25                  30

Leu Ala Leu Arg Val Arg Thr Leu Gln Cys Arg Cys Leu His Ser Ser
        35                  40                  45

Ser Leu Val Met Asp Glu Asp Arg Phe Ile Glu Ala Ser Lys Ser Gly
    50                  55                  60

Asn Leu Ile Pro Leu His Lys Thr Ile Phe Ser Asp His Leu Thr Pro
65                  70                  75                  80

Val Leu Ala Tyr Arg Cys Leu Val Lys Glu Asp Asp Arg Glu Ala Pro
                85                  90                  95

Ser Phe Leu Phe Glu Ser Val Glu Pro Gly Phe Arg Gly Ser Ser Val
            100                 105                 110

Gly Arg Tyr Ser Val Val Gly Ala Gln Pro Ser Met Glu Ile Val Ala
        115                 120                 125

Lys Glu His Asn Val Thr Ile Leu Asp His His Thr Gly Lys Leu Thr
    130                 135                 140

Gln Lys Thr Val Gln Asp Pro Met Thr Ile Pro Arg Ser Ile Ser Glu
145                 150                 155                 160

Gly Trp Lys Pro Arg Leu Ile Asp Glu Leu Pro Asp Thr Phe Cys Gly
                165                 170                 175

Gly Trp Val Gly Tyr Phe Ser Tyr Asp Thr Val Arg Tyr Val Glu Asn
            180                 185                 190

Arg Lys Leu Pro Phe Leu Arg Ala Pro Glu Asp Asp Arg Asn Leu Ala
        195                 200                 205

Asp Ile Gln Leu Gly Leu Tyr Glu Asp Val Ile Val Phe Asp His Val
    210                 215                 220

Glu Lys Lys Ala His Val Ile His Trp Val Gln Leu Asp Gln Tyr Ser
225                 230                 235                 240
```

-continued

```
Ser Leu Pro Glu Ala Tyr Leu Asp Gly Lys Lys Arg Leu Glu Ile Leu
                245                 250                 255

Val Ser Arg Val Gln Gly Ile Glu Ser Pro Arg Leu Ser Pro Gly Ser
            260                 265                 270

Val Asp Phe Cys Thr His Ala Phe Gly Pro Ser Leu Thr Lys Gly Asn
        275                 280                 285

Met Thr Ser Glu Glu Tyr Lys Asn Ala Val Leu Gln Ala Lys Glu His
    290                 295                 300

Ile Ala Ala Gly Asp Ile Phe Gln Ile Val Leu Ser Gln Arg Phe Glu
305                 310                 315                 320

Arg Arg Thr Phe Ala Asp Pro Phe Glu Val Tyr Arg Ala Leu Arg Ile
                325                 330                 335

Val Asn Pro Ser Pro Tyr Met Thr Tyr Ile Gln Ala Arg Gly Cys Ile
            340                 345                 350

Leu Val Ala Ser Ser Pro Glu Ile Leu Thr Arg Val Lys Lys Arg Arg
        355                 360                 365

Ile Val Asn Arg Pro Leu Ala Gly Thr Ser Arg Gly Lys Thr Pro
370                 375                 380

Asp Glu Asp Val Met Leu Glu Met Gln Met Leu Lys Asp Glu Lys Gln
385                 390                 395                 400

Arg Ala Glu His Ile Met Leu Val Asp Leu Gly Arg Asn Asp Val Gly
                405                 410                 415

Lys Val Ser Lys Pro Gly Ser Val Asn Val Glu Lys Leu Met Ser Val
            420                 425                 430

Glu Arg Tyr Ser His Val Met His Ile Ser Ser Thr Val Ser Gly Glu
        435                 440                 445

Leu Leu Asp His Leu Thr Cys Trp Asp Ala Leu Arg Ala Ala Leu Pro
450                 455                 460

Val Gly Thr Val Ser Gly Ala Pro Lys Val Lys Ala Met Glu Leu Ile
465                 470                 475                 480

Asp Gln Leu Glu Val Ala Arg Arg Gly Pro Tyr Ser Gly Gly Phe Gly
                485                 490                 495

Gly Ile Ser Phe Ser Gly Asp Met Asp Ile Ala Leu Ala Leu Arg Thr
            500                 505                 510

Met Val Phe Leu Asn Gly Ala Arg Tyr Asp Thr Met Tyr Ser Tyr Thr
        515                 520                 525

Asp Ala Ser Lys Arg Gln Glu Trp Val Ala His Leu Gln Ser Gly Ala
    530                 535                 540

Gly Ile Val Ala Asp Ser Asn Pro Asp Glu Glu Gln Ile Glu Cys Glu
545                 550                 555                 560

Asn Lys Val Ala Gly Leu Cys Arg Ala Ile Asp Leu Ala Glu Ser Ala
                565                 570                 575

Phe Val Lys Gly Arg His Lys Pro Ser Val Lys Ile Asn Gly Ser Val
            580                 585                 590

Pro Asn Leu Phe Ser Arg Val Gln Arg Gln Thr Ser Val Met Ser Lys
        595                 600                 605

Asp Arg Val His Glu Lys Arg Asn
    610                 615

<210> SEQ ID NO 6
<211> LENGTH: 30
<212> TYPE: DNA (genomic)
<213> ORGANISM: Nicotiana tabacum
```

-continued

```
<400> SEQUENCE: 6
actagtggat cctctaaaag cgggaacttg                                        30

<210> SEQ ID NO 7
<211> LENGTH: 33
<212> TYPE: DNA (genomic)
<213> ORGANISM: Nicotiana tabacum

<400> SEQUENCE: 7
ttgcggggta ccctagtttc ttttctcatg tac                                    33

<210> SEQ ID NO 8
<211> LENGTH: 21
<212> TYPE: DNA (cDNA)
<213> ORGANISM: Nicotiana tabacum

<400> SEQUENCE: 8
acgactgcat tcctacaaga g                                                 21

<210> SEQ ID NO 9
<211> LENGTH: 30
<212> TYPE: DNA (cDNA)
<213> ORGANISM: Nicotiana tabacum

<400> SEQUENCE: 9
ggatcccccg ggtcctacaa gagcacaata                                        30

<210> SEQ ID NO 10
<211> LENGTH: 30
<212> TYPE: DNA (cDNA)
<213> ORGANISM: Nicotiana tabacum

<400> SEQUENCE: 10
gcatgcctgc agcaaatcta ttcgatagtg                                        30

<210> SEQ ID NO 11
<211> LENGTH: 30
<212> TYPE: DNA (cDNA)
<213> ORGANISM: Nicotiana tabacum

<400> SEQUENCE: 11
gcatgcctgc agtcagccaa atgtgtccaa                                        30

<210> SEQ ID NO 12
<211> LENGTH: 30
<212> TYPE: DNA (cDNA)
<213> ORGANISM: Nicotiana tabacum

<400> SEQUENCE: 12
gcatgcctgc agtgtattgc ccatttcatt                                        30

<210> SEQ ID NO 13
<211> LENGTH: 30
<212> TYPE: DNA (cDNA)
<213> ORGANISM: Nicotiana tabacum

<400> SEQUENCE: 13
gcatgcctgc agtaggcaat acggcacata                                        30

<210> SEQ ID NO 14
<211> LENGTH: 2297
<212> TYPE: DNA (genomic)
<213> ORGANISM: Nicotiana tabacum
```

<400> SEQUENCE: 14

```
ctagttatgg atgaggacag gttcattgaa gcttcaaatc tattcgatag tgggacctac      60
gtctcaaatc ccgaaaaaac tcgcgaaatc cgaacacccg ttccgctacg agttcaacca     120
tacaaaaatt atccaattct gatgtcaact cgaccctcaa atcttcaatt aaagtctttg     180
aagacttcta tcattttcaa ctcaatcttt atcccatttg aactaaacac tatttccata     240
aaaccttatt gatacgtata ataatactc ttacacccaa gaattatact cttaatcacc      300
catcattacc caaactcgga attgaagatt aaaaccttac ctctttgatg aagaacttga     360
gggattttt tgttggattt caaggcttgg acaagaattt gatgagcaag acactttatc     420
tacttcctct ctctagaaca ctctcacttc tctctaaaat catcagatag ttgccccaaa     480
acctatttat caaaatagag tcgggtaatg aaaataggta aatggaccct ccaaactcag     540
gtatgcgatt gcacaatgga tatacgggtc gcacaatgga ccaccaaatc gatgccgaaa     600
actgggttgc gctggacagg tctgcgaccc attttacggt cgcacaatgt gctacgaaga     660
ggaattcaca tagatttagg aagggcctgt tgtatttgtg tacaagctaa agttttttga     720
aaaacaaata cctttggtca ctttcattgt caaataggtt tttccttcgt atacctttact    780
tacatcacat agtgattatg cgatcgcaca atttaccgca taatcgtatt tttccagctt     840
ttggtaattt aatcataact ttttttatga atatccaaat gacgaactgt ttgaagcgtt     900
agaaactaga ctcaaagatc tttcatttta taggcaatac ggcacataat attttgtatc     960
atgagagtta ttctcatttg aagttaggtc ttgtgtgaac tcacttgaaa ctttagtctt    1020
atgaaatttc caacttctac atccgattcc gaaacctatc gaatcaagtc cgattgacct    1080
caaattttgc atacaagcca taatgacat aacagagcta taaaattttt cgaaacggga    1140
ttccggctcc gatatcaaaa agtcaaccct gtggtcaaac ttggaaatct ttagccttta    1200
aattactagt ttccgttaaa tggtcataac ttgagttatg gacctccaaa ttaaattccg    1260
ggcatacgcc caagtcccat atcacgatac gaacctatag gaactttcaa atatattgatc   1320
cggatccgtt tgctcaaaat gttgatcaaa gtcaactcag ttgagttta aggctctagt    1380
tcacatttta atccattttc acctaaaaac tttccggaaa attttacgga tttcgcacgc    1440
aagtcgatga atgactttg gaggtcttag aacacgtaat taattattaa atttaaagat     1500
gacattttgg ataatcaccc aagtagtaca aatttttttat gcggtgatta tatttgccaa    1560
tccatcaagc caaacatgtc gtaattagtc ataaattaag ttatacagga agaataatac    1620
gagaaatata atacctaaat taataaatac tactataaaa ttataatatt gatattgtgg    1680
ttgtattgcc catttcatta gaaaggatat atgatgtata atataaaatt ttacaatgtt    1740
attcttgttt ttaaagttaa taaaaattta aaatatgaat ttaaggttat tcttgtttat    1800
agattcttta tatcataaag ctaatcctcg tataaattat ttcatattcg actcatataa    1860
actaatactg aaattactat ataagattat ataccggtat atattggaaa cgagacatca    1920
gccaaatgtg tccaaaaata ataaatatca aattttatat caggattatt ttttttgatt    1980
atgttaacaa agttaaaagt atcagactat aaatactgta gataagatca gccattatta    2040
gagataatac tctcactacc tatattgaaa gtgaagtaga cattttctga ggtggaatat    2100
ttaaaacgtt ttcagacatt taaaacctgg aatgcggagg caaagtagtg tagtacttac    2160
tagtagtata aataagtgat cccatttca aagtcaccgt caaaaatccc catttcaccg     2220
tttcctcgtt tctcctcctc actaatttg tctctttctc ttggtttgct attgtgctct     2280
```

-continued tgtaggaatg cagtcgt                                                  2297

<210> SEQ ID NO 15
<211> LENGTH: 21
<212> TYPE: DNA (cDNA)
<213> ORGANISM: Nicotiana tabacum

<400> SEQUENCE: 15
catagccttg acttttggtg c                                               21

<210> SEQ ID NO 16
<211> LENGTH: 21
<212> TYPE: DNA (cDNA)
<213> ORGANISM: Nicotiana tabacum

<400> SEQUENCE: 16
cccaaattgt cgtgtctgaa g                                               21

<210> SEQ ID NO 17
<211> LENGTH: 21
<212> TYPE: DNA (cDNA)
<213> ORGANISM: Nicotiana tabacum

<400> SEQUENCE: 17
tctgagaaat ggaaccctga t                                               21

<210> SEQ ID NO 18
<211> LENGTH: 18
<212> TYPE: DNA (cDNA)
<213> ORGANISM: Nicotiana tabacum

<400> SEQUENCE: 18
ttcgagtctg ttgagcct                                                   18

<210> SEQ ID NO 19
<211> LENGTH: 21
<212> TYPE: DNA (cDNA)
<213> ORGANISM: Nicotiana tabacum

<400> SEQUENCE: 19
ttcttccctc tcttgctggt t                                               21

<210> SEQ ID NO 20
<211> LENGTH: 21
<212> TYPE: DNA (cDNA)
<213> ORGANISM: Nicotiana tabacum

<400> SEQUENCE: 20
aggacgaaat gatgtaggaa a                                               21

<210> SEQ ID NO 21
<211> LENGTH: 23
<212> TYPE: DNA (cDNA)
<213> ORGANISM: Nicotiana tabacum

<400> SEQUENCE: 21
cgcattctat ctgttcctca tca                                             23

<210> SEQ ID NO 22
<211> LENGTH: 670
<212> TYPE: DNA (genomic)
<213> ORGANISM: Nicotiana tabacum
<220> FEATURE:
<221> NAME/KEY: unsure

```
<222> LOCATION: 415
<221> NAME/KEY: unsure
<222> LOCATION: 416
<221> NAME/KEY: unsure
<222> LOCATION: 417
<221> NAME/KEY: unsure
<222> LOCATION: 475

<400> SEQUENCE: 22
aggacgaaat gatgtaggaa aggtttatta ctgaccattc cagaattttt gcatcaccaa      60
gagcttthat atatatcttg ttcaatgagt ggcagagagc cttgcttggt aaaaaattag    120
aaatagaaat actaaaatta ttaactgctt cctttttctg cccattttt tcatgaaatg    180
ctaacataga gggtgtcatg cagcatgaat catctgcttc tgctacactc tttaacattc    240
tagccataca aaatgcaatg tccgtccccc ttattctttc ctgttagttg ttacctctct    300
tctatgacag tgtgagtatc ttctgttcca caatatactt caggtagagc ccttttcaac    360
tgtgatagaa cccctcggcg ttggttgttt catgtaaata caacaactga acttnnnggc    420
tgcctctttt tttgtttcct gaatatgttt tgacttgcac ttgaaaaata cattnggtta    480
cccaaatatt tccttttctt gctataggtg tcaaaacctg gctctgtgaa tgttgaaaag    540
ctcatgagcg tcgagcggta ttcccatgtg atgcacataa gctccacggc gagtccatat    600
tttgatttcg tccgaggtca tactggaatc taaattgcct tttgatgttc tttgttggct    660
ctaattttcc                                                            670

<210> SEQ ID NO 23
<211> LENGTH: 491
<212> TYPE: PRT
<213> ORGANISM: Nicotiana tabacum

<400> SEQUENCE: 23

Asp Asp Arg Glu Ala Pro Ser Phe Leu Phe Glu Ser Val Glu Pro Gly
  1               5                  10                  15

Ser Gln Met Ser Ser Val Gly Arg Tyr Ser Val Val Gly Ala Gln Pro
             20                  25                  30

Ala Met Glu Ile Val Ala Lys Glu Asn Lys Val Ile Val Met Asp His
         35                  40                  45

Asn Asn Glu Thr Met Ser Glu Glu Phe Val Glu Asp Pro Met Glu Ile
     50                  55                  60

Pro Arg Lys Ile Ser Glu Lys Trp Asn Pro Asp Pro Gln Leu Val Gln
 65                  70                  75                  80

Asp Leu Pro Asp Ala Phe Cys Gly Gly Trp Val Gly Phe Phe Ser Tyr
                 85                  90                  95

Asp Thr Val Arg Tyr Val Glu Lys Arg Lys Leu Pro Phe Ser Lys Ala
            100                 105                 110

Pro Glu Asp Asp Arg Asn Leu Pro Asp Met His Leu Gly Leu Tyr Asp
        115                 120                 125

Asp Val Val Phe Asp His Val Glu Lys Lys Ala Tyr Val Ile His
    130                 135                 140

Trp Ile Arg Leu Asp Gly Ser Leu Pro Tyr Glu Lys Ala Tyr Ser Asn
145                 150                 155                 160

Gly Met Gln His Leu Glu Asn Leu Val Ala Lys Leu His Asp Ile Glu
                165                 170                 175

Pro Pro Lys Leu Ala Ala Gly Asn Val Asn Leu Gln Thr Arg Gln Phe
            180                 185                 190

Gly Pro Ser Leu Asp Asn Ser Asn Val Thr Cys Glu Glu Tyr Lys Glu
```

```
                    195                 200                 205
Ala Val Val Lys Ala Lys Glu His Ile Leu Ala Gly Asp Ile Phe Gln
    210                 215                 220
Ile Val Leu Ser Gln Arg Phe Glu Arg Arg Thr Phe Ala Asp Pro Phe
225                 230                 235                 240
Glu Val Tyr Arg Ala Leu Arg Val Val Asn Pro Ser Pro Tyr Met Gly
                245                 250                 255
Tyr Leu Gln Ala Arg Gly Cys Ile Leu Val Ala Ser Ser Pro Glu Ile
            260                 265                 270
Leu Thr Lys Val Lys Gln Asn Lys Ile Val Asn Arg Pro Leu Ala Gly
        275                 280                 285
Thr Ser Lys Arg Gly Lys Asn Glu Val Glu Asp Lys Arg Leu Glu Glu
    290                 295                 300
Leu Leu Glu Asn Glu Lys Gln Ser Ala Glu His Ile Met Leu Val Glu
305                 310                 315                 320
Leu Gly Arg Asn Asp Val Gly Lys Val Thr Lys Tyr Gly Ser Val Lys
                325                 330                 335
Val Glu Lys Leu Met Asn Ile Glu Arg Tyr Ser His Val Met His Ile
            340                 345                 350
Ser Ser Thr Val Thr Gly Glu Leu Gln Asp Gly Leu Thr Cys Trp Asp
        355                 360                 365
Val Leu Arg Ala Ala Leu Pro Val Gly Thr Val Ser Gly Ala Pro Lys
    370                 375                 380
Val Lys Ala Met Glu Leu Ile Asp Glu Leu Glu Pro Thr Arg Arg Gly
385                 390                 395                 400
Pro Tyr Ser Gly Gly Phe Gly Gly Val Ser Phe Thr Gly Asp Met Asp
                405                 410                 415
Ile Ala Leu Ser Leu Arg Thr Ile Val Phe Pro Thr Ala Cys Gln Tyr
            420                 425                 430
Asn Thr Met Tyr Ser Tyr Lys Asp Ala Asn Lys Arg Arg Glu Trp Val
        435                 440                 445
Ala Tyr Leu Gln Ala Gly Ala Gly Val Val Ala Asp Ser Asp Pro Gln
    450                 455                 460
Asp Glu His Cys Glu Cys Gln Asn Lys Ala Ala Gly Leu Ala Arg Ala
465                 470                 475                 480
Ile Asp Leu Ala Glu Ser Ala Phe Val Lys Lys
                485                 490

<210> SEQ ID NO 24
<211> LENGTH: 1650
<212> TYPE: DNA (cDNA)
<213> ORGANISM: Nicotiana tabacum

<400> SEQUENCE: 24
ggatgaccgc gaagctccta gctttctttt cgagtccgtt gagcctggtt ctcagatgtc      60
tagcgttggt cgttatagcg ttgttggggc tcagcctgcg atggagatcg tggcaaagga     120
gaataaagtt attgtaatgg atcacaacaa tgaaaccatg tctgaggaat cgtcgaaga     180 tccaatggag atcccaagaa aaatctctga gaaatggaac cctgatcctc aactagttca     240
ggaccttcca gatgcgtttt gtggtgggtg ggttggtttt ttctcgtacg acactgttcg     300
ttatgttgag aagaggaaat tgccattttc aaaggcccct gaggatgata ggaacttgcc     360
agacatgcat cttggtctgt acgacgatgt agttgtatt gatcacgtgg aaaagaaagc     420
atatgtcatt cactggatta gactagatgg gagccttcct tacgaaaagg catacagtaa     480
```

```
tggaatgcaa catttggaga acttggtggc caagttacat gatattgagc cgccaaaact      540
ggctgcaggt aacgtgaatc ttcagacacg acaatttggg ccatctttgg ataattcaaa      600
cgtgacatgc gaagagtaca aggaggctgt ggtcaaggcc aaagaacata tacttgcagg      660
agacatattt cagatcgtgc tgagtcaacg ttttgagcgg cgaacatttg cagacccctt      720
tgaagtttat agagcactaa gagttgtgaa tccaagtccg tatatgggtt atttgcaggc      780
tagaggatgc attttggtag catcaagtcc agaaattctc accaaagtaa agcagaacaa      840
gatagtgaat cggccattgg caggaaccag caagagaggg aagaatgaag ttgaggataa      900
gagattagaa taggaactgc tagagaatga aaagcaaagt gctgagcaca tcatgttggt      960
tgaactcggt cgcaacgatg ttggaaaggt tacgaaatac ggatcagtga agtagagaa      1020
gcttatgaac atcgaacgtt attcccatgt tatgcatata agctccacgg tgacaggaga     1080
attacaagat ggtttgactt gctgggacgt actacgtgcg gctttaccag tgggaacagt     1140
tagtggtgca ccaaaggtca agctatggga actaatcgat gagctagagc caacgaggcg     1200
tggaccatac agtggcggtt ttggtggagt ctccttcact ggtgacatgg acattgcttt     1260
atcccttagg acaatcgttt ttccgacagc atgtcaatac aatacaatgt actcttacaa     1320
ggatgctaac aaacggcgtg agtgggtggc ttatcttcaa gctggagctg gtgtagtagc     1380
tgatagtgac ccgcaagacg aacactgtga gtgccagaac aaagccgctg gtcttgctcg     1440
agccatcgac ttggctgaat ctgcatttgt gaaaaaatga ttgtgcccaa gaacagaggc     1500
tggctttctt tgaactccga gttcatgtgt ataaaacagt tacaagcaga acaaagtttt     1560
ttcttttct tgattttgtg agaattgcaa ttagactcca ttaatgaagc tctgaaaaat      1620
gttacaatag aaaaaaaaaa aaaaaaaaaa                                      1650

<210> SEQ ID NO 25
<211> LENGTH: 2161
<212> TYPE: DNA (cDNA)
<213> ORGANISM: Nicotiana tabacum
<220> FEATURE:
<221> NAME/KEY: CDS
<222> LOCATION: LOCATION: 90..1940

<400> SEQUENCE: 25 gt caa aaa tcc cca ttt cac cgt ttc ctc gtt tct cct cct cac taa     47
ttt tgt ctc ttt ctc ttg gtt tgc tat tgt gct ctt gta gga atg cag     95
                                                        Met Gln
                                                          1 tcg tta cct atc tca tac cgg ttg ttt ccg gcc acc cac cgg aaa gtt    143
Ser Leu Pro Ile Ser Tyr Arg Leu Phe Pro Ala Thr His Arg Lys Val
        5                   10                  15 ctg cca ttc gcc gtc att tct agc cgg agc tca act tct gca ctt gcg    191
Leu Pro Phe Ala Val Ile Ser Ser Arg Ser Ser Thr Ser Ala Leu Ala
 20                  25                  30 ctt cgt gtc cgt aca cta caa tgc cgc tgc ctt cac tct tca tct cta    239
Leu Arg Val Arg Thr Leu Gln Cys Arg Cys Leu His Ser Ser Ser Leu
35                  40                  45                  50 gtt atg gat gag gac agg ttc att gaa gct tct aaa agc ggg aac ttg    287
Val Met Asp Glu Asp Arg Phe Ile Glu Ala Ser Lys Ser Gly Asn Leu
                55                  60                  65 att ccg ctg cac aaa acc att ttt tct gat cat ctg act ccg gtg ctg    335
Ile Pro Leu His Lys Thr Ile Phe Ser Asp His Leu Thr Pro Val Leu
            70                  75                  80 gct tac cgg tgt ttg gtg aaa gaa gac gac cgt gaa gct cca agc ttt    383
Ala Tyr Arg Cys Leu Val Lys Glu Asp Asp Arg Glu Ala Pro Ser Phe
```

|  |  |
|---|---|
| ctc ttt gaa tcc gtt gaa cct ggt ttt cga ggt tct agt gtt ggt cgc<br>Leu Phe Glu Ser Val Glu Pro Gly Phe Arg Gly Ser Ser Val Gly Arg<br>100                         105                         110 | 431 |
| tac agc gtg gtg ggg gct caa cca tct atg gaa att gtg gct aag gaa<br>Tyr Ser Val Val Gly Ala Gln Pro Ser Met Glu Ile Val Ala Lys Glu<br>115                       120                       125                   130 | 479 |
| cac aat gtg act ata ttg gac cac cac act gga aaa ttg acc cag aag<br>His Asn Val Thr Ile Leu Asp His His Thr Gly Lys Leu Thr Gln Lys<br>                 135                       140                       145 | 527 |
| act gtc caa gat ccc atg acg att ccg agg agt att tct gag gga tgg<br>Thr Val Gln Asp Pro Met Thr Ile Pro Arg Ser Ile Ser Glu Gly Trp<br>     150                     155                       160 | 575 |
| aag ccc aga ctc att gat gaa ctt cct gat acc ttt tgt ggt gga tgg<br>Lys Pro Arg Leu Ile Asp Glu Leu Pro Asp Thr Phe Cys Gly Gly Trp<br>         165                     170                       175 | 623 |
| gtt ggt tat ttc tca tat gac aca gtt cgg tat gta gag aac agg aag<br>Val Gly Tyr Phe Ser Tyr Asp Thr Val Arg Tyr Val Glu Asn Arg Lys<br>180                       185                       190 | 671 |
| ttg cca ttc cta agg gct cca gag gat gac cgg aac ctt gca gat att<br>Leu Pro Phe Leu Arg Ala Pro Glu Asp Asp Arg Asn Leu Ala Asp Ile<br>195                       200                       205                   210 | 719 |
| caa tta gga cta tac gaa gat gtc att gtg ttt gat cat gtt gag aag<br>Gln Leu Gly Leu Tyr Glu Asp Val Ile Val Phe Asp His Val Glu Lys<br>                 215                       220                       225 | 767 |
| aaa gca cat gtg att cac tgg gtg cag ttg gat cag tat tca tct ctt<br>Lys Ala His Val Ile His Trp Val Gln Leu Asp Gln Tyr Ser Ser Leu<br>                 230                       235                       240 | 815 |
| cct gag gca tat ctt gat ggg aag aaa cgc ttg gaa ata tta gtg tct<br>Pro Glu Ala Tyr Leu Asp Gly Lys Lys Arg Leu Glu Ile Leu Val Ser<br>     245                     250                       255 | 863 |
| aga gta caa gga att gag tct cca agg tta tct ccc ggt tct gtg gat<br>Arg Val Gln Gly Ile Glu Ser Pro Arg Leu Ser Pro Gly Ser Val Asp<br>         260                     265                       270 | 911 |
| ttc tgt act cat gct ttt gga cct tca tta acc aag gga aac atg aca<br>Phe Cys Thr His Ala Phe Gly Pro Ser Leu Thr Lys Gly Asn Met Thr<br>275                       280                       285                   290 | 959 |
| agt gag gag tac aag aat gct gtc tta caa gca aag gag cac att gct<br>Ser Glu Glu Tyr Lys Asn Ala Val Leu Gln Ala Lys Glu His Ile Ala<br>                 295                       300                       305 | 1007 |
| gca gga gac ata ttt caa atc gtt tta agt caa cgc ttt gag aga aga<br>Ala Gly Asp Ile Phe Gln Ile Val Leu Ser Gln Arg Phe Glu Arg Arg<br>         310                     315                       320 | 1055 |
| aca ttt gct gac cca ttt gaa gtg tac aga gca tta aga att gtg aat<br>Thr Phe Ala Asp Pro Phe Glu Val Tyr Arg Ala Leu Arg Ile Val Asn<br>325                       330                       335 | 1103 |
| cca agc cca tat atg act tac ata caa gcc aga ggc tgt att tta gtt<br>Pro Ser Pro Tyr Met Thr Tyr Ile Gln Ala Arg Gly Cys Ile Leu Val<br>     340                     345                       350 | 1151 |
| gca tcg agc cca gaa att ttg aca cgt gtg aag aag aga aga att gtt<br>Ala Ser Ser Pro Glu Ile Leu Thr Arg Val Lys Lys Arg Arg Ile Val<br>355                       360                       365                   370 | 1199 |
| aat cga cca ctg gct ggg aca agc aga aga ggg aag aca cct gat gag<br>Asn Arg Pro Leu Ala Gly Thr Ser Arg Arg Gly Lys Thr Pro Asp Glu<br>         375                     380                       385 | 1247 |
| gat gtg atg ttg gaa atg cag atg tta aaa gat gag aaa caa cgc gca<br>Asp Val Met Leu Glu Met Gln Met Leu Lys Asp Glu Lys Gln Arg Ala<br>     390                     395                       400 | 1295 |
| gag cac atc atg ctg gtt gat tta gga cga aat gat gta gga aag gtg | 1343 |

```
Glu His Ile Met Leu Val Asp Leu Gly Arg Asn Asp Val Gly Lys Val
    405                 410                 415 tca aaa cct ggt tct gtg aat gtc gaa aag ctc atg agc gtt gag cgg      1391
Ser Lys Pro Gly Ser Val Asn Val Glu Lys Leu Met Ser Val Glu Arg
    420                 425                 430 tat tcc cat gtg atg cac ata agc tcc acg gtc tct gga gag ttg ctt      1439
Tyr Ser His Val Met His Ile Ser Ser Thr Val Ser Gly Glu Leu Leu
435                 440                 445                 450 gat cat tta acc tgt tgg gat gca cta cgt gct gca ttg cct gtt ggg      1487
Asp His Leu Thr Cys Trp Asp Ala Leu Arg Ala Ala Leu Pro Val Gly
                455                 460                 465 acc gtc agt gga gca cca aag gta aag gcc atg gag ttg att gat cag      1535
Thr Val Ser Gly Ala Pro Lys Val Lys Ala Met Glu Leu Ile Asp Gln
        470                 475                 480 cta gaa gta gct cgg aga ggg cct tac agt ggt ggg ttt gga ggc att      1583
Leu Glu Val Ala Arg Arg Gly Pro Tyr Ser Gly Gly Phe Gly Gly Ile
            485                 490                 495 tcc ttt tca ggt gac atg gac atc gca cta gct cta agg acg atg gta      1631
Ser Phe Ser Gly Asp Met Asp Ile Ala Leu Ala Leu Arg Thr Met Val
    500                 505                 510 ttc ctc aat gga gct cgt tat gac aca atg tat tca tat aca gat gcc      1679
Phe Leu Asn Gly Ala Arg Tyr Asp Thr Met Tyr Ser Tyr Thr Asp Ala
515                 520                 525                 530 agc aag cgt cag gaa tgg gtt gct cat ctc caa tcc ggg gct gga att      1727
Ser Lys Arg Gln Glu Trp Val Ala His Leu Gln Ser Gly Ala Gly Ile
                535                 540                 545 gtg gct gat agt aat cct gat gag gaa cag ata gaa tgc gag aat aaa      1775
Val Ala Asp Ser Asn Pro Asp Glu Glu Gln Ile Glu Cys Glu Asn Lys
        550                 555                 560 gta gcc ggt ctg tgc cga gcc att gac ttg gcc gag tca gct ttt gta      1823
Val Ala Gly Leu Cys Arg Ala Ile Asp Leu Ala Glu Ser Ala Phe Val
            565                 570                 575 aag gga aga cac aaa ccg tca gtc aag ata aat ggt tct gtg cca aat      1871
Lys Gly Arg His Lys Pro Ser Val Lys Ile Asn Gly Ser Val Pro Asn
    580                 585                 590 cta ttt tca agg gta caa cgt caa aca tct gtt atg tcg aag gac aga      1919
Leu Phe Ser Arg Val Gln Arg Gln Thr Ser Val Met Ser Lys Asp Arg
595                 600                 605                 610 gta cat gag aaa aga aac tag cga ata tga aga tgt aca taa att cta      1967
Val His Glu Lys Arg Asn
                615 aag tgg ttt tct tgt tca gtt taa tct ttt act gga ttg aga ctg tag      2015 ttg ctg aag ata gtt gtt tag aat gac ctt cat ttt ggt gtt cct gaa      2063 agg aca gtg cac ata tat agc aaa ttg atc aaa tgt tta atc ctt gta      2111 tgc ggg tga gaa tca atg cca tca gca att tgg aaa aaa aaa aaa          2159 aa                                                                    2161

<210> SEQ ID NO 26
<211> LENGTH: 30
<212> TYPE: DNA (cDNA)
<213> ORGANISM: Nicotiana tabacum

<400> SEQUENCE: 26
tgcgtacccg ggatgcagtc gttacctatc                                      30

<210> SEQ ID NO 27
<211> LENGTH: 31
<212> TYPE: DNA (cDNA)
```

<213> ORGANISM: Nicotiana tabacum

<400> SEQUENCE: 27
gccggaattc tttccaaatt gctgatggca t                         31

<210> SEQ ID NO 28
<211> LENGTH: 34
<212> TYPE: DNA (cDNA)
<213> ORGANISM: Nicotiana tabacum

<400> SEQUENCE: 28
actagtggat cctgccttca ctcttcatct ctag                       34

<210> SEQ ID NO 29
<211> LENGTH: 42
<212> TYPE: DNA (cDNA)
<213> ORGANISM: Nicotiana tabacum

<400> SEQUENCE: 29
accttgagac ccgggttcaa cggattcaaa gagaaagctt gg              42

<210> SEQ ID NO 30
<211> LENGTH: 42
<212> TYPE: DNA (cDNA)
<213> ORGANISM: Nicotiana tabacum

<400> SEQUENCE: 30
tccgttgaac ccgggtctca aggttctagt gttggtcgct ac              42

<210> SEQ ID NO 31
<211> LENGTH: 33
<212> TYPE: DNA (cDNA)
<213> ORGANISM: Nicotiana tabacum

<400> SEQUENCE: 31
ttgcggggta ccctagtttc ttttctcatg tac                        33

<210> SEQ ID NO 32
<211> LENGTH: 27
<212> TYPE: DNA (cDNA)
<213> ORGANISM: Nicotiana tabacum

<400> SEQUENCE: 32
cgattggatc catgcagtcg ttaccta                               27

<210> SEQ ID NO 33
<211> LENGTH: 30
<212> TYPE: DNA (cDNA)
<213> ORGANISM: Nicotiana tabacum

<400> SEQUENCE: 33
cagccggaat tcccaaattg ctgatggcat                            30

<210> SEQ ID NO 34
<211> LENGTH: 30
<212> TYPE: DNA (cDNA)
<213> ORGANISM: Nicotiana tabacum

<400> SEQUENCE: 34
ctgcagcaat tcatgcagtc gttacctatc                            30

<210> SEQ ID NO 35
<211> LENGTH: 21

```
<212> TYPE: DNA (cDNA)
<213> ORGANISM: Nicotiana tabacum

<400> SEQUENCE: 35
cttccctctt ctgcttgtcc c                                              21

<210> SEQ ID NO 36
<211> LENGTH: 18
<212> TYPE: DNA (cDNA)
<213> ORGANISM: Nicotiana tabacum

<400> SEQUENCE: 36 atctcaccttt gctcctgc                                                 18

<210> SEQ ID NO 37
<211> LENGTH: 18
<212> TYPE: DNA (cDNA)
<213> ORGANISM: Nicotiana tabacum

<400> SEQUENCE: 37
ataccgtaaa gcacgagg                                                  18
```